(12) United States Patent
Ohrui et al.

(10) Patent No.: US 8,072,137 B2
(45) Date of Patent: Dec. 6, 2011

(54) FUSED HETEROCYCLIC COMPOUND AND ORGANIC LIGHT EMITTING DEVICE

(75) Inventors: Hiroki Ohrui, Kawasaki (JP); Shinjiro Okada, Kamakura (JP); Akihiro Senoo, Kawasaki (JP); Naoki Yamada, Inagi (JP); Masanori Muratsubaki, Hachioji (JP)

(73) Assignee: Canon Kabushiki Kaisha, Tokyo (JP)

( * ) Notice: Subject to any disclaimer, the term of this patent is extended or adjusted under 35 U.S.C. 154(b) by 442 days.

(21) Appl. No.: 12/301,330

(22) PCT Filed: Jul. 31, 2007

(86) PCT No.: PCT/JP2007/065328
§ 371 (c)(1),
(2), (4) Date: Nov. 18, 2008

(87) PCT Pub. No.: WO2008/016166
PCT Pub. Date: Feb. 7, 2008

(65) Prior Publication Data
US 2009/0121625 A1    May 14, 2009

(30) Foreign Application Priority Data

Aug. 4, 2006  (JP) .................................. 2006-213063
Apr. 27, 2007 (JP) .................................. 2007-118218

(51) Int. Cl.
*H01L 51/54* (2006.01)
*C07D 221/18* (2006.01)

(52) U.S. Cl. ............. 313/504; 546/42; 546/26; 428/690

(58) Field of Classification Search .................. 428/690, 428/917, 411.1, 336; 313/502–509; 257/40, 257/88, 104, E51; 532/1; 540/1; 546/24, 546/42
See application file for complete search history.

(56) References Cited

U.S. PATENT DOCUMENTS 6,652,997 B2    11/2003   Suzuki et al. ................. 428/690
(Continued)

FOREIGN PATENT DOCUMENTS

JP               10-189247           7/1998
(Continued)

OTHER PUBLICATIONS

Buu-Hoi et al. (J. Chem. Soc., 1964, pp. 3920-3924).*

(Continued)

*Primary Examiner* — Angela Ortiz
*Assistant Examiner* — J. L. Yang
(74) *Attorney, Agent, or Firm* — Fitzpatrick, Cella, Harper & Scinto

(57) ABSTRACT

To provide a material for an organic light emitting device showing a light emission hue with an extremely good purity and outputting light having high luminance and a long lifetime with high efficiency, the present invention relates to a fused heterocyclic compound having at least one partial structure represented by the following general formula [1].

14 Claims, 14 Drawing Sheets

U.S. PATENT DOCUMENTS

| 2007/0249878 A1 | 10/2007 | Iwawaki et al. ............... 585/27 |
| 2007/0252141 A1 | 11/2007 | Negishi et al. ................ 257/40 |
| 2008/0286611 A1 | 11/2008 | Muratsubaki et al. ........ 428/704 |

FOREIGN PATENT DOCUMENTS

| JP | 2000-311786 | 11/2000 |
| JP | 2001-160489 | 6/2001 |
| JP | 2003-026616 | 1/2003 |
| JP | 2003-212875 | 7/2003 |
| JP | 2005-068367 | 3/2005 |
| JP | 2006-016363 | 1/2006 |

OTHER PUBLICATIONS

International Preliminary Report on Patentability issued Feb. 10, 2009 in International Application PCT/JP 2007/065328.

Buu-Hoï et al., "Carcinogenic Nitrogen Compounds. Part XL. Condensed Heterocyclic Derivatives of Fluoranthene," *J. Chem. Soc.*, pp. 3920-3924 (1964).

Eckert et al., "Synthesis of Polycylic Aromatic Heterocyclic Compounds via Thermal Isomerizations of 1,8-Diarylethynylnaphthalenes," *Monatshefte für Chemie*, vol. 129, 1035-1048 (1998).

Jaung et al., "Syntheses and Spectral Properties of New Dicyanopyrazine-Related Heterocycles from Diaminomaleonitrile," *Journal of Chemical Research, Synopses*, No. 6, 1301-1323 (1998).

Lacassagne et al., "Cancérologie—Activité Cancërogëne de Quelques Isostères Azotés D'hydrocarbures Pentacycliques Cancérogènes," *C. R. Acad. Sc. Paris*, vol. 258, 3387-3389 (1964).

Michl et al., "Polarization Spectra in Stretched Polymer Sheets—IV," *Tetrahedron*, vol. 30, 813-817 (1974).

Russell et al., "Methylation nof Aromatic Hydrocarbons by Dimethyl Sulfoxide in the Presence of Base," *J. Org. Chem.*, vol. 31, 248-251 (1966).

Sakamoto et al., "A 'Green' Route to Perylene Dyes: Direct Coupling Reactions of 1,8-Naphthalimide and Related Compounds under Mild Conditions Using a 'New' Base Complex Reagent, t-BuOK/DBN," *J. Org. Chem.*, vol. 66, 94-98 (2001).

* cited by examiner

FUSED HETEROCYCLIC COMPOUND AND ORGANIC LIGHT EMITTING DEVICE

TECHNICAL FIELD

The present invention relates to a material for an organic light emitting device having a fused, heterocyclic skeleton and an organic light emitting device using the material.

BACKGROUND ART

An organic light emitting device is a device which includes a thin film which contains a fluorescent or phosphorescent organic compound and is interposed between electrodes, in which an exciton of the fluorescent or phosphorescent compound is generated when a hole and an electron are injected from the respective electrodes and which makes use of light radiated upon return of the exciton to its ground state. The recent progress of an organic light emitting device is significant, and the device suggests its potential to use in a wide variety of applications because of the following reasons. The device shows a high luminance at a low applied voltage. In addition, the device has a variety of emission wavelengths. Furthermore, the device can be a thin, light-weight light emitting device with high-speed responsiveness.

However, at present, an optical output with additionally higher luminance, or additionally higher conversion efficiency has been needed. In addition, the organic light emitting device still has many problems in terms of durability. For example, the device changes over time owing to long-term use, and deteriorates owing to an atmospheric gas containing oxygen, or to humidity or the like. Further, assuming that the device is applied to a full-color display or the like, the device must emit blue light, green light, and red light each having good color purity, but the problems concerning the color purity have not been sufficiently solved yet.

In the meantime, compounds related to the compound of the present invention are disclosed in J. Chem. Soc. 3920 (1964), Compt. Rend. 258 (12), 3387 (1964), Tetrahedron 30, 813 (1974), and Monatsh. fur Chem. 129, 1035 (1998). However, in each of J. Chem. Soc. 3920 (1964) and Compt. Rend. 258 (12), 3387 (1964), research has been conducted mainly on the carcinogenicity of a compound having an azabenzofluoranthene skeleton. In addition, Tetrahedron 30, 813 (1974) describes the emission spectrum of an unsubstituted azabenzofluoranthene compound having a nitrogen atom at a specific position. However, the spectrum has a light emission peak in an ultraviolet region, so the compound may be lowly useful as a light emitting substance.

In addition, organic light emitting devices utilizing a compound having a diazabenzofluoranthene skeleton obtained by introducing two or more nitrogen atoms into a benzofluoranthene skeleton are disclosed in Japanese Patent Application Laid-Open No. 2001-160489, Japanese Patent Application Laid-Open No. 2003-212875, and Japanese Patent Application Laid-Open No. 2006-16363. However, Japanese Patent Application Laid-Open No. 2001-160489 and Japanese Patent Application Laid-Open No. 2003-212875 each describe a compound having a fused diazabenzofluoranthene skeleton, so a light emitting material the luminescent color of which is limited to a luminescent color having a wavelength longer than that of a blue color, in particular, to a red color is provided. In addition, Japanese Patent Application Laid-Open No. 2006-16363 describes that the compound described in the document is used mainly as an electron transporting material, and partly describes that the compound is used as a blue light emitting material. However, the luminous efficiency of the device disclosed in the document is remarkably low.

In addition, Japanese Patent Application Laid-Open No. 2000-311786 describes an organic light emitting device using a compound having an azanaphthoanthracene skeleton obtained by: causing a benzene ring to fuse with a benzofluoranthene skeleton; and introducing one nitrogen atom into the resultant. However, the application of the compound is limited to a green light emitting material owing to the skeleton of the compound.

The present invention has been made with a view to solving such problems of the prior art as described above, and an object of the present invention is to provide a material for an organic light emitting device showing a light emission hue with an extremely good purity and outputting light having high luminance and a long lifetime with high efficiency.

Another object of the present invention is to provide an organic light emitting device that can be easily produced at a relatively low cost.

DISCLOSURE OF THE INVENTION

The inventors of the present invention have made extensive studies with a view to solving the above-mentioned problems. As a result, the inventors have completed the present invention.

Therefore, according to the present invention, there is provided a fused heterocyclic compound having at least one partial structure represented by the following general formula [1]:

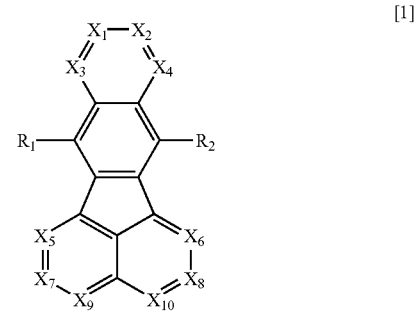

[1]

wherein:

$X_1$ to $X_{10}$ each represent a carbon atom having a substituent R or a nitrogen atom, the carbon atom or the nitrogen atom forming a ring, R represents a hydrogen atom, a halogen atom, a group selected from a substituted or unsubstituted alkyl group, a substituted or unsubstituted alkenyl group, a substituted or unsubstituted alkynyl group, a substituted or unsubstituted amino group, a substituted or unsubstituted aralkyl group, a substituted or unsubstituted aryl group, a substituted or unsubstituted heterocyclic group, a substituted or unsubstituted fused polycyclic aromatic group, a substituted or unsubstituted fused polycyclic heterocyclic group and a cyano group, or a single bond provided that at least one of $X_1$ to $X_{10}$ represents a nitrogen atom, and when a plurality of carbon atoms each having the substituent R are present, R's may be independently identical to or different from each other, and adjacent substituents may form a ring structure; and $R_1$ and $R_2$ each represent a halogen atom, a group selected from a substituted or unsubstituted alkyl group, a substituted or unsubstituted alkenyl group, a substituted or unsubstituted alkynyl group, a substituted or unsubstituted amino group, a substituted or unsubstituted aralkyl group, a substituted or unsubstituted aryl group, a substituted or unsubstituted heterocyclic group, a substituted or unsubstituted fused polycyclic aromatic group, a substituted or unsubstituted fused polycyclic heterocyclic group and a cyano group, or a single bond, and $R_1$ and $R_2$ may be identical to or different from each other.

The fused heterocyclic compound provided by the present invention has a nitrogen-containing aromatic heterocyclic ring obtained by introducing a nitrogen atom into a specific position of a benzofluoranthene skeleton, so the compound can provide a stable amorphous film property and shows excellent electron transporting property. Further, an emission spectrum showing a wide range of luminescent colors and having a controlled molecular vibration can be monodispersed, and its half width can be reduced depending on the position where the nitrogen atom is introduced, and various combinations of the kind of a substituent and the position where the substituent is introduced, so a light emitting material having a good color purity can be provided.

In addition, an organic light emitting device containing the fused heterocyclic compound provided by the present invention can emit light having high luminance at a low applied voltage, and is excellent in durability. In particular, an organic light emitting device using the fused heterocyclic compound as a guest for its light emitting layer exerts the following excellent effect. That is, the device has such extensibility that the device shows a wide range of light emission hues ranging from a blue light emission hue having a light emission peak at 430 nm or more to 460 nm or less and an extremely good purity to a red light emission hue having a light emission peak at 590 nm or more to 630 nm or less as a result of proper molecular modification of the compound. In addition, the device can emit light having high luminance at a low applied voltage, and is excellent in durability.

Further features of the present invention will become apparent from the following description of exemplary embodiments with reference to the attached drawings.

BEST MODE FOR CARRYING OUT THE INVENTION

Figure 1:
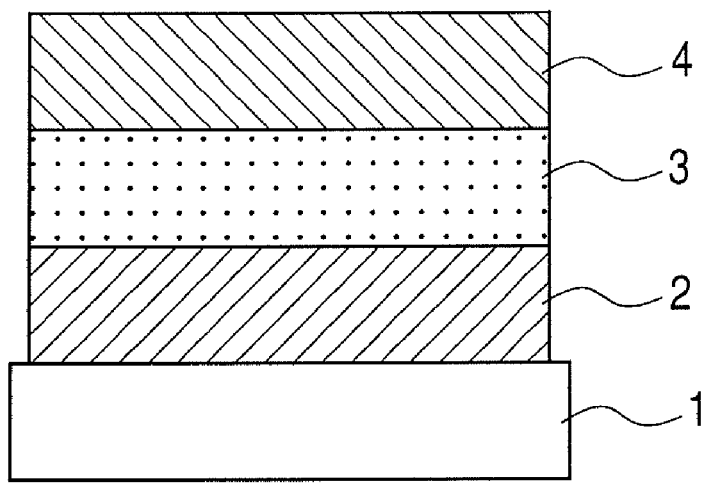
FIG. 1 is a sectional view showing an example of an organic light emitting device of the present invention.

Hereinafter, the present invention will be described in detail.

First, a fused heterocyclic compound of the present invention will be described.

The fused heterocyclic compound of the present invention has at least one partial structure represented by the above general formula [1]. R in the general formula [1] preferably represents any one of the following: a hydrogen atom, a group selected from a substituted or unsubstituted alkyl group, a substituted or unsubstituted amino group, a substituted or unsubstituted aryl group, a substituted or unsubstituted heterocyclic group, a substituted or unsubstituted fused polycyclic aromatic group and a substituted or unsubstituted fused polycyclic heterocyclic group, and a single bond.

In addition, $R_1$ and $R_2$ each preferably represent any one of the following: a group selected from a substituted or unsubstituted alkyl group, a substituted or unsubstituted aryl group, a substituted or unsubstituted heterocyclic group, a substituted or unsubstituted fused polycyclic aromatic group and a substituted or unsubstituted fused polycyclic heterocyclic group, and a single bond.

An example of the fused heterocyclic compound of the present invention is a compound in which none of R, $R_1$, and $R_2$ in the general formula [1] represents a single bond.

Another example of the fused heterocyclic compound is a compound represented by the following general formula [2]:

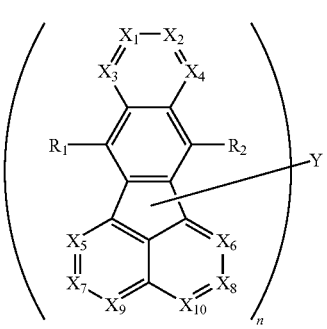

[2]

wherein:
$X_1$ to $X_{10}$ each represent a carbon atom having a substituent R or a nitrogen atom, the carbon atom or the nitrogen atom forming a ring, at least one of $X_1$ to $X_{10}$ represents a nitrogen atom, and when a plurality of carbon atoms each having the substituent R are present, R's may be independently identical to or different from each other;
Y represents a single bond, or an n-valent linking group derived from a substituted or unsubstituted alkane, a substituted or unsubstituted alkene, a substituted or unsubstituted alkyne, a substituted or unsubstituted amine, a substituted or unsubstituted aromatic ring, a substituted or unsubstituted heterocyclic ring, a substituted or unsubstituted fused polycyclic aromatic ring, or a substituted or unsubstituted fused polycyclic heterocyclic ring;

$R_1$ and $R_2$ each represent a group selected from a substituted or unsubstituted alkyl group, a substituted or unsubstituted aryl group, a substituted or unsubstituted heterocyclic group, a substituted or unsubstituted fused polycyclic aromatic group, and a substituted or unsubstituted fused polycyclic heterocyclic group, and $R_1$ and $R_2$ may be identical to or different from each other;

Y is bonded to any one of a carbon atom represented by any one of $X_1$ to $X_{10}$, $R_1$, and $R_2$; and n represents an integer of 2 or more to 10 or less.

In addition, another example of the fused heterocyclic compound is a compound represented by the following general formula [3], more specifically, a compound represented by the following general formula [4] or [5]:

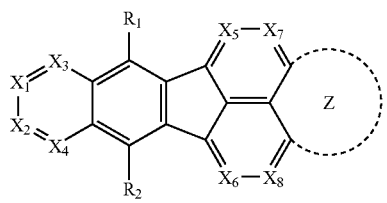

[3]

wherein:

Z represents a ring structure;

$X_1$ to $X_8$ each represent a carbon atom having a substituent R or a nitrogen atom, the carbon atom or the nitrogen atom forming a ring, at least one of $X_1$ to $X_8$ represents a nitrogen atom, R represents a hydrogen atom, a halogen atom, or a group selected from a substituted or unsubstituted alkyl group, a substituted or unsubstituted amino group, a substituted or unsubstituted aralkyl group, a substituted or unsubstituted aryl group, a substituted or unsubstituted heterocyclic group, a substituted or unsubstituted fused polycyclic aromatic group, a substituted or unsubstituted fused polycyclic heterocyclic group, and a cyano group, and when a plurality of carbon atoms each having the substituent R are present, R's may be independently identical to or different from each other; and $R_1$ and $R_2$ each represent a halogen atom, or a group selected from a substituted or unsubstituted alkyl group, a substituted or unsubstituted amino group, a substituted or unsubstituted aralkyl group, a substituted or unsubstituted aryl group, a substituted or unsubstituted heterocyclic group, a substituted or unsubstituted fused polycyclic aromatic group, a substituted or unsubstituted fused polycyclic heterocyclic group and a cyano group, and $R_1$ and $R_2$ may be identical to or different from each other,

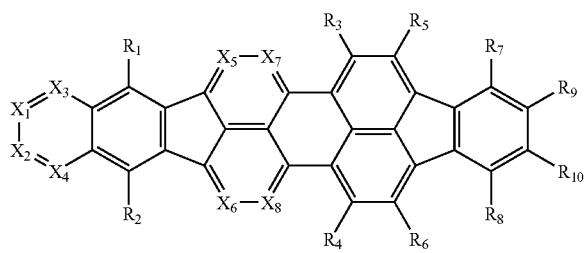

[4]

wherein:

$X_1$ to $X_8$ each represent a carbon atom having a substituent R or a nitrogen atom, the carbon atom or the nitrogen atom forming a ring, at least one of $X_1$ to $X_8$ represents a nitrogen atom, R represents a hydrogen atom, a halogen atom, or a group selected from a substituted or unsubstituted alkyl group, a substituted or unsubstituted amino group, a substituted or unsubstituted aralkyl group, a substituted or unsubstituted aryl group, a substituted or unsubstituted heterocyclic group, a substituted or unsubstituted fused polycyclic aromatic group, a substituted or unsubstituted fused polycyclic heterocyclic group and a cyano group; and $R_1$ to $R_{10}$ each represent a halogen atom, or a group selected from a substituted or unsubstituted alkyl group, a substituted or unsubstituted amino group, a substituted or unsubstituted aralkyl group, a substituted or unsubstituted aryl group, a substituted or unsubstituted heterocyclic group, a substituted or unsubstituted fused polycyclic aromatic group, a substituted or unsubstituted fused polycyclic heterocyclic group and a cyano group, and $R_1$ to $R_{10}$ may be identical to or different from one another, and

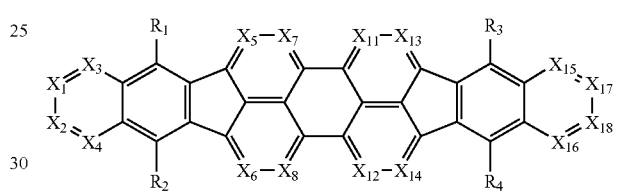

[5]

wherein:

$X_1$ to $X_{18}$ each represent a carbon atom having a substituent R or a nitrogen atom, the carbon atom or the nitrogen atom forming a ring, at least one of $X_1$ to $X_{18}$ represents a nitrogen atom, R represents a hydrogen atom, a halogen atom, or a group selected from a substituted or unsubstituted alkyl group, a substituted or unsubstituted amino group, a substituted or unsubstituted aralkyl group, a substituted or unsubstituted aryl group, a substituted or unsubstituted heterocyclic group, a substituted or unsubstituted fused polycyclic aromatic group, a substituted or unsubstituted fused polycyclic heterocyclic group, and a cyano group, and when a plurality of carbon atoms each having the substituent R are present, R's may be independently identical to or different from each other; and $R_1$ to $R_4$ each represent a halogen atom, or a group selected from a substituted or unsubstituted alkyl group, a substituted or unsubstituted amino group, a substituted or unsubstituted aralkyl group, a substituted or unsubstituted aryl group, a substituted or unsubstituted heterocyclic group, a substituted or unsubstituted fused polycyclic aromatic group, a substituted or unsubstituted fused polycyclic heterocyclic group and a cyano group, and $R_1$ to $R_4$ may be identical to or different from one another.

A compound having an azabenzofluoranthene structure is an additionally preferable example of the fused heterocyclic compound. More preferable examples of the fused heterocyclic compound include a compound represented by any one of the general formulae [1] to [4] in which $X_1$ or $X_2$ represents a nitrogen atom, and a compound represented by the general formula [5] in which at least one of $X_1$, $X_2$, $X_{17}$, and $X_{18}$ represents a nitrogen atom.

The fused heterocyclic compound of the present invention can be used as a material for an organic light emitting device. When the compound is used for a light emitting layer in the device, the compound can be used alone in the light emitting layer, or can be used in the layer for the purpose of serving as a dopant (guest) material or a host material, whereby a device emitting light with high efficiency, maintaining high luminance for a long time period, and showing small deterioration due to energization can be obtained.

When a light emission layer is composed of a host material and a guest each having carrier transport property, light emission mainly involves some of the following processes:

1. the transport of an electron or a hole in the light emission layer;
2. the generation of an exciton of the host;
3. the transfer of excitation energy between host molecules; and
4. the transfer of excitation energy from the host to the guest.

Desired energy transfer or light emission in each process occurs in competition with various deactivation processes.

It is needless to say that an improvement in luminous efficiency of an EL device requires a material itself that is mainly responsible for light emission to have a large light emission quantum yield. However, how efficiently energy can be transferred between hosts or between a host and a guest is also of great concern. In addition, no cause for the degradation of light emission due to energization has been revealed at present. However, the degradation is assumed to be related to at least the material itself that is mainly responsible for light emission or a change in environment surrounding the luminescent material due to a molecule around the material.

In view of the foregoing, the inventors of the present invention have made various studies, and have found that, when a fused ring compound represented by the general formula [1] is especially used as a host or guest. for the light emission layer of a device, the device emits light with high efficiency, maintains high luminance for a long time period, and shows small degradation of light emission due to energization.

One possible cause for the deterioration of light emission due to energization is the deterioration of the thin film shape of the light emitting layer. The deterioration of the thin film shape is considered to result from the crystallization of an organic thin film due to, for example, the temperature of an environment in which the device is driven, and heat generation at the time of the driving of the device. This is considered to originate from the low glass transition temperature of a material for the device, so an organic EL material is required to have a high glass transition temperature. The fused heterocyclic compound of the present invention has a high glass transition temperature, so an achievement in high durability of an organic EL device can be expected.

In addition, the fused heterocyclic compound of the present invention is a material having a high reduction potential and large electron accepting property because an atom having high electronegativity is inserted into the fused aromatic ring structure of the compound. In addition, electron mobility can be adjusted by controlling the reduction potential through the selection of R and Y in the compound represented by any one of the general formulae [1]. to [5]. In view of the foregoing, the inventors have found that the voltage at which the device is driven can be reduced, high luminance can be maintained for a long time period, and the deterioration of the device due to energization can be reduced by properly selecting R and Y in the compound represented by any one of the general formulae [1] to [5] through a combination with any one of various host materials.

Further, the inventors have found that a wide range of luminescent colors ranging from a pure blue color to a red color can be shown by properly modifying the molecular structure represented by the general formula [1] as represented by any one of the general formulae [2] to [5], so a material having the molecular structure represented by the general formula [1] is a light emitting material having extensibility.

In addition, an improvement in quantum yield of a light emitting material to be used in an organic electroluminescence device is indispensable for providing an organic electroluminescence device having an optical output with high efficiency. When a nitrogen atom is introduced mainly into a fused polycyclic aromatic group, the n-Π* orbital of a triplet becomes an orbital at a Tn level (n represents 1 or more) depending on the position where the atom is introduced. Then, when the n-Π* orbital (triplet) is energetically close to an S1 orbital, energy deactivation from the S1 orbital to the n-Π* orbital is apt to occur, so the quantum yield of the light emitting material is apt to reduce. However, the proper selection of the position where the nitrogen atom is introduced and the kind of a substituent to be introduced into the molecular skeleton of the light emitting material can increase a difference in energy between the n-Π* orbital (triplet) and the S1 orbital, and can alleviate the reduction in quantum yield. The position where the nitrogen atom is introduced is preferably simulated on the basis of molecular orbital calculation. That is, nitrogen atoms are more preferably introduced into the positions of $X_1$ and $X_2$ represented in the general formula [1] on the basis of the design of a molecular skeleton capable of maintaining high quantum yield.

Further, an emission spectrum having a controlled molecular vibration can be monodispersed, and its half width can be reduced by properly designing not only the position where a nitrogen atom is introduced but also the position and kind of a substituent to be introduced into the molecular skeleton of a light emitting material, so a light emitting material having a good color purity can be provided.

Further, the introduction of substituents into $R_1$ and $R_2$ represented in the general formula [1] prevents molecules of the compound of the present invention from associating with each other. As a result, upon use of the compound of the present invention as a light emitting material for an organic electroluminescence device, an increase in wavelength of light to be emitted from the device due to the molecular association of the light emitting material itself can be prevented, whereby an organic electroluminescence device having a good color purity can be provided.

Further, the positions of $X_9$ and $X_{10}$ represented in the general formula [1] have high reactivity, so the introduction of a ring structure such as Z represented in the general formula [3] as a structure having a substituent introduced into each of the positions can improve the chemical stability of the compound of the present invention.

The present invention has been made as a result of molecular design based on the foregoing discussion.

Examples of the substituted or unsubstituted alkyl group in any one of the above general formulae. [1] to [5] include, but of course are not limited to, the following.

A methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, 2-chloroethyl group, a 2,2,2-trichloroethyl group, a 4-chlorobutyl group, a 5-chloropentyl group, a 6 chlorohexyl group, a bromomethyl group, a 2-bromoethyl group, an iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, and an adamantyl group.

Examples of the substituted amino group include a dimethylamino group, a diethylamino group, a dibenzylamino group, a diphenylamino group, a ditolylamino group, a dianisolylamino group, and a carbazoyl group. From the viewpoints of conductive property and glass transition temperature, a dimethylamino group, a diphenylamino group, a ditolylamino group, and a carbazoyl group are preferable.

Examples of the substituted or unsubstituted aralkyl group include, but of course are not limited to, the following.

A benzyl group, a 2-phenylethyl group, a 2-phenylisopropyl group, a 1-naphthylmethyl group, a 2-naphthylmethyl group, a 2-(1-naphthyl)ethyl group, a 2-(2-naphthyl)ethyl group, a 9-anthrylmethyl group, a 2-(9-anthryl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, and a 4-bromobenzyl group.

Examples of the substituted or unsubstituted aryl group include, but of course are not limited to, the following.

A phenyl group, a 4-methylphenyl group, a 4-ethylphenyl group, a 4-fluorophenyl group, a 4-trifluorophenyl group, a 3,5-dimethylphenyl group, a 2,6-diethylphenyl group, a mesityl group, a 4-tert-butylphenyl group, a ditolylaminophenyl group, and a biphenyl group.

Examples of the substituted or unsubstituted fused polycyclic aromatic group include, but of course are not limited to, the following.

A naphthyl group, an acenaphthylenyl group, an anthryl group, a phenanthryl group, a pyrenyl group, an acephenanthrylenyl group, an aceanthrylenyl group, a chrysenyl group, a dibenzochrysenyl group, a benzoanthryl group, a dibenzoanthryl group, a naphthacenyl group, a picenyl group, a pentacenyl group, a fluorenyl group, a 9,9-dihydroanthryl group, a triphenylenyl group, a perylenyl group, and a fluoranthenyl group.

Examples of the substituted or unsubstituted heterocyclic group include, but of course are not limited to, the following.

A pyridyl group, a pyrrolyl group, a bipyridyl group, a methylpyridyl group, a pyrimidinyl group, a pyrazinyl group, a pyridazinyl group, a terpyrrolyl group, a thienyl group, a terthienyl group, a propylthienyl group, a furyl group, an oxazolyl group, an oxadiazolyl group, a thiazolyl group, and a thiadiazolyl group.

Examples of the substituted or unsubstituted fused polycyclic heterocyclic group include, but of course are not limited to, the following.

A quinolyl group, an isoquinolyl group, a benzothienyl group, a dibenzothienyl group, a benzofuryl group, an isobenzofuryl group, a dibenzofuryl group, a quinoxalinyl group, a naphthylidinyl group, a quinazolinyl group, a phenanthridinyl group, an indolidinyl group, a phenadinyl group, a carbazolyl group, an acridinyl group, a phenadinyl group, and a diazafluorenyl group.

Examples of the halogen atom include fluorine, chlorine, bromine, and iodine.

Examples of a substituent which the above substituents may additionally have include, but of course are not limited to, the following.

Alkyl groups such as a methyl group, an ethyl group, a propyl group, a tert-butyl group, and a trifluoromethyl group; aryl groups such as a phenyl group and a biphenyl group; heterocyclic groups such as a thienyl group and a pyrrolyl group; amino groups such as a dimethylamino group, a diethylamino group, dibenzylamino group, a diphenylamino group, ditolylamino group, and a dianisolylamino group; alkoxy groups such as a methoxy group, and an ethoxy group; halogen atoms such as fluorine, chlorine, bromine, and iodine; hydroxyl group; cyano group; and nitro group.

Hereinafter, specific structural formulae of the fused heterocyclic compound of the present invention are shown below. However, these formulae are merely representative examples, and the present invention is not limited to them.

Compound Example 1

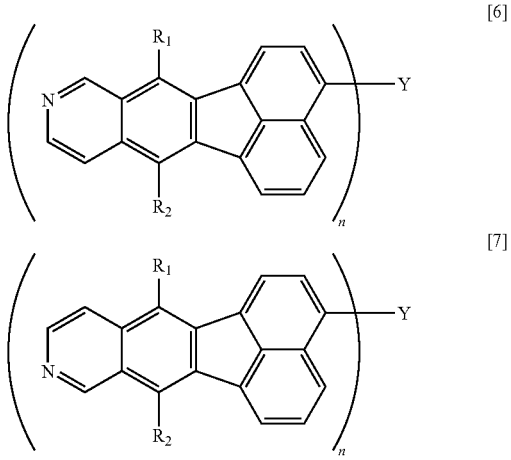

wherein:

Y represents a linking group which is divalent or more such as a phenylene group or a biphenylene group; and $R_1$ and $R_2$ each represent an aryl group such as a phenyl group, a fused polycyclic aromatic group with three or less rings such as a fluorenyl group, or an alkyl group such as a methyl group or a butyl group.

When $R_1$ and $R_2$ are different from each other, $R_1$ and $R_2$ shown in the following tables may be replaced with each other.

In the tables, "Compd. No." is Compound No.

TABLE 1

| Compd. No. | n | R1 | R2 | Y |
|---|---|---|---|---|
| 1001 | 2 | phenyl | phenyl | phenylene |

TABLE 1-continued

| Compd. No. | n | R1 | R2 | Y |
|---|---|---|---|---|
| 1002 | 2 | phenyl | CH$_3$— | 1,4-phenylene |
| 1003 | 2 | phenyl | C$_4$H$_9$— | 1,4-phenylene |
| 1004 | 2 | CH$_3$— | CH$_3$— | 1,4-phenylene |
| 1005 | 2 | C$_4$H$_9$— | C$_4$H$_9$— | 1,4-phenylene |
| 1006 | 2 | phenyl | phenyl | 1,3-phenylene |
| 1007 | 2 | phenyl | CH$_3$— | 1,3-phenylene |
| 1008 | 2 | phenyl | C$_4$H$_9$— | 1,3-phenylene |
| 1009 | 2 | CH$_3$— | CH$_3$— | 1,3-phenylene |
| 1010 | 2 | C$_4$H$_9$— | C$_4$H$_9$— | 1,3-phenylene |
| 1011 | 2 | phenyl | phenyl | 4,4'-biphenylene |
| 1012 | 2 | phenyl | C$_4$H$_9$— | 4,4'-biphenylene |
| 1013 | 2 | CH$_3$— | CH$_3$— | 4,4'-biphenylene |
| 1014 | 2 | C$_4$H$_9$— | C$_4$H$_9$— | 4,4'-biphenylene |
| 1015 | 2 | phenyl | phenyl | 3,3'-biphenylene |

TABLE 1-continued
| Compd. No. | n | R1 | R2 | Y |
|---|---|---|---|---|
| 1016 | 2 | 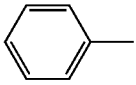 | C₄H₉— | 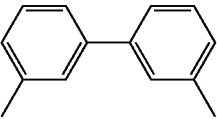 |
| 1017 | 2 | CH₃— | CH₃— | 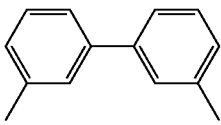 |
| 1018 | 2 | C₄H₉— | C₄H₉— | 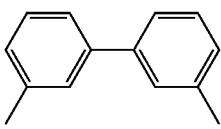 |
TABLE 2
| Compd. No. | n | R1 | R2 | Y |
|---|---|---|---|---|
| 1019 | 2 | 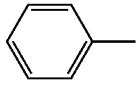 | 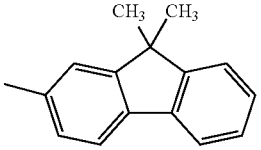 |  |
| 1020 | 2 | CH₃— | 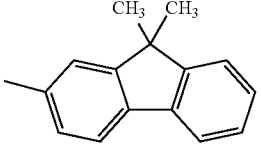 |  |
| 1021 | 2 | C₄H₉— | 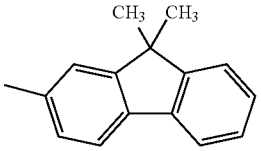 |  |
| 1022 | 2 | 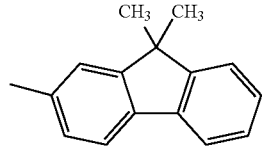 | 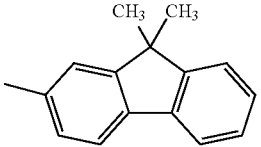 |  |
| 1023 | 2 | 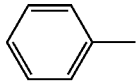 | 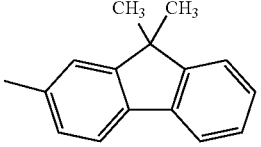 | 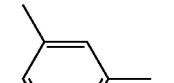 |
| 1024 | 2 | CH₃— | 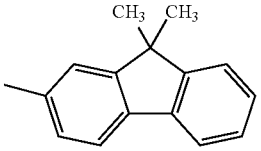 | 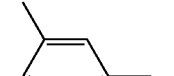 |

TABLE 2-continued

| Compd. No. | n | R1 | R2 | Y |
|---|---|---|---|---|
| 1025 | 2 | C4H9— | 9,9-dimethyl-2-fluorenyl | m-phenylene |
| 1026 | 2 | 9,9-dimethyl-2-fluorenyl | 9,9-dimethyl-2-fluorenyl | m-phenylene |
| 1027 | 2 | phenyl | 9,9-dimethyl-2-fluorenyl | 4,4'-biphenylene |
| 1028 | 2 | CH3— | 9,9-dimethyl-2-fluorenyl | 4,4'-biphenylene |
| 1029 | 2 | C4H9— | 9,9-dimethyl-2-fluorenyl | 4,4'-biphenylene |
| 1030 | 2 | 9,9-dimethyl-2-fluorenyl | 9,9-dimethyl-2-fluorenyl | 4,4'-biphenylene |

TABLE 3

| Compd. No. | n | R1 | R2 | Y |
|---|---|---|---|---|
| 1031 | 2 | phenyl | 9,9-dimethyl-2-fluorenyl | 3,3'-biphenylene |
| 1032 | 2 | CH3— | 9,9-dimethyl-2-fluorenyl | 3,3'-biphenylene |

TABLE 3-continued

| Compd. No. | n | R1 | R2 | Y |
| --- | --- | --- | --- | --- |
| 1033 | 2 | C₄H₉— | 2-(9,9-dimethylfluorenyl) | 3,3'-biphenylene |
| 1034 | 2 | 2-(9,9-dimethylfluorenyl) | 2-(9,9-dimethylfluorenyl) | 3,3'-biphenylene |
| 1035 | 2 | phenyl | 2,7-di-tert-butyl-4,9,9-trimethylfluorenyl | 1,4-phenylene |
| 1036 | 2 | CH₃— | 2,7-di-tert-butyl-4,9,9-trimethylfluorenyl | 1,4-phenylene |
| 1037 | 2 | C₄H₉— | 2,7-di-tert-butyl-4,9,9-trimethylfluorenyl | 1,4-phenylene |

TABLE 4

| Compd. No | n | R1 | R2 | Y |
|---|---|---|---|---|
| 1038 | 2 | 2,7-di-tert-butyl-4-methyl-9,9-dimethyl-6-tert-butylfluoren-3-yl | 2,7-di-tert-butyl-4-methyl-9,9-dimethyl-6-tert-butylfluoren-3-yl | 1,4-phenylene |
| 1039 | 2 | phenyl | 2,7-di-tert-butyl-4-methyl-9,9-dimethyl-6-tert-butylfluoren-3-yl | 1,3-phenylene |
| 1040 | 2 | $CH_3-$ | 2,7-di-tert-butyl-4-methyl-9,9-dimethyl-6-tert-butylfluoren-3-yl | 1,3-phenylene |
| 1041 | 2 | $C_4H_9-$ | 2,7-di-tert-butyl-4-methyl-9,9-dimethyl-6-tert-butylfluoren-3-yl | 1,3-phenylene |

TABLE 4-continued

| Compd. No | n | R1 | R2 | Y |
|---|---|---|---|---|
| 1042 | 2 | 2,4-di-tert-butyl-7-tert-butyl-9,9-dimethylfluorenyl | 2,4-di-tert-butyl-7-tert-butyl-9,9-dimethylfluorenyl | m-phenylene |

TABLE 5

| Compd. No. | n | R1 | R2 | Y |
|---|---|---|---|---|
| 1043 | 2 | phenyl | 2-tert-butyl-4-methyl-7-tert-butyl-9,9-dimethylfluorenyl | 4,4'-biphenylene |
| 1044 | 2 | CH₃— | 2-tert-butyl-4-methyl-7-tert-butyl-9,9-dimethylfluorenyl | 4,4'-biphenylene |

TABLE 5-continued

| Compd. No. | n | R1 | R2 | Y |
| --- | --- | --- | --- | --- |
| 1045 | 2 | C4H9— | (4-methyl-9,9-dimethyl-2,7-di-tert-butylfluorenyl) | 4,4'-biphenylene |
| 1046 | 2 | (4-methyl-9,9-dimethyl-2,7-di-tert-butylfluorenyl) | (4-methyl-9,9-dimethyl-2,7-di-tert-butylfluorenyl) | 4,4'-biphenylene |
| 1047 | 2 | phenyl | (4-methyl-9,9-dimethyl-2,7-di-tert-butylfluorenyl) | 3,3'-biphenylene |

TABLE 6

| Compd. No. | n | R1 | R2 | Y |
|---|---|---|---|---|
| 1048 | 2 | CH₃— | 2,7-di-tert-butyl-4,9,9-trimethylfluorenyl | 3,3'-biphenylene |
| 1049 | 2 | C₄H₉— | 2,7-di-tert-butyl-4,9,9-trimethylfluorenyl | 3,3'-biphenylene |
| 1050 | 2 | 2,7-di-tert-butyl-4,9,9-trimethylfluorenyl | 2,7-di-tert-butyl-4,9,9-trimethylfluorenyl | 3,3'-biphenylene |
| 1051 | 3 | phenyl | phenyl | 1,3,5-benzenetriyl |
| 1052 | 3 | CH₃— | CH₃— | 1,3,5-benzenetriyl |

TABLE 6-continued
| Compd. No. | n | R1 | R2 | Y |
|---|---|---|---|---|
| 1053 | 3 | C$_4$H$_9$— | C$_4$H$_9$— | 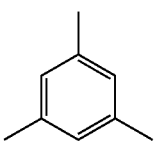 |
| 1054 | 3 | 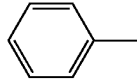 | 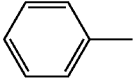 | 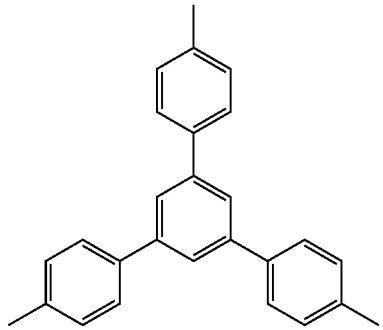 |
TABLE 7
| Compd. No. | n | R1 | R2 | Y |
|---|---|---|---|---|
| 1055 | 3 | CH$_3$— | CH$_3$— | 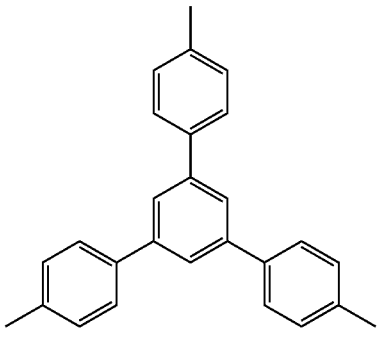 |
| 1056 | 3 | C$_4$H$_9$— | C$_4$H$_9$— | 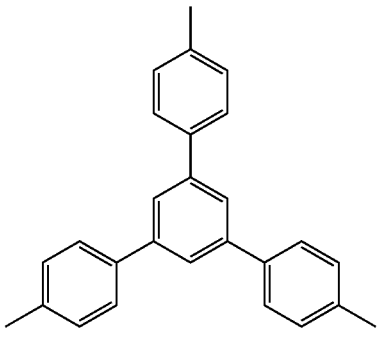 |

TABLE 7-continued
| Compd. No. | n | R1 | R2 | Y |
|---|---|---|---|---|
| 1057 | 3 | 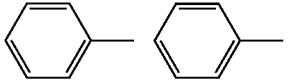 | 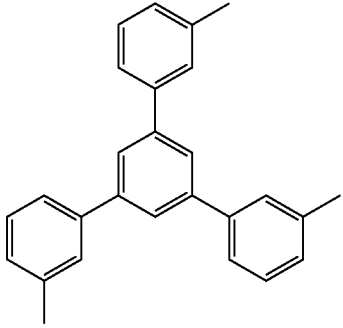 | 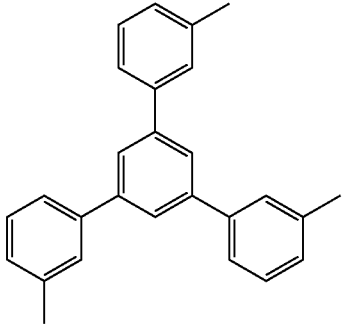 |
| 1058 | 3 | CH₃— | CH₃— | 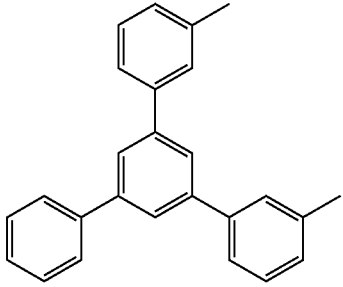 |
| 1059 | 3 | C₄H₉— | C₄H₉— |  |
| 1060 | 4 | 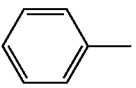 | 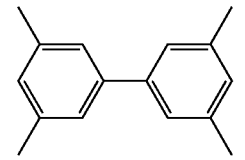 | 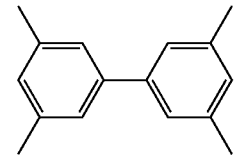 |
| 1061 | 4 | CH₃— | CH₃— | 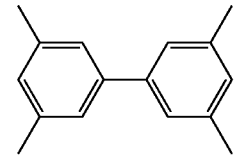 |
| 1062 | 4 | C₄H₉— | C₄H₉— | |

Compound Example 2

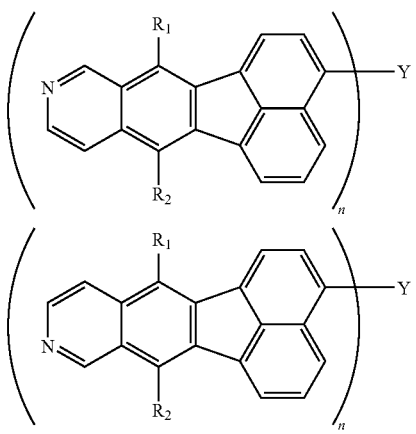

wherein:

Y represents a linking group which is divalent or more such as a phenylene group or a biphenylene group; and At least one of $R_1$ and $R_2$ represents a heterocyclic group such as a pyridyl group, or a fused polycyclic heterocyclic group such as a quinolyl group.

When $R_1$ and $R_2$ are different from each other, $R_1$ and $R_2$ shown in the following tables may be replaced with each other.

TABLE 8

| Compd. No. | n | R1 | R2 | Y |
|---|---|---|---|---|
| 1101 | 2 | 2-pyridyl | phenyl | 1,4-phenylene |
| 1102 | 2 | 2-pyridyl | $CH_3-$ | 1,4-phenylene |
| 1103 | 2 | 2-pyridyl | $C_4H_9-$ | 1,4-phenylene |
| 1104 | 2 | 2-pyridyl | phenyl | 1,3-phenylene |
| 1105 | 2 | 2-pyridyl | $CH_3-$ | 1,3-phenylene |
| 1106 | 2 | 2-pyridyl | $C_4H_9-$ | 1,3-phenylene |
| 1107 | 2 | 2-pyridyl | phenyl | 4,4'-biphenylene |
| 1108 | 2 | 2-pyridyl | $CH_3-$ | 4,4'-biphenylene |
| 1109 | 2 | 2-pyridyl | $C_4H_9-$ | 4,4'-biphenylene |

TABLE 8-continued
| Compd. No. | n | R1 | R2 | Y |
|---|---|---|---|---|
| 1110 | 2 | 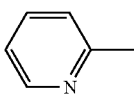 | 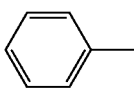 | 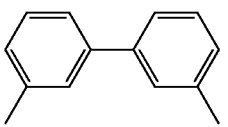 |
| 1111 | 2 | 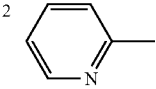 | CH$_3$— | 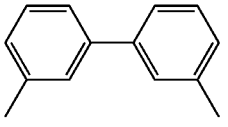 |
| 1112 | 2 | 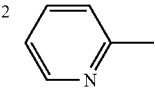 | C$_4$H$_9$— | 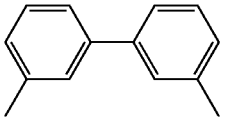 |
| 1113 | 2 | 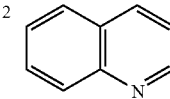 | 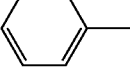 | 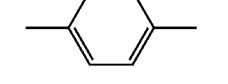 |
| 1114 | 2 | 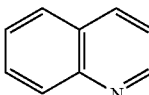 | CH$_3$— |  |
| 1115 | 2 | 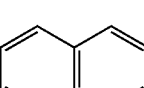 | C$_4$H$_9$— | 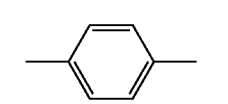 |
TABLE 9
| Compd. No. | n | R1 | R2 | Y |
|---|---|---|---|---|
| 1116 | 2 | 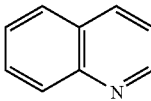 | 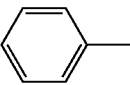 | 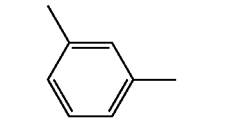 |
| 1117 | 2 | 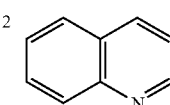 | CH$_3$— | 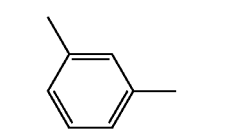 |
| 1118 | 2 | 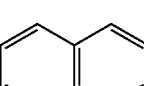 | C$_4$H$_9$— | 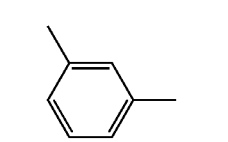 |
| 1119 | 2 | 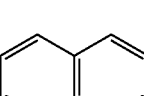 | 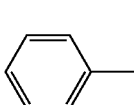 | 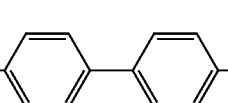 |

TABLE 9-continued

| Compd. No. | n | R1 | R2 | Y |
|---|---|---|---|---|
| 1120 | 2 | 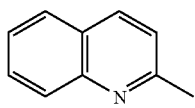 | CH₃— | 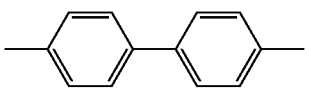 |
| 1121 | 2 | 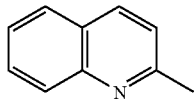 | C₄H₉— | 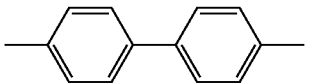 |
| 1122 | 2 | 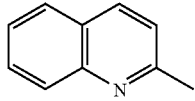 | 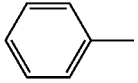 | 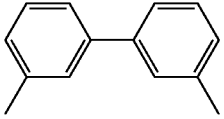 |
| 1123 | 2 | 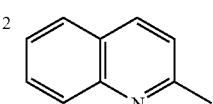 | CH₃— | 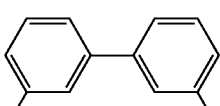 |
| 1124 | 2 | 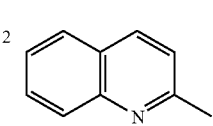 | C₄H₉— | 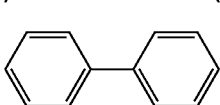 |

Compound Example 3

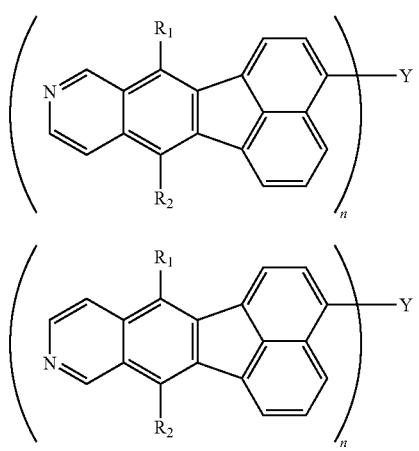

In the compound example:

[6] Y represents a linking group which is divalent or more and is formed of a fused polycyclic aromatic group such as a naphthylene group, an anthrylene group, or a fluorenylene group; and

[7] $R_1$ and $R_2$ each represent an aryl group such as a phenyl group, a fused polycyclic aromatic group with three or less rings such as a fluorenyl group, or an alkyl group such as a methyl group.

When $R_1$ and $R_2$ are different from each other, $R_1$ and $R_2$ shown in the following tables may be replaced with each other.

TABLE 10

| Compd. No. | n | R1 | R2 | Y |
|---|---|---|---|---|
| 1201 | 2 | 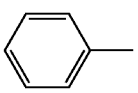 | 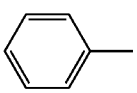 | 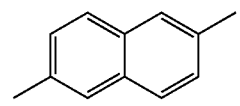 |

TABLE 10-continued
| Compd. No. | n | R1 | R2 | Y |
|---|---|---|---|---|
| 1202 | 2 | 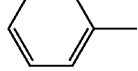 | CH₃— | 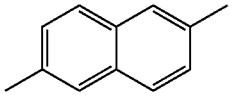 |
| 1203 | 2 | 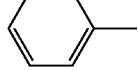 | C₄H₉— | 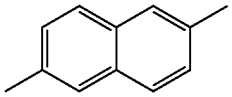 |
| 1204 | 2 | 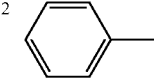 | 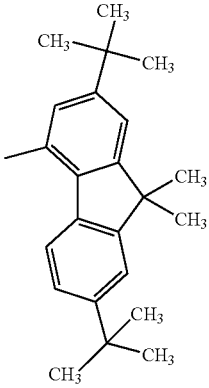 | 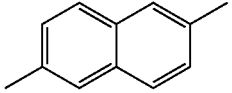 |
| 1205 | 2 | 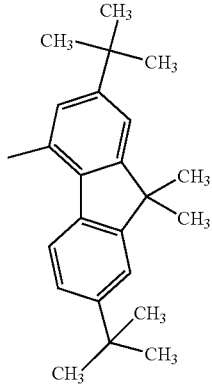 | 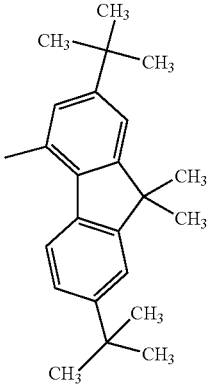 | 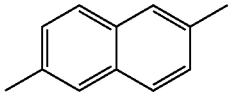 |
| 1206 | 2 | 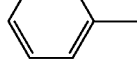 | 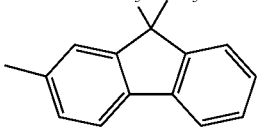 | 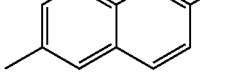 |
| 1207 | 2 | 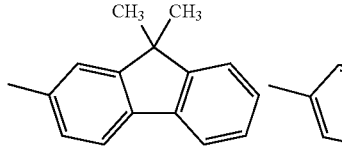 | 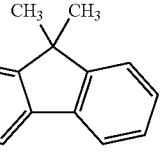 | 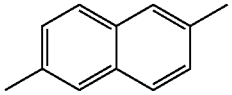 |
| 1208 | 2 | CH₃— | CH₃— | 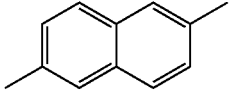 |
| 1209 | 2 | C₄H₉— | C₄H₉— | 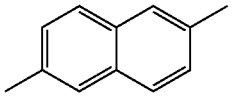 |

TABLE 10-continued
| Compd. No. | n | R1 | R2 | Y |
|---|---|---|---|---|
| 1210 | 2 | 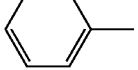 | 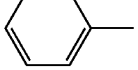 | 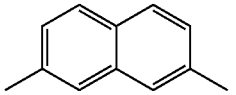 |
| 1211 | 2 | 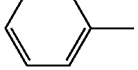 | CH$_3$— | 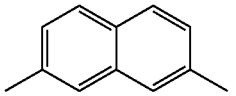 |
| 1212 | 2 | 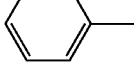 | C$_4$H$_9$— | 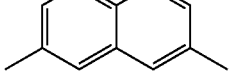 |
TABLE 11
| Compd. No. | n | R1 | R2 | Y |
|---|---|---|---|---|
| 1213 | 2 | 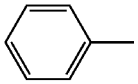 | 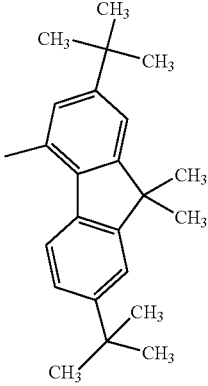 | 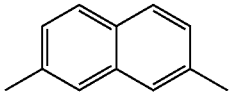 |
| 1214 | 2 | 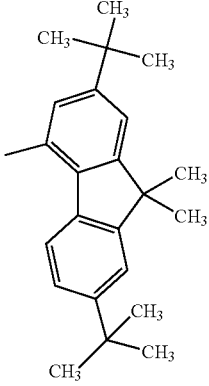 | 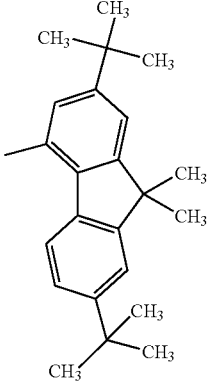 | 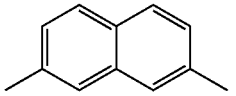 |
| 1215 | 2 | 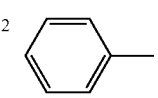 | 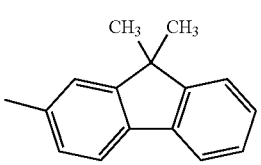 | 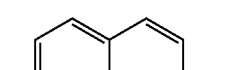 |

TABLE 11-continued
| Compd. No. | n | R1 | R2 | Y |
|---|---|---|---|---|
| 1216 | 2 |  |  |  |
| 1217 | 2 | CH₃— | CH₃— |  |
| 1218 | 2 | C₄H₉— | C₄H₉— |  |
| 1219 | 2 |  |  |  |
| 1220 | 2 |  | CH₃— |  |
| 1221 | 2 |  | C₄H₉— |  |
TABLE 12
| Compd. No. | n | R1 | R2 | Y |
|---|---|---|---|---|
| 1222 | 2 |  |  |  |

TABLE 12-continued

| Compd. No. | n | R1 | R2 | Y |
|---|---|---|---|---|
| 1223 | 2 | 2,7-di-tert-butyl-4-methyl-9,9-dimethylfluorenyl | 2,7-di-tert-butyl-4-methyl-9,9-dimethylfluorenyl | 1,4-naphthylene |
| 1224 | 2 | phenyl | 9,9-dimethylfluoren-2-yl | 1,4-naphthylene |
| 1225 | 2 | 9,9-dimethylfluoren-2-yl | 9,9-dimethylfluoren-2-yl | 1,4-naphthylene |
| 1226 | 2 | CH₃— | CH₃— | 1,4-naphthylene |
| 1227 | 2 | C₄H₉— | C₄H₉— | 1,4-naphthylene |
| 1228 | 2 | phenyl | phenyl | 1,5-naphthylene |
| 1229 | 2 | phenyl | CH₃— | 1,5-naphthylene |
| 1230 | 2 | phenyl | C₄H₉— | 1,5-naphthylene |

TABLE 13
| Compd. No. | n | R1 | R2 | Y |
|---|---|---|---|---|
| 1231 | 2 | CH₃— | CH₃— | 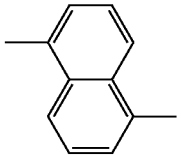 |
| 1232 | 2 | C₄H₉— | C₄H₉— | 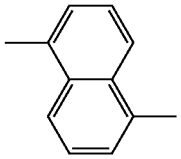 |
| 1233 | 2 | 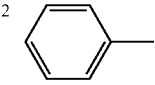 | 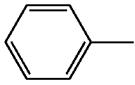 | 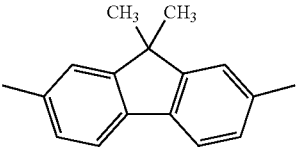 |
| 1234 | 2 | 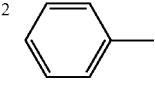 | C₄H₉— | 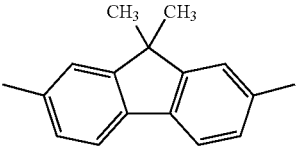 |
| 1235 | 2 | 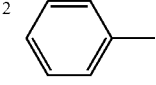 | 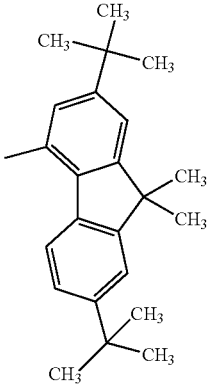 | 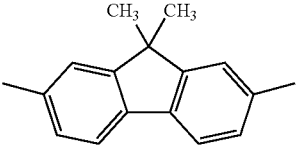 |
| 1236 | 2 | 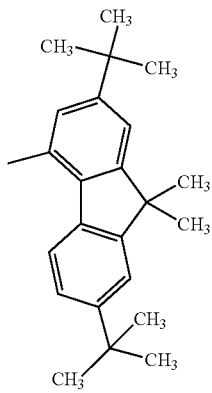 | 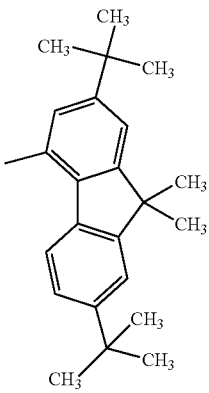 | 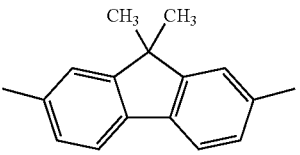 |

TABLE 13-continued
| Compd. No. | n | R1 | R2 | Y |
|---|---|---|---|---|
| 1237 | 2 | 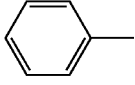 | 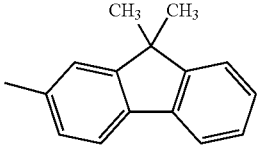 | 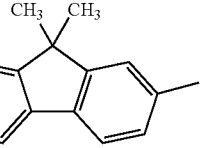 |
| 1238 | 2 |  | 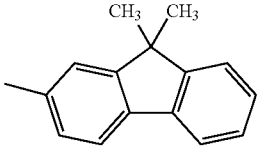 | 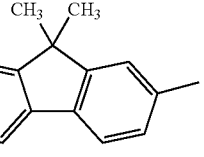 |
TABLE 14
| Compd. No. | n | R1 | R2 | Y |
|---|---|---|---|---|
| 1239 | 2 | CH$_3$— | CH$_3$— | 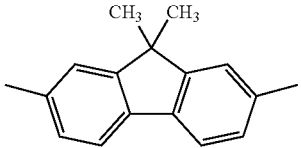 |
| 1240 | 2 | C$_4$H$_9$— | C$_4$H$_9$— | 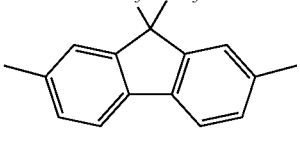 |
| 1241 | 2 | 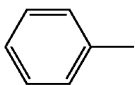 | 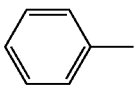 | 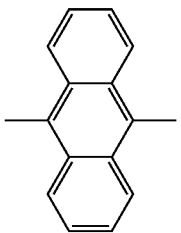 |
| 1242 | 2 | 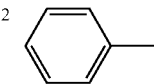 | C$_4$H$_9$— | 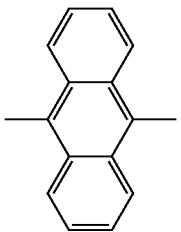 |

TABLE 14-continued
| Compd. No. | n | R1 | R2 | Y |
|---|---|---|---|---|
| 1243 | 2 | 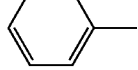 | 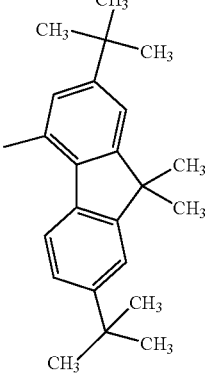 | 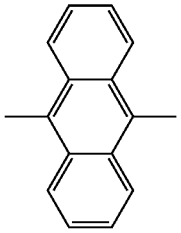 |
| 1244 | 2 | 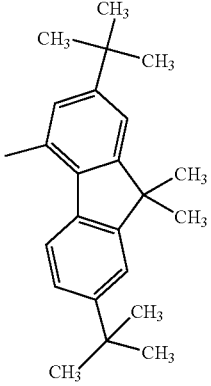 | 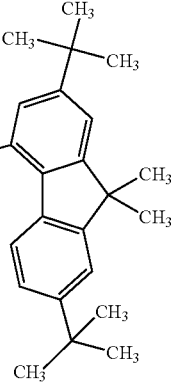 | 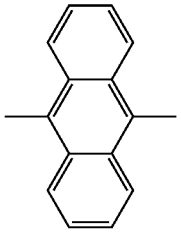 |
| 1245 | 2 | 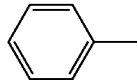 | 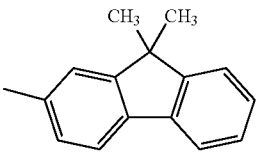 | 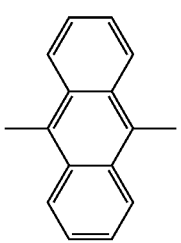 |
TABLE 15
| Compd. No. | n | R1 | R2 | Y |
|---|---|---|---|---|
| 1246 | 2 | 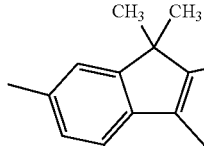 | 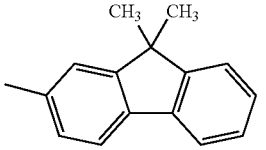 | 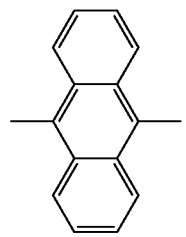 |

TABLE 15-continued
| Compd. No. | n | R1 | R2 | Y |
|---|---|---|---|---|
| 1247 | 2 | CH₃— | CH₃— | 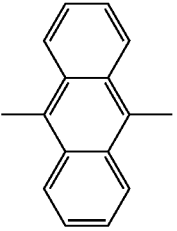 |
| 1248 | 2 | C₄H₉— | C₄H₉— | 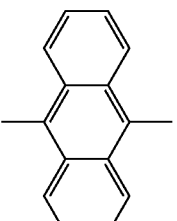 |
| 1249 | 2 | 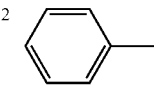 | 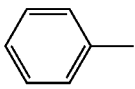 | 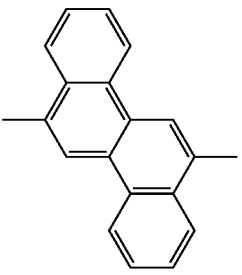 |
| 1250 | 2 | 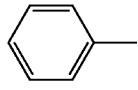 | C₄H₉— | 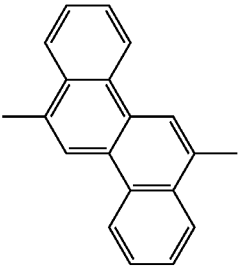 |
| 1251 | 2 | 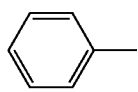 | 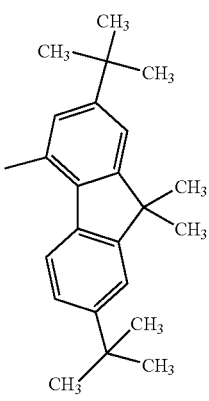 | 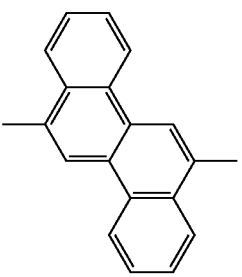 |

TABLE 16
| Compd. No. | n | R1 | R2 | Y |
|---|---|---|---|---|
| 1252 | 2 | 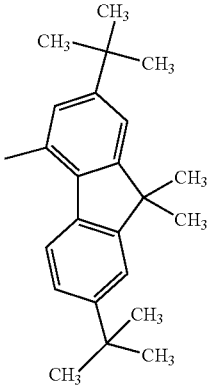 | 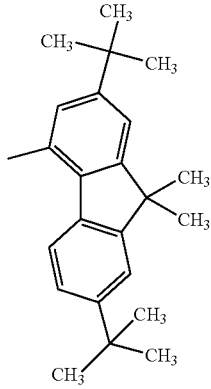 | 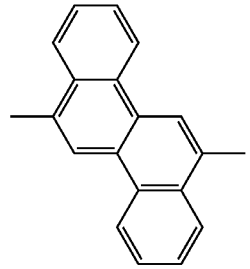 |
| 1253 | 2 | 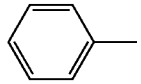 | 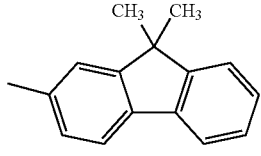 | 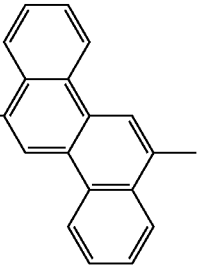 |
| 1254 | 2 | 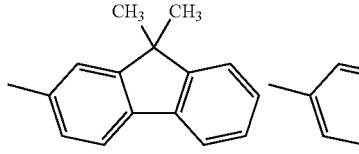 | 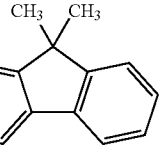 | 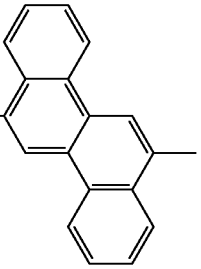 |
| 1255 | 2 | CH₃— | CH₃— | 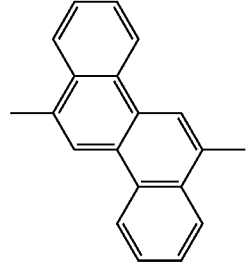 |
| 1256 | 2 | C₄H₉— | C₄H₉— | 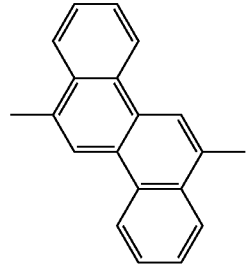 |

Compound Example 4

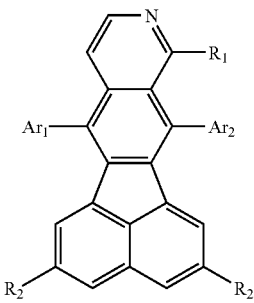

wherein:

[8] Ar$_1$ and Ar$_2$ each represent an aryl group such as a phenyl group or a biphenyl group, or a fused polycyclic aromatic group with three or less rings such as a naphthyl group, a fluorenyl group, or a phenanthryl group; and R$_1$ and R$_2$ each represent a hydrogen atom, or an alkyl group such as a methyl group, an ethyl group, or a tertiary butyl group.

When Ar$_1$ and Ar$_2$ are different from each other, Ar$_1$ and Ar$_2$ shown in the following tables may be replaced with each other.

TABLE 17

| Compd. No. | Ar1 | Ar2 | R1 | R2 |
|---|---|---|---|---|
| 1301 | phenyl | phenyl | H— | H— |
| 1302 | phenyl | phenyl | CH$_3$— | H— |
| 1303 | phenyl | phenyl | CH$_3$— | tert-butyl |
| 1304 | phenyl | phenyl | H— | tert-butyl |
| 1305 | phenyl | 9,9-dimethylfluorenyl | CH$_3$— | H— |
| 1306 | phenyl | 9,9-dimethylfluorenyl | CH$_3$— | H— |
| 1307 | phenyl | 9,9-dimethylfluorenyl | H— | tert-butyl |
| 1308 | 9,9-dimethylfluorenyl | 9,9-dimethylfluorenyl | H— | H— |

TABLE 17-continued

| Compd. No. | Ar1 | Ar2 | R1 | R2 |
|---|---|---|---|---|
| 1309 | 9,9-dimethylfluoren-2-yl | 9,9-dimethylfluoren-2-yl | CH₃— | H— |
| 1310 | 9,9-dimethylfluoren-2-yl | 9,9-dimethylfluoren-2-yl | H— | tert-butyl |
| 1311 | 9,9-dimethylfluoren-2-yl | 9,9-dimethylfluoren-2-yl | CH₃— | tert-butyl |
| 1312 | 9,9-dimethylfluoren-2-yl | 9-methyl-9-trifluoromethylfluoren-2-yl | H— | H— |
| 1313 | 9,9-dimethylfluoren-2-yl | 9-methyl-9-trifluoromethylfluoren-2-yl | CH₃— | H— |
| 1314 | 9,9-dimethylfluoren-2-yl | 9-methyl-9-trifluoromethylfluoren-2-yl | H— | tert-butyl |
| 1315 | 9-methyl-9-trifluoromethylfluoren-2-yl | 9-methyl-9-trifluoromethylfluoren-2-yl | H— | H— |

TABLE 18

| Compd. No. | Ar1 | Ar2 | R1 | R2 |
|---|---|---|---|---|
| 1316 | 9-methyl-9-trifluoromethylfluoren-2-yl | 9-methyl-9-trifluoromethylfluoren-2-yl | CH₃— | H— |

TABLE 18-continued

| Compd. No. | Ar1 | Ar2 | R1 | R2 |
|---|---|---|---|---|
| 1317 | [9-CH₃,9-CF₃-2-methylfluorenyl] | [9-CH₃,9-CF₃-2-methylfluorenyl] | H— | tert-butyl |
| 1318 | [9,9-dimethyl-2-methylfluorenyl] | [2,7-di-tert-butyl-4,9,9-trimethylfluorenyl] | H— | H— |
| 1319 | [9,9-dimethyl-2-methylfluorenyl] | [2,7-di-tert-butyl-4,9,9-trimethylfluorenyl] | CH₃— | H— |
| 1320 | [9,9-dimethyl-2-methylfluorenyl] | [2,7-di-tert-butyl-4,9,9-trimethylfluorenyl] | H— | tert-butyl |

TABLE 18-continued

| Compd. No. | Ar1 | Ar2 | R1 | R2 |
|---|---|---|---|---|
| 1321 | 9,9-dimethyl-2-methylfluorenyl | 2-tert-butyl-4,9,9-trimethyl-7-isopropylfluorenyl | CH₃— | tert-butyl |
| 1322 | 2-tert-butyl-4,9,9-trimethyl-7-isopropylfluorenyl | 2-tert-butyl-4,9,9-trimethyl-7-isopropylfluorenyl | H— | H— |

TABLE 19

| Compd. No. | Ar1 | Ar2 | R1 | R2 |
|---|---|---|---|---|
| 1323 | 2-tert-butyl-4,9,9-trimethyl-7-tert-butylfluorenyl | 2-tert-butyl-4,9,9-trimethyl-7-tert-butylfluorenyl | CH₃— | H— |

TABLE 19-continued

| Compd. No. | Ar1 | Ar2 | R1 | R2 |
|---|---|---|---|---|
| 1324 | 2,4,7-tri-substituted-9,9-dimethylfluorenyl (2,7-di-tert-butyl, 4-methyl) | 2,4,7-tri-substituted-9,9-dimethylfluorenyl (2,7-di-tert-butyl, 4-methyl) | H— | tert-butyl |
| 1325 | 2,4,7-tri-substituted-9,9-dimethylfluorenyl (2,7-di-tert-butyl, 4-methyl) | 2,4,7-tri-substituted-9,9-dimethylfluorenyl (2,7-di-tert-butyl, 4-methyl) | CH₃— | tert-butyl |
| 1326 | phenyl | phenanthrenyl | H— | H— |
| 1327 | phenyl | phenanthrenyl | CH₃— | H— |
| 1328 | tolyl | phenanthrenyl | H— | tert-butyl |
| 1329 | 2,7-disubstituted-9,9-dimethylfluorenyl | phenanthrenyl | H— | H— |

TABLE 19-continued

| Compd. No. | Ar1 | Ar2 | R1 | R2 |
|---|---|---|---|---|
| 1330 | 9,9-dimethyl-2-fluorenyl | 10-methyl-phenanthrenyl | CH₃— | H— |
| 1331 | 9,9-dimethyl-2-fluorenyl | 10-methyl-phenanthrenyl | H— | (CH₃)₃C— |

TABLE 20

| Compd. No. | Ar1 | Ar2 | R1 | R2 |
|---|---|---|---|---|
| 1332 | 9-phenanthrenyl | 9-phenanthrenyl | H— | H— |
| 1333 | 9-phenanthrenyl | 9-phenanthrenyl | CH₃— | H— |
| 1334 | 9-phenanthrenyl | 9-phenanthrenyl | H— | (CH₃)₃C— |
| 1335 | phenyl | 2-naphthyl | H— | H— |
| 1336 | phenyl | 2-naphthyl | CH₃— | H— |
| 1337 | phenyl | 2-naphthyl | H— | (CH₃)₃C— |
| 1338 | 2-naphthyl | 2-naphthyl | H— | H— |

TABLE 20-continued

| Compd. No. | Ar1 | Ar2 | R1 | R2 |
|---|---|---|---|---|
| 1339 | 2-naphthyl | 2-naphthyl | CH$_3$— | H— |
| 1340 | 2-naphthyl | 2-naphthyl | H— | (CH$_3$)$_3$C— |

Compound Example 5

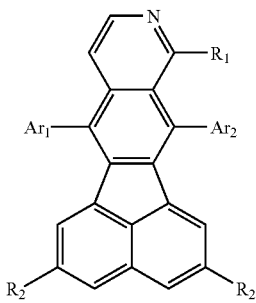

wherein:

At least one of Ar$_1$ and Ar$_2$ represents a fused polycyclic aromatic group with four or more rings such as a fluoranthenyl group, a pyrenyl group, or a chrysenyl group; and R$_1$ and R$_2$ each represent a hydrogen atom, or an alkyl group such as a methyl group, an ethyl group, or a tertiary butyl group.

When Ar$_1$ and Ar$_2$ are different from each other, Ar$_1$ and Ar$_2$ shown in the following tables may be replaced with each other.

TABLE 21

| Compd. No. | Ar1 | Ar2 | R1 | R2 |
|---|---|---|---|---|
| 1401 | pyrenyl | phenyl | H— | H— |
| 1402 | pyrenyl | phenyl | CH$_3$— | H— |
| 1403 | pyrenyl | phenyl | H— | (CH$_3$)$_3$C— |

TABLE 21-continued

| Compd. No. | Ar1 | Ar2 | R1 | R2 |
|---|---|---|---|---|
| 1404 | pyrenyl | 9,9-dimethylfluorenyl | H— | H— |
| 1405 | pyrenyl | 9,9-dimethylfluorenyl | $CH_3$— | H— |
| 1406 | pyrenyl | 9,9-dimethylfluorenyl | H— | tert-butyl |
| 1407 | pyrenyl | 2,7-di-tert-butyl-4,9,9-trimethylfluorenyl | H— | H— |
| 1408 | pyrenyl | 2,7-di-tert-butyl-4,9,9-trimethylfluorenyl | $CH_3$— | H— |

TABLE 21-continued

| Compd. No. | Ar1 | Ar2 | R1 | R2 |
|---|---|---|---|---|
| 1409 | pyrenyl | di-tert-butyl-methyl-dimethylfluorenyl | H— | tert-butyl |

TABLE 22

| Compd. No. | Ar1 | Ar2 | R1 | R2 |
|---|---|---|---|---|
| 1410 | pyrenyl | pyrenyl | H— | H— |
| 1411 | pyrenyl | pyrenyl | CH₃— | H— |
| 1412 | pyrenyl | pyrenyl | H— | tert-butyl |
| 1413 | fluoranthenyl | phenyl | H— | H— |

TABLE 22-continued

| Compd. No. | Ar1 | Ar2 | R1 | R2 |
|---|---|---|---|---|
| 1414 | fluoranthene | phenyl | CH₃— | H— |
| 1415 | fluoranthene | phenyl | H— | tert-butyl |
| 1416 | fluoranthene | 9,9-dimethylfluorenyl | H— | H— |
| 1417 | fluoranthene | 9,9-dimethylfluorenyl | CH₃— | H— |
| 1418 | fluoranthene | 9,9-dimethylfluorenyl | H— | tert-butyl |

TABLE 22-continued

| Compd. No. | Ar1 | Ar2 | R1 | R2 |
|---|---|---|---|---|
| 1419 | (fluoranthene with methyl) | (9,9-dimethylfluorene with tert-butyl, tert-butyl, and methyl substituents) | H— | H— |

TABLE 23

| Compd. No. | Ar1 | Ar2 | R1 | R2 |
|---|---|---|---|---|
| 1420 | (fluoranthene with methyl) | (9,9-dimethylfluorene with tert-butyl, tert-butyl, and methyl substituents) | CH₃— | H— |
| 1421 | (fluoranthene with methyl) | (9,9-dimethylfluorene with tert-butyl, tert-butyl, and methyl substituents) | H— | (CH₃)₃C— |
| 1422 | (fluoranthene with methyl) | (methylpyrene) | H— | H— |

TABLE 23-continued
| Compd. No. | Ar1 | Ar2 | R1 | R2 |
|---|---|---|---|---|
| 1423 | 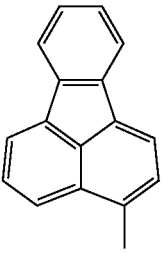 | 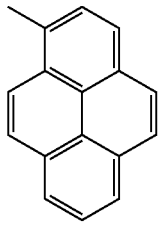 | CH₃— | H— |
| 1424 | 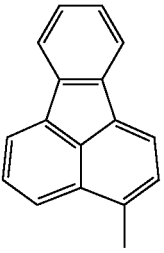 | 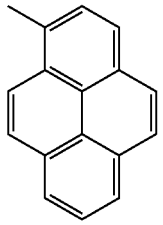 | H— | (CH₃)₃C— |
| 1425 | 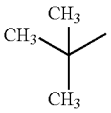 | 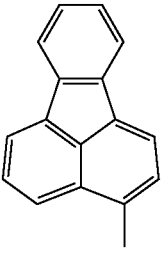 | H— | H— |
| 1426 | 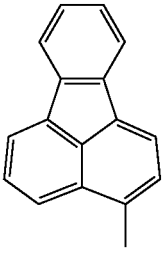 | 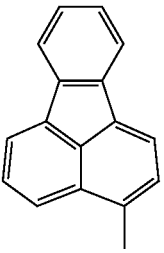 | CH₃— | H— |
| 1427 | 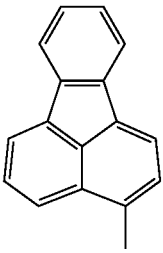 | 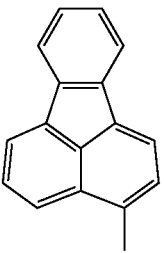 | H— | (CH₃)₃C— |

TABLE 23-continued

| Compd. No. | Ar1 | Ar2 | R1 | R2 |
|---|---|---|---|---|
| 1428 | (chrysenyl) | (fluoranthenyl) | H— | H— |

TABLE 24

| Compd. No. | Ar1 | Ar2 | R1 | R2 |
|---|---|---|---|---|
| 1429 | (chrysenyl) | (fluoranthenyl) | CH$_3$— | H— |
| 1430 | (chrysenyl) | (fluoranthenyl) | H— | C(CH$_3$)$_3$ |
| 1431 | (chrysenyl) | (pyrenyl) | H— | H— |
| 1432 | (chrysenyl) | (pyrenyl) | CH$_3$— | H— |

TABLE 24-continued
| Compd. No. | Ar1 | Ar2 | R1 | R2 |
|---|---|---|---|---|
| 1433 | | | H— | (CH₃)₃C— |
| 1434 | | | H— | H— |
| 1435 | | | CH₃— | H— |
| 1436 | | | H— | (CH₃)₃C— |
Compound Example 6
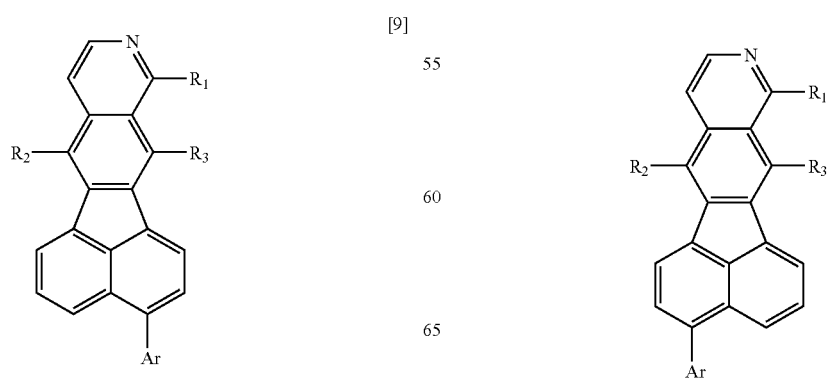

wherein:

R₁ represents a hydrogen atom, or an alkyl group such as a methyl group or an ethyl group;

R₂ and R₃ each represent an aryl group such as a phenyl group, a fused polycyclic aromatic group with three or less rings such as a fluorenyl group, or an alkyl group such as a methyl group; and Ar represents a fused polycyclic aromatic group such as a naphthyl group, a fluorenyl group, a pyrenyl group, a fluoranthenyl group, or a benzofluoranthenyl group.

When R₂ and R₃ are different from each other, R₂ and R₃ shown in the following tables may be replaced with each other.

TABLE 25

| Compd. No. | R1 | R2 | R3 | Ar |
|---|---|---|---|---|
| 1501 | H— | phenyl | phenyl | fluoranthenyl |
| 1502 | CH₃— | phenyl | phenyl | fluoranthenyl |
| 1503 | H— | phenyl | CH₃— | fluoranthenyl |
| 1504 | CH₃— | phenyl | CH₃— | fluoranthenyl |
| 1505 | H— | phenyl | C₄H₉— | fluoranthenyl |
| 1506 | CH₃— | phenyl | C₄H₉— | fluoranthenyl |
| 1507 | H— | 9,9-dimethylfluorenyl | 9,9-dimethylfluorenyl | fluoranthenyl |

TABLE 25-continued

| Compd. No. | R1 | R2 | R3 | Ar |
|---|---|---|---|---|
| 1508 | CH₃— | 9,9-dimethyl-2-fluorenyl (methyl-substituted) | 9,9-dimethyl-2-fluorenyl (methyl-substituted) | methyl-fluoranthenyl |
| 1509 | H— | 9,9-dimethyl-2,4-di(tert-butyl)-7-(tert-butyl)fluorenyl | 9,9-dimethyl-2,4-di(tert-butyl)-7-(tert-butyl)fluorenyl | methyl-fluoranthenyl |
| 1510 | CH₃— | 9,9-dimethyl-2,4-di(tert-butyl)-7-(tert-butyl)fluorenyl | 9,9-dimethyl-2,4-di(tert-butyl)-7-(tert-butyl)fluorenyl | methyl-fluoranthenyl |
| 1511 | H— | CH₃— | CH₃— | methyl-fluoranthenyl |
| 1512 | CH₃— | CH₃— | CH₃— | methyl-fluoranthenyl |

TABLE 26
| Compd. No. | R1 | R2 | R3 | Ar |
|---|---|---|---|---|
| 1513 | H— | C$_4$H$_9$— | C$_4$H$_9$— | 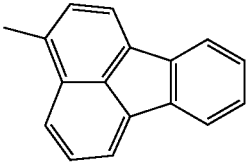 |
| 1514 | CH$_3$— | C$_4$H$_9$— | C$_4$H$_9$— | 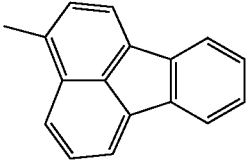 |
| 1515 | H— | 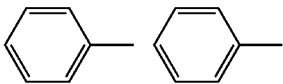 | 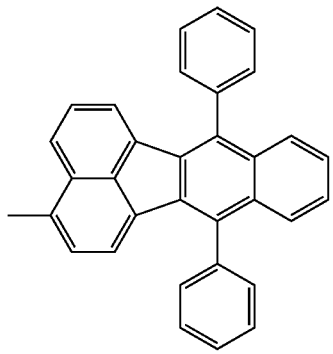 | 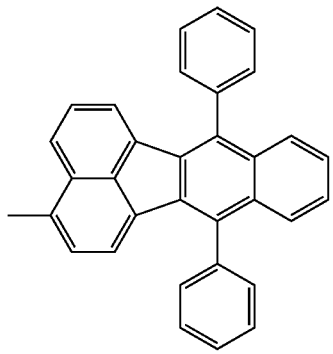 |
| 1516 | CH$_3$— | 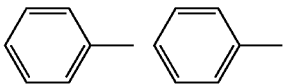 | 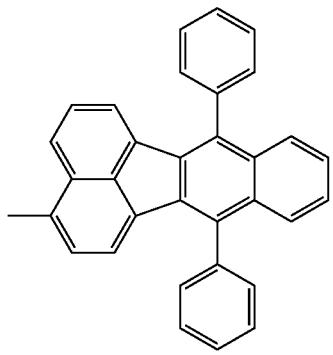 | 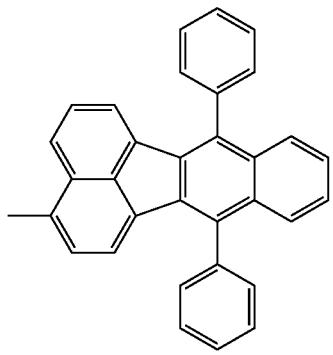 |
| 1517 | H— | 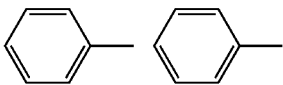 | 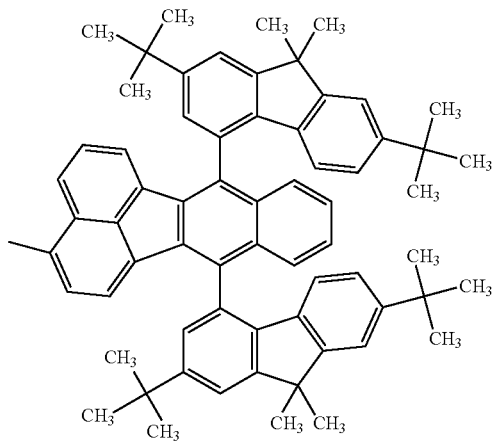 | 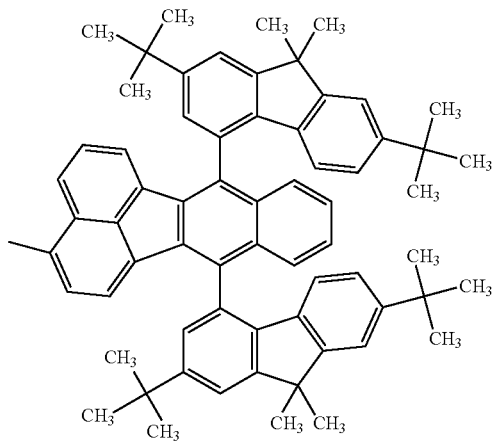 |

TABLE 26-continued
| Compd. No. | R1 | R2 | R3 | Ar |
|---|---|---|---|---|
| 1518 | CH₃— | 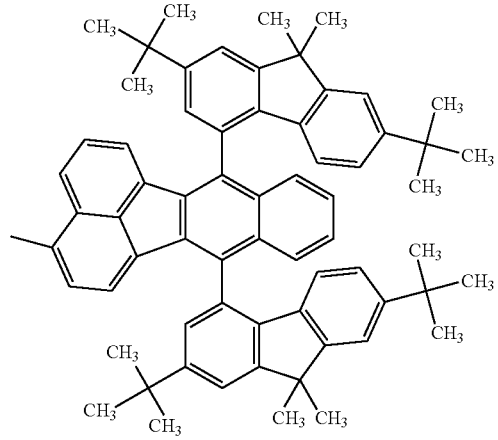 | 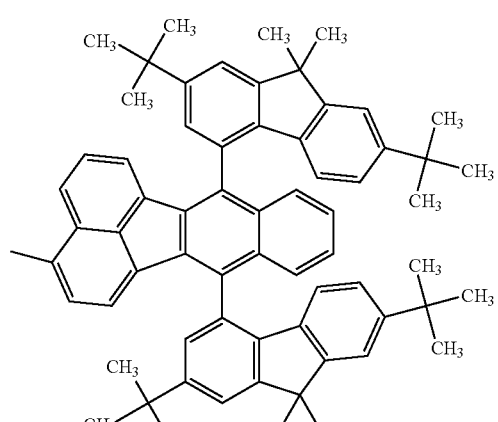 | |
| 1519 | H— | | CH₃— | |
TABLE 27
| Compd. No. | R1 | R2 | R3 | Ar |
|---|---|---|---|---|
| 1520 | CH₃— | | CH₃— | |
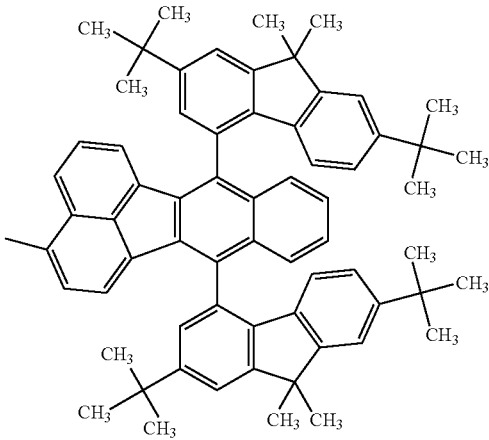

TABLE 27-continued

| Compd. No. | R1 | R2 | R3 | Ar |
|---|---|---|---|---|
| 1521 | H— | 9,9-dimethyl-2-fluorenyl (2-methyl) | 9,9-dimethyl-2-fluorenyl (2-methyl) | methyl-substituted diphenyl-fluoranthene |
| 1522 | CH₃— | 9,9-dimethyl-2-fluorenyl (2-methyl) | 9,9-dimethyl-2-fluorenyl (2-methyl) | methyl-substituted diphenyl-fluoranthene |
| 1523 | H— | 2,7-di-tert-butyl-4,9,9-trimethyl-fluorenyl | 2,7-di-tert-butyl-4,9,9-trimethyl-fluorenyl | methyl-substituted diphenyl-fluoranthene |
| 1524 | CH₃— | 2,7-di-tert-butyl-4,9,9-trimethyl-fluorenyl | 2,7-di-tert-butyl-4,9,9-trimethyl-fluorenyl | methyl-substituted diphenyl-fluoranthene |

TABLE 27-continued

| Compd. No. | R1 | R2 | R3 | Ar |
|---|---|---|---|---|
| 1525 | H— | CH₃— | CH₃— | |

TABLE 28

| Compd. No. | R1 | R2 | R3 | Ar |
|---|---|---|---|---|
| 1526 | CH₃— | CH₃— | CH₃— | |
| 1527 | H— | C₄H₉— | C₄H₉— | |
| 1528 | CH₃— | C₄H₉— | C₄H₉— | |

TABLE 28-continued

| Compd. No. | R1 | R2 | R3 | Ar |
|---|---|---|---|---|
| 1529 | H— | phenyl | phenyl | (two fused polycyclic structures) |
| 1530 | CH₃— | phenyl | p-tolyl | (two fused polycyclic structures) |

TABLE 29

| Compd. No. | R1 | R2 | R3 | Ar |
|---|---|---|---|---|
| 1531 | CH₃— | phenyl | phenyl | (acenaphthylene-fused phenyl-methyl-isoquinoline structure, two units) |
| 1532 | H— | phenyl | phenyl | methylpyrene |
| 1533 | CH₃— | phenyl | phenyl | methylpyrene |
| 1534 | H— | phenyl | phenyl | methyl-tert-butylpyrene |

TABLE 29-continued

| Compd. No. | R1 | R2 | R3 | Ar |
|---|---|---|---|---|
| 1535 | CH$_3$— | phenyl | m-tolyl (phenyl) | 1-methyl-6-tert-butylpyrene |

TABLE 30

| Compd. No. | R1 | R2 | R3 | Ar |
|---|---|---|---|---|
| 1536 | H— | phenyl | phenyl | 2-naphthyl |
| 1537 | CH$_3$— | phenyl | phenyl | 2-naphthyl |
| 1538 | H— | 9,9-dimethyl-2-fluorenyl | 9,9-dimethyl-2-fluorenyl | 2-naphthyl |
| 1539 | CH$_3$— | 9,9-dimethyl-2-fluorenyl | 9,9-dimethyl-2-fluorenyl | 2-naphthyl |
| 1540 | H— | phenyl | phenyl | 1-naphthyl |
| 1541 | CH$_3$— | phenyl | phenyl | 1-naphthyl |
| 1542 | H— | 9,9-dimethyl-2-fluorenyl | 9,9-dimethyl-2-fluorenyl | 1-naphthyl |

TABLE 30-continued

| Compd. No. | R1 | R2 | R3 | Ar |
|---|---|---|---|---|
| 1543 | CH₃— | 9,9-dimethyl-2-fluorenyl | 9,9-dimethyl-2-fluorenyl | 1-naphthyl |
| 1544 | H— | phenyl | phenyl | 4,7-di-tert-butyl-1-naphthyl |
| 1545 | CH₃— | phenyl | phenyl | 4,7-di-tert-butyl-1-naphthyl |
| 1546 | H— | 9,9-dimethyl-2-fluorenyl | 9,9-dimethyl-2-fluorenyl | 4,7-di-tert-butyl-1-naphthyl |
| 1547 | CH₃— | 9,9-dimethyl-2-fluorenyl | 9,9-dimethyl-2-fluorenyl | 4,7-di-tert-butyl-1-naphthyl |

TABLE 31

| Compd. No. | R1 | R2 | R3 | Ar |
|---|---|---|---|---|
| 1548 | H— | phenyl | phenyl | 9,9-dimethylfluoren-2-yl |
| 1549 | CH₃— | phenyl | phenyl | 9,9-dimethylfluoren-2-yl |
| 1550 | H— | 9,9-dimethylfluoren-2-yl | 9,9-dimethylfluoren-2-yl | 9,9-dimethylfluoren-2-yl |
| 1551 | CH₃— | 9,9-dimethylfluoren-2-yl | 9,9-dimethylfluoren-2-yl | 9,9-dimethylfluoren-2-yl |
| 1552 | H— | phenyl | phenyl | 2,7-di-tert-butyl-4,9,9-trimethylfluoren-2-yl |
| 1553 | CH₃— | phenyl | phenyl | 2,7-di-tert-butyl-4,9,9-trimethylfluoren-2-yl |

TABLE 31-continued

| Compd. No. | R1 | R2 | R3 | Ar |
|---|---|---|---|---|
| 1554 | H— | 2-(9,9-dimethylfluorenyl) | 2-(9,9-dimethylfluorenyl) | 2,7-di-tert-butyl-4-methyl-9,9-dimethylfluorenyl |
| 1555 | CH₃— | 2-(9,9-dimethylfluorenyl) | 2-(9,9-dimethylfluorenyl) | 2,7-di-tert-butyl-4-methyl-9,9-dimethylfluorenyl |
| 1556 | H— | phenyl | phenyl | 9-phenanthryl |
| 1557 | CH₃— | phenyl | phenyl | 9-phenanthryl |

TABLE 32

| Compd. No. | R1 | R2 | R3 | Ar |
|---|---|---|---|---|
| 1558 | H— | 2-(9,9-dimethylfluorenyl) | 2-(9,9-dimethylfluorenyl) | 9-phenanthryl |

TABLE 32-continued

| Compd. No. | R1 | R2 | R3 | Ar |
|---|---|---|---|---|
| 1559 | CH₃— | 9,9-dimethyl-2-fluorenyl (methyl-substituted) | 9,9-dimethyl-2-fluorenyl (methyl-substituted) | methylphenanthrenyl |
| 1560 | H— | phenyl | phenyl | methylchrysenyl |
| 1561 | CH₃— | phenyl | phenyl | methylchrysenyl |
| 1562 | H— | 9,9-dimethyl-2-fluorenyl (methyl-substituted) | 9,9-dimethyl-2-fluorenyl (methyl-substituted) | methylchrysenyl |
| 1563 | CH₃— | 9,9-dimethyl-2-fluorenyl (methyl-substituted) | 9,9-dimethyl-2-fluorenyl (methyl-substituted) | methylphenanthrenyl |

Compound Example 7

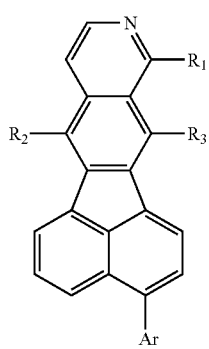

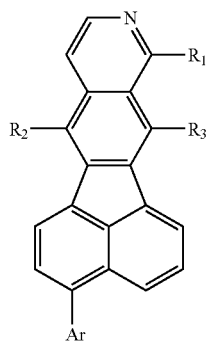

wherein:

[9] $R_1$ represents a hydrogen atom, or an alkyl group such as a methyl group or an ethyl group;

$R_2$ and $R_3$ each represent an aryl group such as a phenyl group, a fused polycyclic aromatic group with three or less rings such as a fluorenyl group, or an alkyl group such as a methyl group; and

[10] Ar represents a substituted amino group such as a diphenylamino group.

When $R_2$ and $R_3$ are different from each other, $R_2$ and $R_3$ shown in the following tables may be replaced with each other.

TABLE 33

| Compd. No. | R1 | R2 | R3 | Ar |
|---|---|---|---|---|
| 1601 | H— | Ph— | Ph— | Ph₂N— |
| 1602 | CH₃— | Ph— | Ph— | Ph₂N— |
| 1603 | H— | Ph— | CH₃— | Ph₂N— |

TABLE 33-continued
| Compd. No. | R1 | R2 | R3 | Ar |
|---|---|---|---|---|
| 1604 | CH₃— | 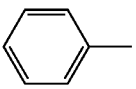 | CH₃— | 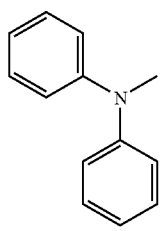 |
| 1605 | H— | 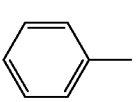 | C₄H₉— | 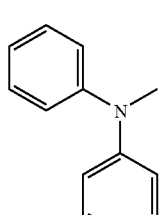 |
| 1606 | CH₃— | 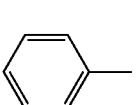 | C₄H₉— | 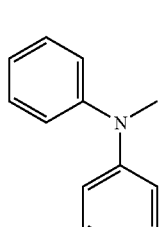 |
| 1607 | H— | CH₃— | CH₃— | 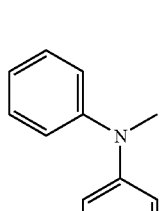 |
| 1608 | CH₃— | CH₃— | CH₃— | 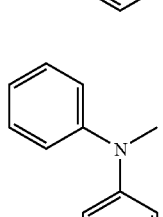 |
| 1609 | H— | C₄H₉— | C₄H₉— | 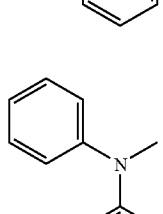 |

TABLE 33-continued

| Compd. No. | R1 | R2 | R3 | Ar |
|---|---|---|---|---|
| 1610 | CH₃— | C₄H₉— | C₄H₉— | -N(C₆H₅)₂ |

TABLE 34

| Compd. No. | R1 | R2 | R3 | Ar |
|---|---|---|---|---|
| 1611 | H— | phenyl | 9,9-dimethylfluoren-2-yl | -N(C₆H₅)₂ |
| 1612 | CH₃— | phenyl | 9,9-dimethylfluoren-2-yl | -N(C₆H₅)₂ |
| 1613 | H— | 9,9-dimethylfluoren-2-yl | 9,9-dimethylfluoren-2-yl | -N(C₆H₅)₂ |
| 1614 | CH₃— | 9,9-dimethylfluoren-2-yl | 9,9-dimethylfluoren-2-yl | -N(C₆H₅)₂ |
| 1615 | H— | 9,9-dimethylfluoren-2-yl | CH₃— | -N(C₆H₅)₂ |

TABLE 34-continued

| Compd. No. | R1 | R2 | R3 | Ar |
|---|---|---|---|---|
| 1616 | CH₃— | 9,9-dimethyl-2-fluorenyl | CH₃— | N,N-diphenylamino |
| 1617 | H— | 9,9-dimethyl-2-fluorenyl | C₄H₉— | N,N-diphenylamino |
| 1618 | CH₃— | 9,9-dimethyl-2-fluorenyl | C₄H₉— | N,N-diphenylamino |
| 1619 | H— | 9,9-dimethyl-2-fluorenyl | 9,9-dimethyl-2-fluorenyl | 9-carbazolyl |
| 1620 | CH₃— | 9,9-dimethyl-2-fluorenyl | 9,9-dimethyl-2-fluorenyl | 9-carbazolyl |
| 1621 | H— | 9,9-dimethyl-2-fluorenyl | CH₃— | 9-carbazolyl |

TABLE 35

| Compd. No. | R1 | R2 | R3 | Ar |
|---|---|---|---|---|
| 1622 | CH₃— | 9,9-dimethyl-2-fluorenyl | CH₃— | 9-carbazolyl |

TABLE 35-continued
| Compd. No. | R1 | R2 | R3 | Ar |
|---|---|---|---|---|
| 1623 | H— | 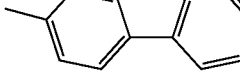 | C$_4$H$_9$— | 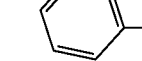 |
| 1624 | CH$_3$— | 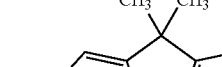 | C$_4$H$_9$— |  |
| 1625 | H— | 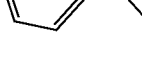 |  | 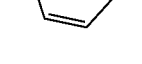 |
| 1626 | CH$_3$— | 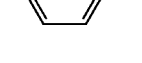 | 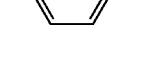 | 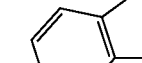 |
| 1627 | H— | 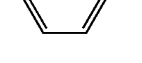 | CH$_3$— | 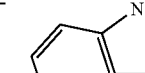 |
| 1628 | CH$_3$— | 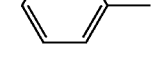 | CH$_3$— | 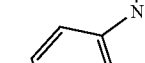 |
| 1629 | H— | 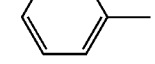 | C$_4$H$_9$— | 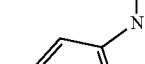 |
| 1630 | CH$_3$— | 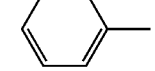 | C$_4$H$_9$— |  |
| 1631 | H— | CH$_3$— | CH$_3$— |  |

TABLE 35-continued

| Compd. No. | R1 | R2 | R3 | Ar |
|---|---|---|---|---|
| 1632 | CH$_3$— | CH$_3$— | CH$_3$— | 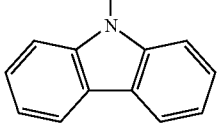 |
| 1633 | H— | C$_4$H$_9$— | C$_4$H$_9$— | 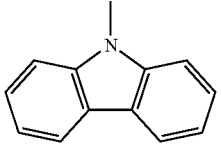 |
| 1634 | CH$_3$— | C$_4$H$_9$— | C$_4$H$_9$— | 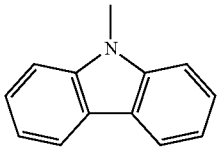 |
| 1635 | H— | 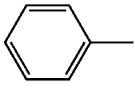 | 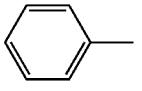 | 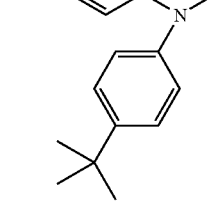 |
| 1636 | H— | 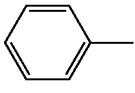 | 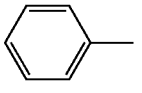 | 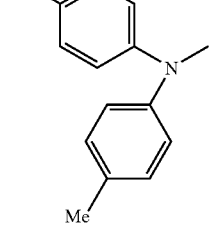 |

Compound Example 8

[11]

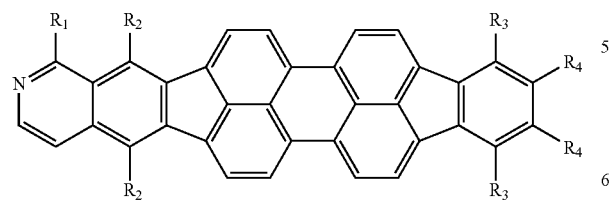

wherein:

R$_1$ represents a hydrogen atom, or an alkyl group such as a methyl group or an ethyl group;

R$_2$ represents an aryl group such as a phenyl group or a tolyl group, or a fused polycyclic aromatic group with three or less rings such as a fluorenyl group; and R$_3$ and R$_4$ each represent a hydrogen atom, or an alkyl group such as a methyl group.

TABLE 36

| Compd. No. | R1 | R2 | R3 | R4 |
|---|---|---|---|---|
| 1701 | H— | 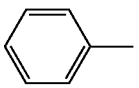 | H— | H— |
| 1702 | CH$_3$— | 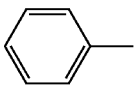 | H— | H— |

TABLE 36-continued

| Compd. No. | R1 | R2 | R3 | R4 |
|---|---|---|---|---|
| 1703 | H— | phenyl | CH₃— | CH₃— |
| 1704 | CH₃— | phenyl | CH₃— | CH₃— |
| 1705 | H— | phenyl | CH₃— | C₂H₅— |
| 1706 | CH₃— | phenyl | CH₃— | C₂H₅— |
| 1707 | H— | phenyl | CH₃— | H— |
| 1708 | CH₃— | phenyl | CH₃— | H— |
| 1709 | H— | 4-methylphenyl | H— | H— |
| 1710 | CH₃— | 4-methylphenyl | H— | H— |
| 1711 | H— | 4-methylphenyl | CH₃— | H— |
| 1712 | CH₃— | 4-methylphenyl | CH₃— | H— |
| 1713 | H— | 4-methylphenyl | C₂H₅— | H— |
| 1714 | CH₃— | 4-methylphenyl | C₂H₅— | H— |
| 1715 | H— | naphthyl | H— | H— |
| 1716 | CH₃— | naphthyl | H— | H— |
| 1717 | H— | naphthyl | CH₃— | H— |
| 1718 | CH₃— | naphthyl | CH₃— | H— |
| 1719 | H— | naphthyl | C₂H₅— | H— |
| 1720 | CH₃— | naphthyl | C₂H₅— | H— |
| 1721 | H— | 9,9-dimethylfluorenyl | H— | H— |
| 1722 | CH₃— | 9,9-dimethylfluorenyl | H— | H— |
| 1723 | H— | 9,9-dimethylfluorenyl | CH₃— | H— |

TABLE 37

| Compd. No. | R1 | R2 | R3 | R4 |
|---|---|---|---|---|
| 1724 | CH₃— | 9,9-dimethylfluorenyl | CH₃— | H— |
| 1725 | H— | 9,9-dimethylfluorenyl | C₂H₅— | H— |
| 1726 | CH₃— | 9,9-dimethylfluorenyl | C₂H₅— | H— |

TABLE 37-continued

| Compd. No. | R1 | R2 | R3 | R4 |
| --- | --- | --- | --- | --- |
| 1727 | H— | 2-methyl-9,9-dimethylfluorenyl | CH₃— | CH₃— |
| 1728 | CH₃— | 2-methyl-9,9-dimethylfluorenyl | CH₃— | CH₃— |
| 1729 | H— | 2-methyl-9,9-dimethylfluorenyl | C₂H₅— | C₂H₅— |
| 1730 | CH₃— | 2-methyl-9,9-dimethylfluorenyl | C₂H₅— | C₂H₅— |
| 1731 | H— | 2,7-di-tert-butyl-4-methyl-9,9-dimethylfluorenyl | H— | H— |
| 1732 | CH₃— | 2,7-di-tert-butyl-4-methyl-9,9-dimethylfluorenyl | H— | H— |

TABLE 37-continued

| Compd. No. | R1 | R2 | R3 | R4 |
| --- | --- | --- | --- | --- |
| 1733 | H— | 2,7-di-tert-butyl-4-methyl-9,9-dimethylfluorenyl | CH₃— | H— |

TABLE 38

| Compd. No. | R1 | R2 | R3 | R4 |
| --- | --- | --- | --- | --- |
| 1734 | CH₃— | 2,7-di-tert-butyl-4-methyl-9,9-dimethylfluorenyl | CH₃— | H— |
| 1735 | H— | 2,7-di-tert-butyl-4-methyl-9,9-dimethylfluorenyl | CH₃— | CH₃— |

TABLE 38-continued

| Compd. No. | R1 | R2 | R3 | R4 |
|---|---|---|---|---|
| 1736 | CH₃— | 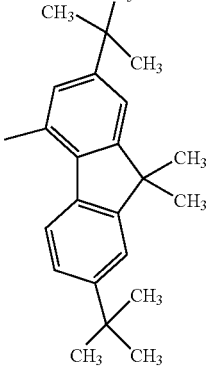 | CH₃— | CH₃— |

Compound Example 9

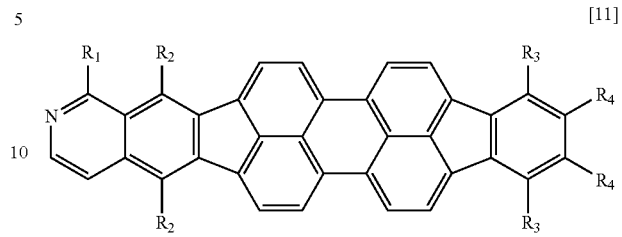

[11]

wherein:
$R_1$ represents a hydrogen atom, or an alkyl group such as a methyl group or an ethyl group;
$R_2$ and $R_3$ represent each an aryl group such as a phenyl group or a tolyl group, or a fused polycyclic aromatic group with three or less rings such as a fluorenyl group; and
$R_4$ represents a hydrogen atom, or an alkyl group such as a methyl group.

TABLE 39

| Compd. No. | R1 | R2 | R3 | R4 |
|---|---|---|---|---|
| 1801 | H— | phenyl | phenyl | H— |
| 1802 | CH₃— | phenyl | phenyl | H— |
| 1803 | H— | phenyl | phenyl | CH₃— |
| 1804 | CH₃— | phenyl | phenyl | CH₃— |
| 1805 | H— | phenyl | phenyl | C₂H₅— |
| 1806 | CH₃— | phenyl | phenyl | C₂H₅— |
| 1807 | H— | 4-methylphenyl | 4-methylphenyl | H— |
| 1808 | CH₃— | 4-methylphenyl | phenyl | H— |
| 1809 | H— | 4-methylbiphenyl | 4-methylphenyl | H— |
| 1810 | CH₃— | 4-methylbiphenyl | 4-methylphenyl | H— |

TABLE 39-continued

| Compd. No. | R1 | R2 | R3 | R4 |
|---|---|---|---|---|
| 1811 | H— | 4-CH₃-C₆H₄— | 4-CH₃-C₆H₄— | CH₃— |
| 1812 | CH₃— | 4-CH₃-C₆H₄— | 4-CH₃-C₆H₄— | CH₃— |
| 1813 | H— | 4-CH₃-C₆H₄— | 4-CH₃-C₆H₄— | C₂H₅— |
| 1814 | CH₃— | 4-CH₃-C₆H₄— | 4-CH₃-C₆H₄— | C₂H₅— |
| 1815 | H— | 2-naphthyl | C₆H₅— | H— |
| 1816 | CH₃— | 2-naphthyl | C₆H₅— | H— |
| 1817 | H— | 2-naphthyl | C₆H₅— | CH₃— |
| 1818 | CH₃— | 2-naphthyl | C₆H₅— | CH₃— |
| 1819 | H— | 2-naphthyl | C₆H₅— | C₂H₅— |
| 1820 | CH₃— | 2-naphthyl | C₆H₅— | C₂H₅— |
| 1821 | H— | C₆H₅— | C₆H₅— | H— |
| 1822 | H— | C₆H₅— | C₆H₅— | H— |
| 1823 | H— | C₆H₅— | C₆H₅— | H— |
| 1824 | H— | 4-CH₃-C₆H₄— | C₆H₅— | H— |
| 1825 | H— | 4-CH₃-C₆H₄— | C₆H₅— | H— |

Compound Example 10

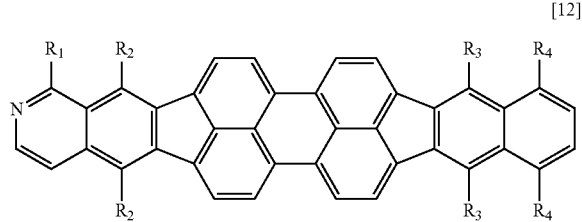

wherein:

R₁ represents a hydrogen atom, or an alkyl group such as a methyl group or an ethyl group;

R₂ and R₃ each represent an aryl group such as a phenyl group or a tolyl group, or a fused polycyclic aromatic group with three or less rings such as a fluorenyl group; and R₄ represents a hydrogen atom, or an alkyl group such as a methyl group.

TABLE 40

| Compd. No. | R1 | R2 | R3 | R4 |
|---|---|---|---|---|
| 1901 | H— | phenyl | phenyl | H— |
| 1902 | CH₃— | phenyl | phenyl | H— |
| 1903 | H— | phenyl | phenyl | CH₃— |
| 1904 | CH₃— | phenyl | phenyl | CH₃— |
| 1905 | H— | phenyl | phenyl | C₂H₅— |
| 1906 | CH₃— | phenyl | phenyl | C₂H₅— |
| 1907 | H— | phenyl | 4-CH₃-phenyl | H— |
| 1908 | CH₃— | phenyl | 4-CH₃-phenyl | H— |
| 1909 | H— | phenyl | 4-CH₃-phenyl | CH₃— |
| 1910 | CH₃— | phenyl | 4-CH₃-phenyl | CH₃— |
| 1911 | H— | 4-CH₃-phenyl | phenyl | H— |
| 1912 | CH₃— | 4-CH₃-phenyl | phenyl | H— |

TABLE 40-continued
| Compd. No. | R1 | R2 | R3 | R4 |
|---|---|---|---|---|
| 1913 | H— | 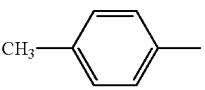 | 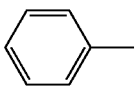 | CH₃— |
| 1914 | CH₃— | 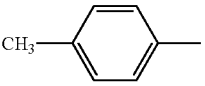 | 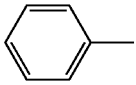 | CH₃— |
| 1915 | H— | 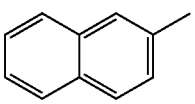 | 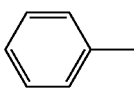 | H— |
| 1916 | CH₃— | 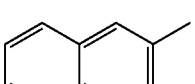 | 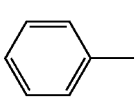 | H— |
| 1917 | H— | 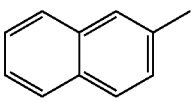 | 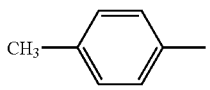 | H— |
| 1918 | CH₃— | 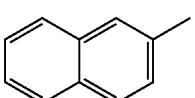 | 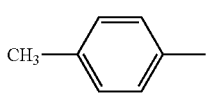 | H— |
| 1919 | H— | 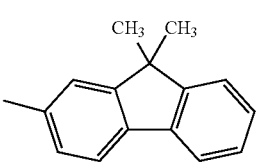 | 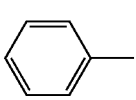 | H— |
| 1920 | CH₃— | 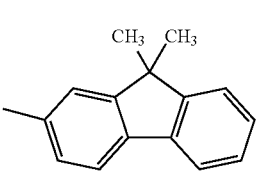 | 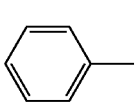 | H— |
| 1921 | H— | 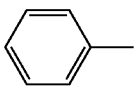 | 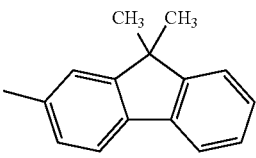 | H— |
| 1922 | CH₃— | 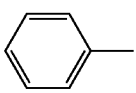 | 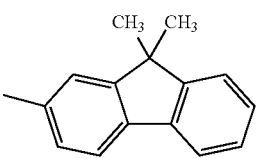 | H— |

TABLE 41
| Compd. No. | R1 | R2 | R3 | R4 |
|---|---|---|---|---|
| 1923 | H— | 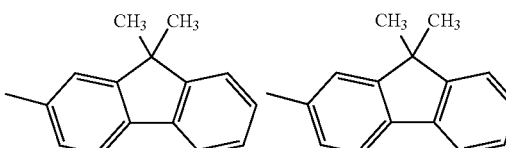 | 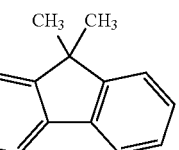 | H— |
| 1924 | CH₃— | 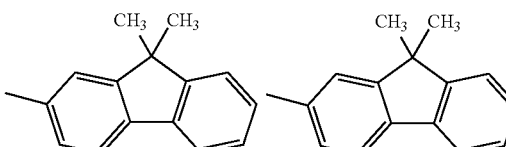 | 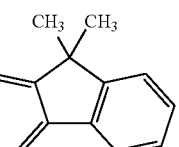 | H— |
| 1925 | H— | 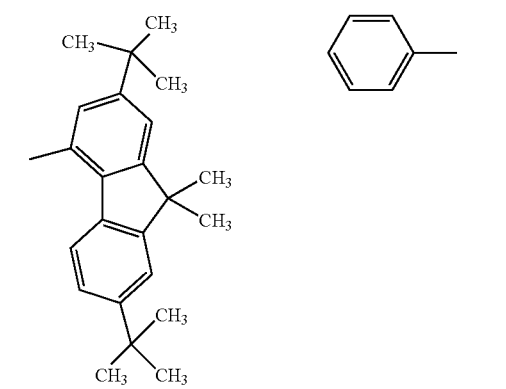 | 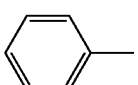 | H— |
| 1926 | CH₃— | 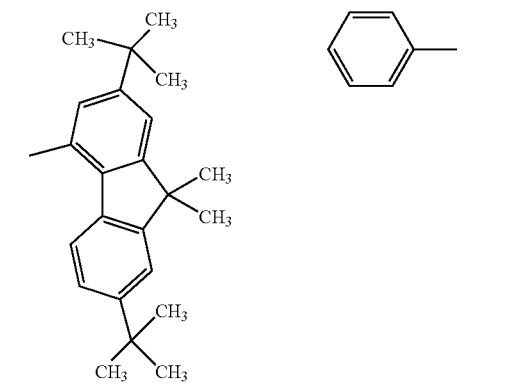 | 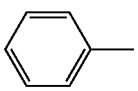 | H— |
| 1927 | H— | 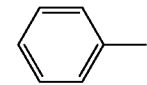 | 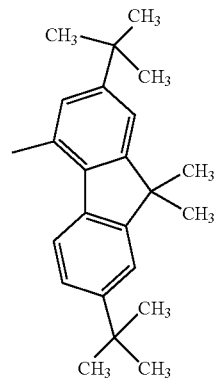 | H— |

TABLE 41-continued

| Compd. No. | R1 | R2 | R3 | R4 |
|---|---|---|---|---|
| 1928 | CH₃— | phenyl | di-tert-butyl-methyl-dimethylfluorenyl | H— |
| 1929 | H— | di-tert-butyl-methyl-dimethylfluorenyl | di-tert-butyl-methyl-dimethylfluorenyl | H— |
| 1930 | CH₃— | di-tert-butyl-methyl-dimethylfluorenyl | di-tert-butyl-methyl-dimethylfluorenyl | H— |

Compound Example 11

[12]

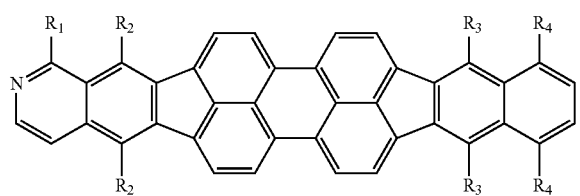

wherein:

$R_1$ represents a hydrogen atom, or an alkyl group such as a methyl group or an ethyl group;

$R_2$ represents an aryl group such as a phenyl group or a tolyl group, or a fused polycyclic aromatic group with three or less rings such as a fluorenyl group; and $R_3$ and $R_4$ each represent a hydrogen atom, or an alkyl group such as a methyl group.

TABLE 42

| Compd. No. | R1 | R2 | R3 | R4 |
|---|---|---|---|---|
| 2001 | H— | phenyl | CH₃— | H— |

TABLE 42-continued

| Compd. No. | R1 | R2 | R3 | R4 |
|---|---|---|---|---|
| 2002 | CH₃— | phenyl | CH₃— | H— |
| 2003 | H— | phenyl | CH₃— | CH₃— |
| 2004 | CH₃— | phenyl | CH₃— | CH₃— |
| 2005 | H— | phenyl | CH₃— | C₂H₅— |
| 2006 | CH₃— | phenyl | CH₃— | C₂H₅— |
| 2007 | H— | phenyl | H— | H— |
| 2008 | CH₃— | phenyl | H— | H— |
| 2009 | H— | phenyl | H— | CH₃— |
| 2010 | CH₃— | phenyl | H— | CH₃— |
| 2011 | H— | phenyl | H— | C₂H₅— |
| 2012 | CH₃— | phenyl | H— | C₂H₅— |
| 2013 | H— | 4-(CH₃)-phenyl | H— | H— |
| 2014 | CH₃— | 4-(CH₃)-phenyl | H— | H— |
| 2015 | H— | 4-(CH₃)-phenyl | H— | CH₃— |
| 2016 | CH₃— | 4-(CH₃)-phenyl | H— | CH₃— |
| 2017 | H— | 4-(CH₃)-phenyl | CH₃— | H— |
| 2018 | CH₃— | 4-(CH₃)-phenyl | CH₃— | H— |
| 2019 | H— | 4-(CH₃)-phenyl | CH₃— | CH₃— |
| 2020 | CH₃— | 4-(CH₃)-phenyl | CH₃— | CH₃— |
| 2021 | H— | naphthyl | CH₃— | H— |
| 2022 | CH₃— | naphthyl | CH₃— | H— |
| 2023 | H— | naphthyl | CH₃— | CH₃— |
| 2024 | CH₃— | naphthyl | CH₃— | CH₃— |
| 2025 | H— | naphthyl | H— | H— |

TABLE 43

| Compd. No. | R1 | R2 | R3 | R4 |
|---|---|---|---|---|
| 2026 | CH₃— | naphthyl | H— | H— |
| 2027 | H— | naphthyl | H— | CH₃— |
| 2028 | CH₃— | naphthyl | H— | CH₃— |
| 2029 | H— | 9,9-dimethylfluorenyl | H— | H— |

TABLE 43-continued

| Compd. No. | R1 | R2 | R3 | R4 |
|---|---|---|---|---|
| 2030 | CH₃— | 9,9-dimethyl-2-methylfluoren-7-yl | H— | H— |
| 2031 | H— | 9,9-dimethyl-2-methylfluoren-7-yl | H— | CH₃— |
| 2032 | CH₃— | 9,9-dimethyl-2-methylfluoren-7-yl | H— | CH₃— |
| 2033 | H— | 9,9-dimethyl-2-methylfluoren-7-yl | CH₃— | H— |
| 2034 | CH₃— | 9,9-dimethyl-2-methylfluoren-7-yl | CH₃— | H— |
| 2035 | H— | 9,9-dimethyl-2-methylfluoren-7-yl | CH₃— | CH₃— |
| 2036 | CH₃— | 9,9-dimethyl-2-methylfluoren-7-yl | CH₃— | CH₃— |
| 2037 | H— | 2,9,9-trimethyl-7-tert-butylfluoren-4-yl (with t-Bu substituent) | CH₃— | H— |
| 2038 | CH₃— | 9,9-dimethyl-2,7-di-tert-butyl-4-methylfluorenyl | CH₃— | H— |

TABLE 44

| Compd. No. | R1 | R2 | R3 | R4 |
|---|---|---|---|---|
| 2039 | H— | 9,9-dimethyl-2,7-di-tert-butyl-4-methylfluorenyl | H— | H— |
| 2040 | CH₃— | 9,9-dimethyl-2,7-di-tert-butyl-4-methylfluorenyl | H— | H— |

Compound Example 12

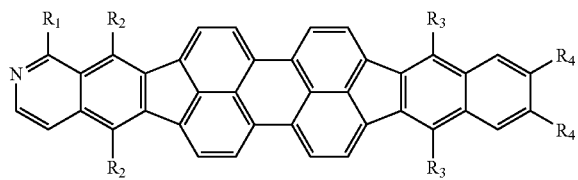

wherein:

[13]

R₁ represents a hydrogen atom, or an alkyl group such as a methyl group or an ethyl group; and R₂ to R₄ each represent an aryl group such as a phenyl group or a tolyl group, or a fused polycyclic aromatic group with three or less rings such as a fluorenyl group.

TABLE 45

| Compd. No. | R1 | R2 | R3 | R4 |
|---|---|---|---|---|
| 2101 | H— | phenyl | phenyl | phenyl |
| 2102 | CH₃— | phenyl | phenyl | phenyl |
| 2103 | H— | phenyl | 4-methylphenyl | phenyl |
| 2104 | CH₃— | phenyl | 4-methylphenyl | phenyl |
| 2105 | H— | phenyl | 4-methylphenyl | 4-methylphenyl |
| 2106 | CH₃— | phenyl | 4-methylphenyl | 4-methylphenyl |
| 2107 | H— | 4-methylphenyl | 4-methylphenyl | 4-methylphenyl |
| 2108 | CH₃— | 4-methylphenyl | 4-methylphenyl | 4-methylphenyl |
| 2109 | H— | 4-methylphenyl | phenyl | phenyl |
| 2110 | CH₃— | 4-methylphenyl | phenyl | phenyl |
| 2111 | H— | 4-methylphenyl | phenyl | 4-methylphenyl |
| 2112 | CH₃— | 4-methylphenyl | phenyl | 4-methylphenyl |

TABLE 45-continued
| Compd. No. | R1 | R2 | R3 | R4 |
|---|---|---|---|---|
| 2113 | H— | 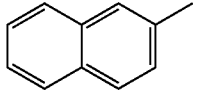 | 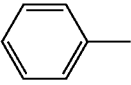 | 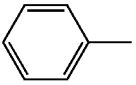 |
| 2114 | CH₃— | 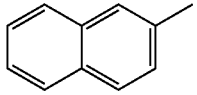 | 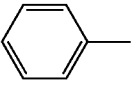 | 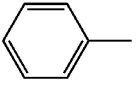 |
| 2115 | H— | 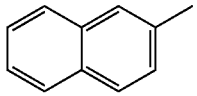 | 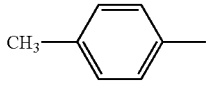 | 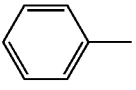 |
| 2116 | CH₃— | 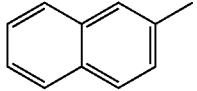 | 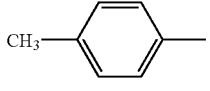 | 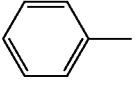 |
| 2117 | H— | 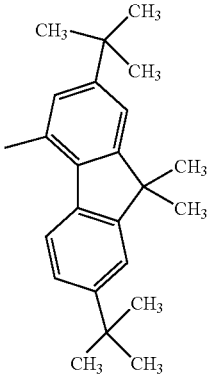 | 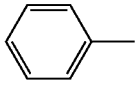 | 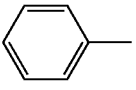 |
TABLE 46
| Compd. No. | R1 | R2 | R3 | R4 |
|---|---|---|---|---|
| 2118 | CH₃— | 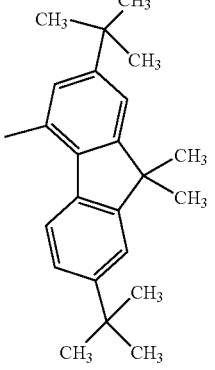 | 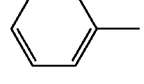 | 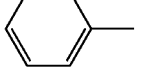 |

TABLE 46-continued

| Compd. No. | R1 | R2 | R3 | R4 |
|---|---|---|---|---|
| 2119 | H— | phenyl | 2,7-di-tert-butyl-4-methyl-9,9-dimethylfluorenyl | phenyl |
| 2120 | CH₃— | phenyl | 2,7-di-tert-butyl-4-methyl-9,9-dimethylfluorenyl | phenyl |

Compound Example 13

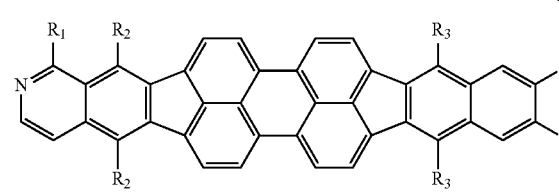

[13]

wherein:
R₁ represents a hydrogen atom, or an alkyl group such as a methyl group or an ethyl group;
R₂ represents an aryl group such as a phenyl group or a tolyl group, or a fused polycyclic aromatic group with three or less rings such as a fluorenyl group; and
R₃ and R₄ each represent an alkyl group such as a methyl group.

TABLE 47

| Compd. No. | R1 | R2 | R3 | R4 |
|---|---|---|---|---|
| 2201 | H— | phenyl | CH₃— | CH₃— |
| 2202 | CH₃— | phenyl | CH₃— | CH₃— |
| 2203 | H— | phenyl | CH₃— | C₂H₅— |
| 2204 | CH₃— | phenyl | CH₃— | C₂H₅— |
| 2205 | H— | 4-methylphenyl | CH₃— | CH₃— |
| 2206 | CH₃— | 4-methylphenyl | CH₃— | CH₃— |
| 2207 | H— | naphthyl | CH₃— | CH₃— |

TABLE 47-continued

| Compd. No. | R1 | R2 | R3 | R4 |
|---|---|---|---|---|
| 2208 | CH₃— | 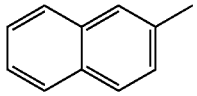 | CH₃— | CH₃— |
| 2209 | H— | 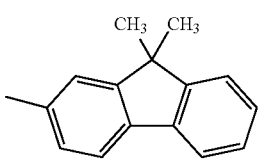 | CH₃— | CH₃— |
| 2210 | CH₃— | 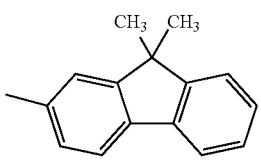 | CH₃— | CH₃— |
| 2211 | H— | 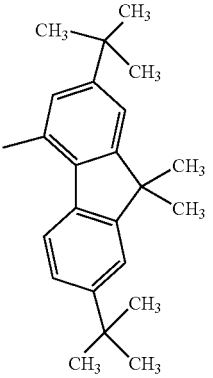 | CH₃— | CH₃— |
| 2212 | CH₃— | 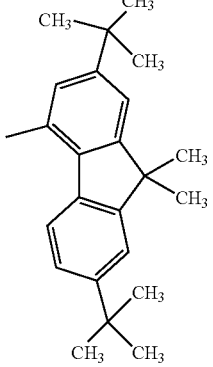 | CH₃— | CH₃— |

Compound Example 14

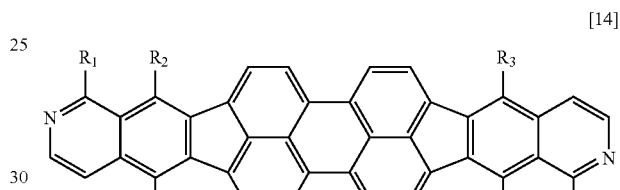

[14]

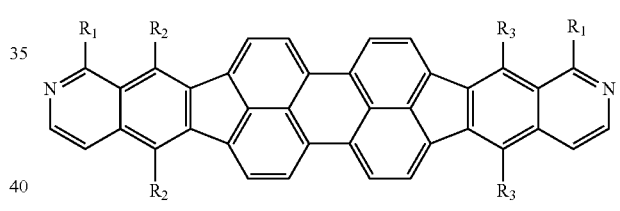

[15]

wherein:
R₁, represents a hydrogen atom, or an alkyl group such as a methyl group;
R₂ and R₃ each represent an aryl group such as a phenyl group or a tolyl group, a fused polycyclic aromatic group with three or less rings such as a fluorenyl group, or an alkyl group such as a methyl group.

TABLE 48

| Compd. No. | R1 | R2 | R3 |
|---|---|---|---|
| 2301 | H— | 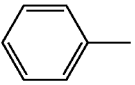 | 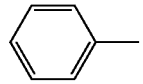 |
| 2302 | CH₃— | 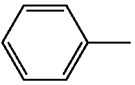 | 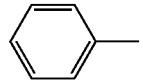 |
| 2303 | H— | 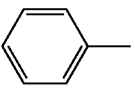 | CH₃— |

TABLE 48-continued
| Compd. No. | R1 | R2 | R3 |
|---|---|---|---|
| 2304 | CH₃— | 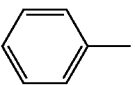 | CH₃— |
| 2305 | H— | 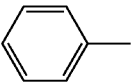 | C₄H₉— |
| 2306 | CH₃— | 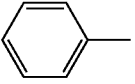 | C₄H₉— |
| 2307 | H— | 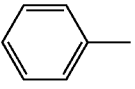 | 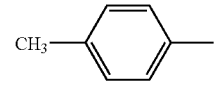 |
| 2308 | CH₃— | 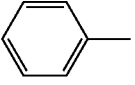 | 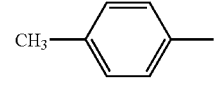 |
| 2309 | H— | 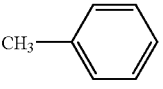 | 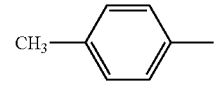 |
| 2310 | CH₃— | 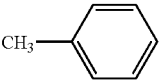 | 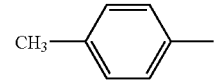 |
| 2311 | H— | 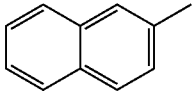 | 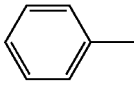 |
| 2312 | CH₃— | 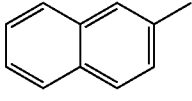 | 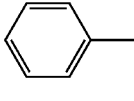 |
| 2313 | H— | 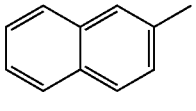 | 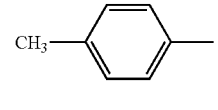 |
| 2314 | CH₃— | 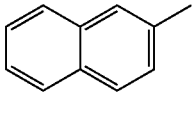 | 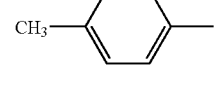 |
| 2315 | H— | 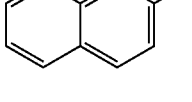 | 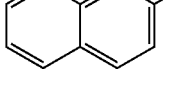 |
| 2316 | CH₃— | 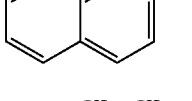 | 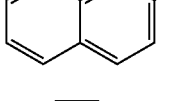 |
| 2317 | H— | 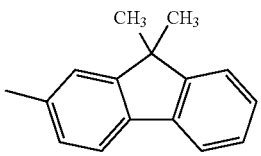 | 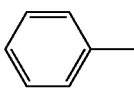 |

TABLE 48-continued

| Compd. No. | R1 | R2 | R3 |
|---|---|---|---|
| 2318 | CH₃— | 2,9,9-trimethylfluorenyl | tolyl |
| 2319 | H— | 2,9,9-trimethylfluorenyl | CH₃— |
| 2320 | CH₃— | 2,9,9-trimethylfluorenyl | CH₃— |
| 2321 | H— | 2,9,9-trimethylfluorenyl | 2,9,9-trimethylfluorenyl |

TABLE 49

| Compd. No. | R1 | R2 | R3 |
|---|---|---|---|
| 2322 | CH₃— | 2,9,9-trimethylfluorenyl | 2,9,9-trimethylfluorenyl |
| 2323 | H— | 2,7-di-tert-butyl-4,9,9-trimethylfluorenyl | phenyl |

TABLE 49-continued

| Compd. No. | R1 | R2 | R3 |
|---|---|---|---|
| 2324 | CH₃— | 2,7-di-tert-butyl-4,9,9-trimethylfluoren-3-yl | phenyl |
| 2325 | H— | 2,7-di-tert-butyl-4,9,9-trimethylfluoren-3-yl | 2,7-di-tert-butyl-4,9,9-trimethylfluoren-3-yl |
| 2326 | CH₃— | 2,7-di-tert-butyl-4,9,9-trimethylfluoren-3-yl | 2,7-di-tert-butyl-4,9,9-trimethylfluoren-3-yl |
| 2327 | H— | 2,7-di-tert-butyl-4,9,9-trimethylfluoren-3-yl | CH₃— |

TABLE 49-continued

| Compd. No. | R1 | R2 | R3 |
|---|---|---|---|
| 2328 | CH₃— | (fluorene with tert-butyl groups and methyl, gem-dimethyl) | CH₃— |

Compound Example 15

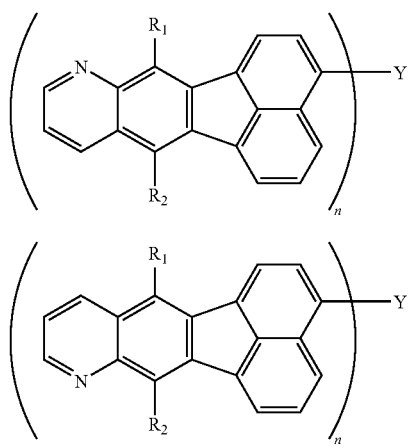

wherein:

[16] Y represents a linking group which is divalent or more such as a phenylene group or a biphenylene group; and

[17] $R_1$ and $R_2$ each represent an aryl group such as a phenyl group, a fused polycyclic aromatic group with three or less rings such as a fluorenyl group, or an alkyl group such as a methyl group or a butyl group.

When $R_1$ and $R_2$ are different from each other, $R_1$ and $R_2$ shown in the following tables may be replaced with each other.

TABLE 50

| Compd. No. | n | R1 | R2 | Y |
|---|---|---|---|---|
| 2401 | 2 | phenyl | phenyl | 1,4-phenylene |
| 2402 | 2 | phenyl | CH₃— | 1,4-phenylene |
| 2403 | 2 | phenyl | phenyl | 1,3-phenylene |
| 2404 | 2 | phenyl | CH₃— | 1,3-phenylene |

TABLE 50-continued
| Compd. No. | n | R1 | R2 | Y |
|---|---|---|---|---|
| 2405 | 2 | 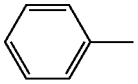 | 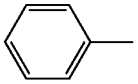 | 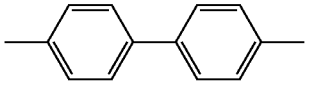 |
| 2406 | 2 | 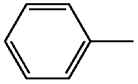 | CH₃— | 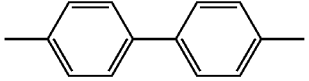 |
| 2407 | 2 | 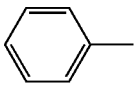 | 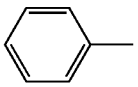 | 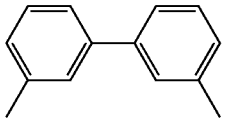 |
| 2408 | 2 | 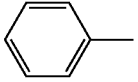 | CH₃— | 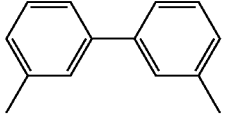 |
| 2409 | 2 | 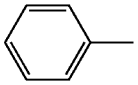 | 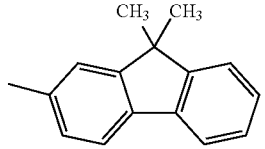 |  |
| 2410 | 2 | CH₃— | 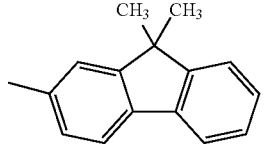 |  |
| 2411 | 2 | 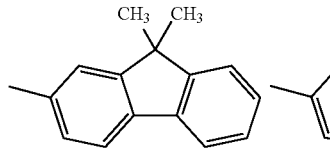 | 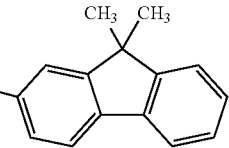 |  |
| 2412 | 2 | 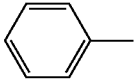 | 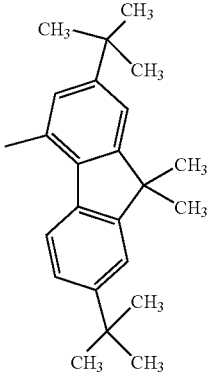 |  |

TABLE 51

| Compd. No. | n | R1 | R2 | Y |
|---|---|---|---|---|
| 2413 | 2 | CH₃— | (9,9-dimethyl-4-methyl-2,7-di-tert-butylfluorenyl) | (p-phenylene) |
| 2414 | 2 | (9,9-dimethyl-4-methyl-2,7-di-tert-butylfluorenyl) | (9,9-dimethyl-4-methyl-2,7-di-tert-butylfluorenyl) | (p-phenylene) |
| 2415 | 2 | (phenyl) | (9,9-dimethyl-2-fluorenyl) | (m-phenylene) |
| 2416 | 2 | CH₃— | (9,9-dimethyl-2-fluorenyl) | (m-phenylene) |
| 2417 | 2 | (9,9-dimethyl-2-fluorenyl) | (9,9-dimethyl-2-fluorenyl) | (m-phenylene) |

TABLE 51-continued
| Compd. No. | n | R1 | R2 | Y |
|---|---|---|---|---|
| 2418 | 2 | 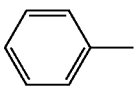 | 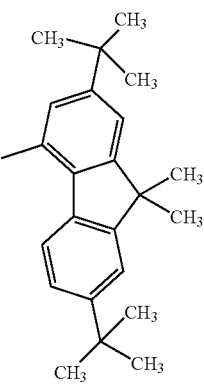 | 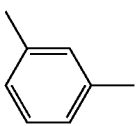 |
| 2419 | 2 | CH₃— | 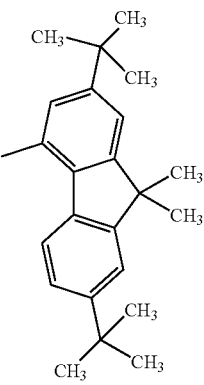 | 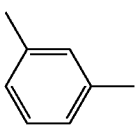 |
TABLE 52
| Compd. No. | n | R1 | R2 | Y |
|---|---|---|---|---|
| 2420 | 2 | 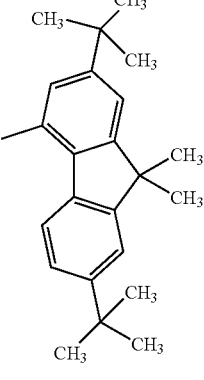 | 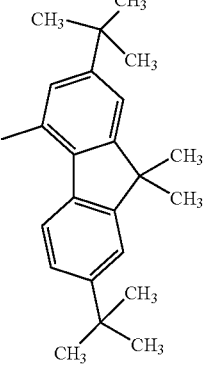 | 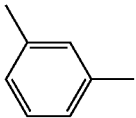 |
| 2421 | 2 | 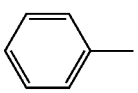 | 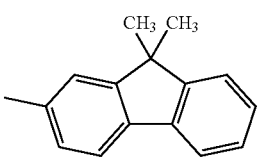 | 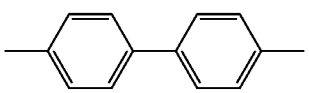 |

TABLE 52-continued

| Compd. No. | n | R1 | R2 | Y |
|---|---|---|---|---|
| 2422 | 2 | CH₃— | 2-methyl-9,9-dimethylfluorenyl | 4,4'-biphenylene |
| 2423 | 2 | 2-(9,9-dimethylfluorenyl), 7-methyl | 2-(9,9-dimethylfluorenyl), 7-methyl | 4,4'-biphenylene |
| 2424 | 2 | phenyl | 2,7-di-tert-butyl-4-methyl-9,9-dimethylfluorenyl | 4,4'-biphenylene |
| 2425 | 2 | CH₃— | 2,7-di-tert-butyl-4-methyl-9,9-dimethylfluorenyl | 4,4'-biphenylene |
| 2426 | 2 | 2,7-di-tert-butyl-4-methyl-9,9-dimethylfluorenyl | 2,7-di-tert-butyl-4-methyl-9,9-dimethylfluorenyl | 4,4'-biphenylene |

TABLE 53
| Compd.No. | n | R1 | R2 | Y |
|---|---|---|---|---|
| 2427 | 2 | 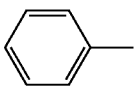 | 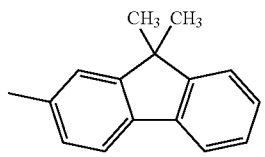 | 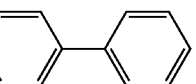 |
| 2428 | 2 | CH₃— | 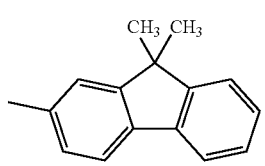 | 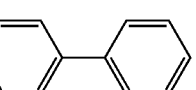 |
| 2429 | 2 | 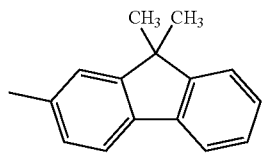 | 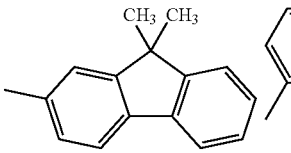 | 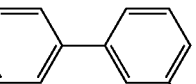 |
| 2430 | 2 | 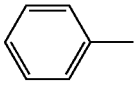 | 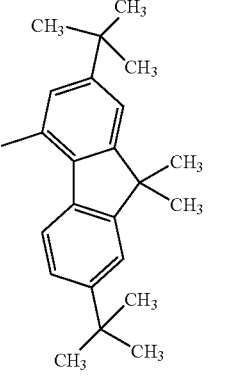 | 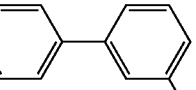 |
| 2431 | 2 | CH₃— | 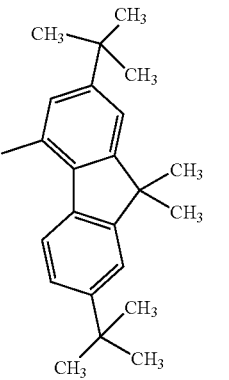 | 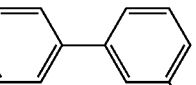 |

TABLE 53-continued

| Compd.No. | n | R1 | R2 | Y |
|---|---|---|---|---|
| 2432 | 2 | (structure) | (structure) | (structure) |

Compound Example 16

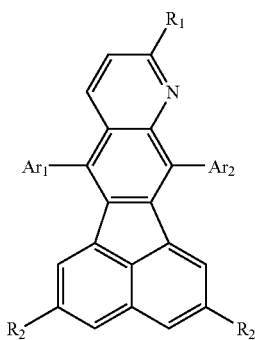

wherein:

[18]  $Ar_1$ and $Ar_2$ each represent an aryl group such as a phenyl group or a biphenyl group, or a fused polycyclic aromatic group with three or less rings such as a naphthyl group or a fluorenyl group; and $R_1$ and $R_2$ each represent a hydrogen atom, or an alkyl group such as a methyl group, an ethyl group, or a tertiary butyl group.

When $Ar_1$ and $Ar_2$ are different from each other, $Ar_1$ and $Ar_2$ shown in the following tables may be replaced with each other.

TABLE 54

| Compd. No. | Ar1 | Ar2 | R1 | R2 |
|---|---|---|---|---|
| 2501 | phenyl | phenyl | H— | H— |
| 2502 | phenyl | phenyl | CH₃— | H— |
| 2503 | phenyl | phenyl | H— | t-butyl |
| 2504 | phenyl | phenyl | CH₃— | t-butyl |
| 2505 | phenyl | methylfluorenyl | H— | H— |

TABLE 54-continued

| Compd. No. | Ar1 | Ar2 | R1 | R2 |
|---|---|---|---|---|
| 2506 | phenyl | 9,9-dimethyl-2-fluorenyl | CH₃— | H— |
| 2507 | phenyl | 9,9-dimethyl-2-fluorenyl | H— | tert-butyl |
| 2508 | phenyl | 2,7-di-tert-butyl-4,9,9-trimethyl-fluorenyl | H— | H— |
| 2509 | phenyl | 2,7-di-tert-butyl-4,9,9-trimethyl-fluorenyl | CH₃— | H— |
| 2510 | phenyl | 2,7-di-tert-butyl-4,9,9-trimethyl-fluorenyl | H— | tert-butyl |

TABLE 54-continued

| Compd. No. | Ar1 | Ar2 | R1 | R2 |
|---|---|---|---|---|
| 2511 | 9,9-dimethyl-2-fluorenyl (with methyl) | 9,9-dimethyl-2-fluorenyl (with methyl) | H— | H— |

TABLE 55

| Compd. No. | Ar1 | Ar2 | R1 | R2 |
|---|---|---|---|---|
| 2512 | 9,9-dimethyl-2-fluorenyl (with methyl) | 9,9-dimethyl-2-fluorenyl (with methyl) | CH$_3$— | H— |
| 2513 | 9,9-dimethyl-2-fluorenyl (with methyl) | 9,9-dimethyl-2-fluorenyl (with methyl) | H— | t-Bu |
| 2314 | 9,9-dimethyl-2-fluorenyl (with methyl) | 9,9-dimethyl-2-fluorenyl (with methyl) | CH$_3$— | t-Bu |
| 2315 | 9,9-dimethyl-fluorenyl (with t-Bu, methyl, t-Bu) | 9,9-dimethyl-fluorenyl (with t-Bu, methyl, t-Bu) | H— | H— |
| 2316 | 9,9-dimethyl-fluorenyl (with t-Bu, methyl, t-Bu) | 9,9-dimethyl-fluorenyl (with t-Bu, methyl, t-Bu) | CH$_3$— | H— |

TABLE 55-continued

| Compd. No. | Ar1 | Ar2 | R1 | R2 |
|---|---|---|---|---|
| 2517 | 2,7-di-tert-butyl-4,9,9-trimethylfluorenyl | 2,7-di-tert-butyl-4,9,9-trimethylfluorenyl | H— | tert-butyl |
| 2518 | phenyl | 2-naphthyl | H— | H— |
| 2519 | phenyl | 2-naphthyl | CH₃— | H— |
| 2520 | phenyl | 2-naphthyl | H— | tert-butyl |
| 2521 | 2-naphthyl | 2-naphthyl | H— | H— |
| 2522 | 2-naphthyl | 2-naphthyl | CH₃— | H— |
| 2523 | 2-naphthyl | 2-naphthyl | H— | tert-butyl |

Compound Example 17

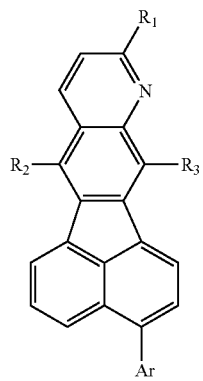

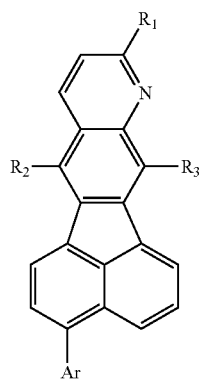

wherein:

R₁ represents a hydrogen atom, or an alkyl group such as a methyl group;

R₂ and R₃ each represent an aryl group such as a phenyl group or a biphenyl group, a fused polycyclic aromatic group with three or less rings such as a fluorenyl group, or an alkyl group such as a methyl group; and Ar represents a fused polycyclic aromatic group such as a fluoranthenyl group or a benzofluoranthenyl group.

When $R_2$ and $R_3$ are different from each other, $R_2$ and $R_3$ shown in the following tables may be replaced with each other.

TABLE 56

| Compd. No. | R1 | R2 | R3 | Ar |
|---|---|---|---|---|
| 2601 | H— | phenyl | phenyl | fluoranthenyl |
| 2602 | CH₃— | phenyl | phenyl | fluoranthenyl |
| 2603 | H— | phenyl | CH₃— | fluoranthenyl |
| 2604 | CH₃— | phenyl | CH₃— | fluoranthenyl |

TABLE 56-continued

| Compd. No. | R1 | R2 | R3 | Ar |
|---|---|---|---|---|
| 2605 | H— | 2,4,9,9-tetramethyl-7-tert-butyl-2-tert-butylfluorenyl group | 2,4,9,9-tetramethyl-7-tert-butyl-2-tert-butylfluorenyl group | methylfluoranthenyl |
| 2606 | CH₃— | 2,4,9,9-tetramethyl-7-tert-butyl-2-tert-butylfluorenyl group | 2,4,9,9-tetramethyl-7-tert-butyl-2-tert-butylfluorenyl group | methylfluoranthenyl |
| 2607 | H— | 2,7,9,9-tetramethylfluorenyl | 2,7,9,9-tetramethylfluorenyl | methylfluoranthenyl |
| 2608 | CH₃— | 2,7,9,9-tetramethylfluorenyl | 2,7,9,9-tetramethylfluorenyl | methylfluoranthenyl |
| 2609 | H— | CH₃— | CH₃— | methylfluoranthenyl |
| 2610 | CH₃— | CH₃— | CH₃— | methylfluoranthenyl |

TABLE 56-continued

| Compd. No. | R1 | R2 | R3 | Ar |
|---|---|---|---|---|
| 2611 | H— | phenyl | phenyl | (structure) |

TABLE 57

| Compd. No. | R1 | R2 | R3 | Ar |
|---|---|---|---|---|
| 2612 | CH₃— | phenyl | phenyl | (structure) |
| 2613 | H— | phenyl | CH₃— | (structure) |
| 2614 | CH₃— | phenyl | CH₃— | (structure) |

TABLE 57-continued

| Compd. No. | R1 | R2 | R3 | Ar |
|---|---|---|---|---|
| 2615 | H— | | | |
| 2616 | CH₃— | | | |
| 2617 | H— | | | |

TABLE 58
| Compd. No. | R1 | R2 | R3 | Ar |
|---|---|---|---|---|
| 2618 | CH₃— | 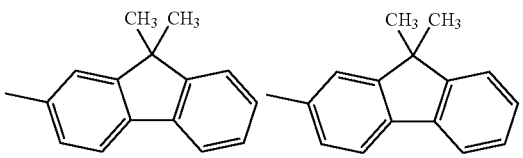 | 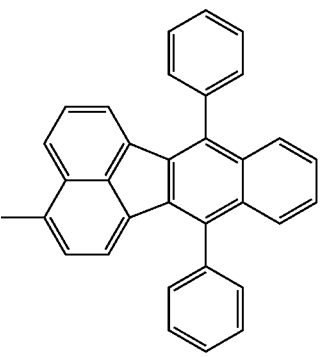 | 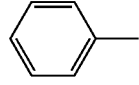 |
| 2619 | H— | 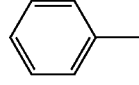 | 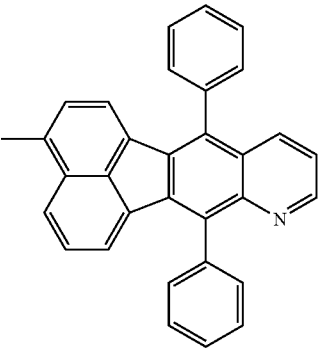 | 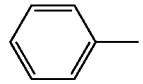 |
| 2620 | CH₃— | 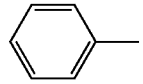 | 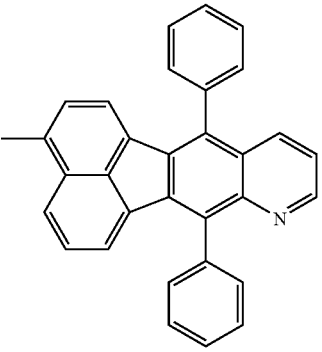 | 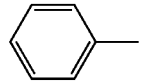 |
| 2621 | H— | 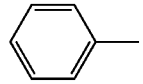 | 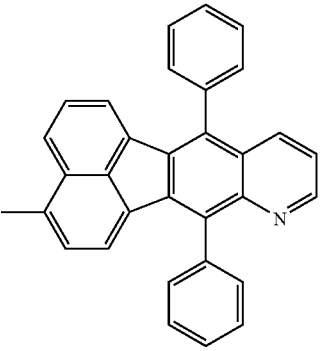 | |

TABLE 58-continued

| Compd. No. | R1 | R2 | R3 | Ar |
|---|---|---|---|---|
| 2622 | CH₃— | 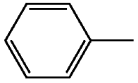 | 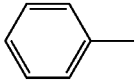 | 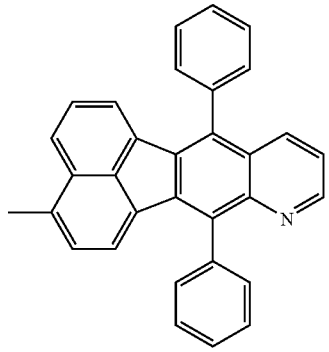 |
| 2623 | H— | 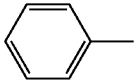 | 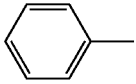 | 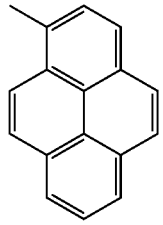 |
| 2624 | CH₃— | 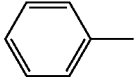 | 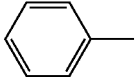 | 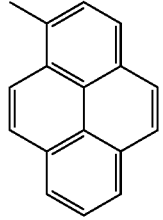 |

Compound Example 18

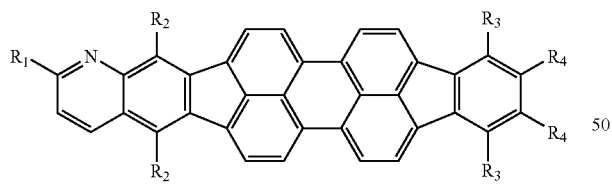

wherein:

$R_1$ represents a hydrogen atom, or an alkyl group such as a methyl group or an ethyl group;

$R_2$ represents an aryl group such as a phenyl group or a tolyl group, or a fused polycyclic aromatic group with three or less rings such as a fluorenyl group; and $R_3$ and $R_4$ each represent a hydrogen atom, or an alkyl group such as a methyl group.

TABLE 59

| Compd. No. | R1 | R2 | R3 | R4 |
|---|---|---|---|---|
| 2701 | H— | 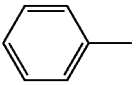 | H— | H— |
| 2702 | CH₃— | 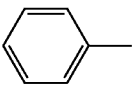 | H— | H— |
| 2703 | H— | 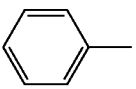 | CH₃— | CH₃— |
| 2704 | CH₃— | 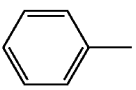 | CH₃— | CH₃— |
| 2705 | H— | 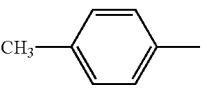 | H— | H— |
| 2706 | CH₃— | 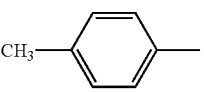 | H— | H— |

TABLE 59-continued

| Compd. No. | R1 | R2 | R3 | R4 |
|---|---|---|---|---|
| 2707 | H— | 2,4-dimethylphenyl | CH₃— | H— |
| 2708 | CH₃— | 2,4-dimethylphenyl | CH₃— | H— |
| 2709 | H— | methylnaphthyl | H— | H— |
| 2710 | CH₃— | methylnaphthyl | H— | H— |
| 2711 | H— | methylnaphthyl | CH₃— | H— |
| 2712 | CH₃— | methylnaphthyl | CH₃— | H— |
| 2713 | H— | methyl-9,9-dimethylfluorenyl | H— | H— |
| 2714 | CH₃— | methyl-9,9-dimethylfluorenyl | H— | H— |
| 2715 | H— | methyl-9,9-dimethylfluorenyl | CH₃— | H— |
| 2716 | CH₃— | methyl-9,9-dimethylfluorenyl | CH₃— | H— |
| 2717 | H— | methyl-9,9-dimethylfluorenyl | CH₃— | CH₃— |
| 2718 | CH₃— | methyl-9,9-dimethylfluorenyl | CH₃— | CH₃— |

TABLE 60

| Compd. No. | R1 | R2 | R3 | R4 |
|---|---|---|---|---|
| 2719 | H— | bis(di-tert-butyl)methylfluorenyl-fluorenyl | H— | H— |
| 2720 | CH₃— | bis(di-tert-butyl)methylfluorenyl-fluorenyl | H— | H— |

Compound Example 19

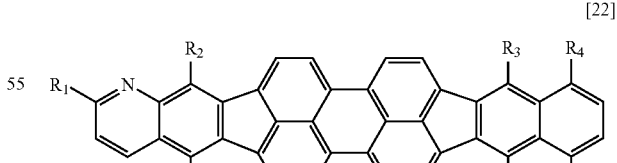

[22]

wherein:
R₁ represents a hydrogen atom, or an alkyl group such as a methyl group;
R₂ and R₃ each represent an aryl group such as a phenyl group or a tolyl group, or a fused polycyclic aromatic group with three or less rings such as a fluorenyl group; and R4 represents a hydrogen atom, or an alkyl group such as a methyl group.

TABLE 61

| Compd. No. | R1 | R2 | R3 | R4 |
|---|---|---|---|---|
| 2801 | H— | phenyl | phenyl | H— |
| 2802 | CH3— | phenyl | phenyl | H— |
| 2803 | H— | phenyl | phenyl | CH3— |
| 2804 | CH3— | phenyl | phenyl | CH3— |
| 2805 | H— | phenyl | 4-CH3-phenyl | H— |
| 2806 | CH3— | phenyl | 4-CH3-phenyl | H— |
| 2807 | H— | phenyl | 4-CH3-phenyl | CH3— |
| 2808 | CH3— | phenyl | 4-CH3-phenyl | CH3— |
| 2809 | H— | 4-CH3-phenyl | 4-CH3-phenyl | H— |
| 2810 | CH3— | 4-CH3-phenyl | 4-CH3-phenyl | H— |
| 2811 | H— | 4-CH3-phenyl | phenyl | H— |
| 2812 | CH3— | 4-CH3-phenyl | phenyl | H— |
| 2813 | H— | 4-CH3-phenyl | phenyl | CH3— |
| 2814 | CH3— | 4-CH3-phenyl | phenyl | CH3— |
| 2815 | H— | naphthyl | phenyl | H— |
| 2816 | CH3— | naphthyl | phenyl | H— |
| 2817 | H— | naphthyl | 4-CH3-phenyl | H— |
| 2818 | CH3— | naphthyl | 4-CH3-phenyl | H— |
| 2819 | H— | naphthyl | naphthyl | H— |
| 2820 | CH3— | naphthyl | naphthyl | H— |

TABLE 62

| Compd. No. | R1 | R2 | R3 | R4 |
|---|---|---|---|---|
| 2821 | H— | 9,9-dimethyl-2-fluorenyl | phenyl | H— |
| 2822 | CH3— | 9,9-dimethyl-2-fluorenyl | phenyl | H— |

TABLE 62-continued

| Compd. No. | R1 | R2 | R3 | R4 |
|---|---|---|---|---|
| 2823 | H— | phenyl | 9,9-dimethylfluoren-2-yl | H— |
| 2824 | CH₃— | methylphenyl | 9,9-dimethylfluoren-2-yl | H— |
| 2825 | H— | 9,9-dimethylfluoren-2-yl | 9,9-dimethylfluoren-2-yl | H— |
| 2826 | CH₃— | 9,9-dimethylfluoren-2-yl | 9,9-dimethylfluoren-2-yl | H— |
| 2827 | H— | 2,7-di-tert-butyl-4,9,9-trimethylfluoren-2-yl | phenyl | H— |
| 2828 | CH₃— | 2,7-di-tert-butyl-4,9,9-trimethylfluoren-2-yl | phenyl | H— |

TABLE 62-continued

| Compd. No. | R1 | R2 | R3 | R4 |
|---|---|---|---|---|
| 2829 | H— | phenyl | 4-methyl-2,7-di-tert-butyl-9,9-dimethylfluoren-3-yl | H— |

TABLE 63

| Compd.No. | R1 | R2 | R3 | R4 |
|---|---|---|---|---|
| 2830 | CH₃— | phenyl | 4-methyl-2,7-di-tert-butyl-9,9-dimethylfluoren-3-yl | H— |
| 2831 | H— | 4-methyl-2,7-di-tert-butyl-9,9-dimethylfluoren-3-yl | 4-methyl-2,7-di-tert-butyl-9,9-dimethylfluoren-3-yl | H— |

TABLE 63-continued

| Compd.No. | R1 | R2 | R3 | R4 |
|---|---|---|---|---|
| 2832 | CH₃— | 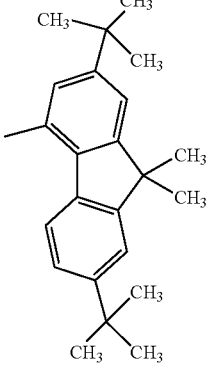 | 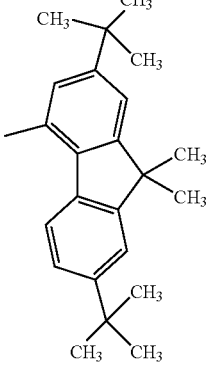 | H— |

Compound Example 20

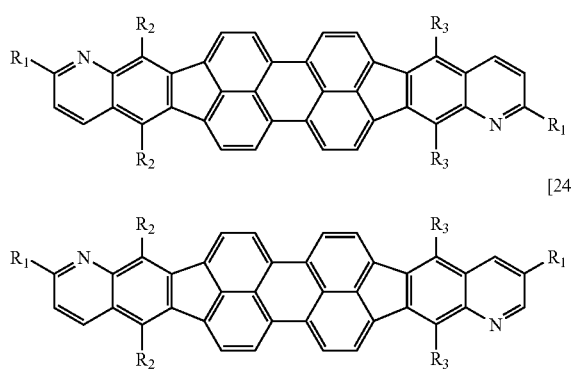

wherein:

R₁ represents a hydrogen atom, or an alkyl group such as a methyl group;

R₂ and R₃ each represent an aryl group such as a phenyl group or a tolyl group, a fused polycyclic aromatic group with three or less rings such as a fluorenyl group, or an alkyl group such as a methyl group.

TABLE 64

| Compd.No. | R1 | R2 | R3 |
|---|---|---|---|
| 2901 | H— | 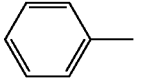 | 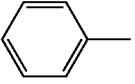 |
| 2902 | CH₃— | 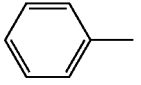 | 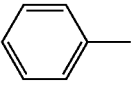 |
| 2903 | H— | 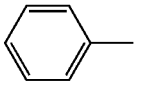 | CH₃— |
| 2904 | CH₃— | 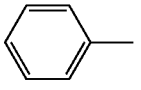 | CH₃— |
| 2905 | H— | 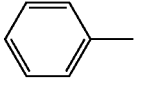 | 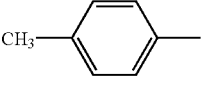 |
| 2906 | CH₃— | 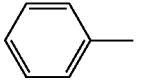 | 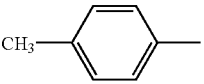 |

TABLE 64-continued

| Compd.No. | R1 | R2 | R3 |
|---|---|---|---|
| 2907 | H— | 2,5-dimethylphenyl | 2,5-dimethylphenyl |
| 2908 | CH₃— | 2,5-dimethylphenyl | 2,5-dimethylphenyl |
| 2909 | H— | 2-methylnaphthyl | phenyl |
| 2910 | CH₃— | 2-methylnaphthyl | phenyl |
| 2911 | H— | 2-methylnaphthyl | 4-methylphenyl |
| 2912 | CH₃— | 2-methylnaphthyl | 4-methylphenyl |
| 2913 | H— | 2-methylnaphthyl | 2-methylnaphthyl |
| 2914 | CH₃— | 2-methylnaphthyl | 2-methylnaphthyl |
| 2915 | H— | 7-methyl-9,9-dimethylfluorenyl | phenyl |
| 2916 | CH₃— | 7-methyl-9,9-dimethylfluorenyl | phenyl |
| 2917 | H— | 7-methyl-9,9-dimethylfluorenyl | CH₃— |
| 2918 | CH₃— | 7-methyl-9,9-dimethylfluorenyl | CH₃— |

TABLE 64-continued
| Compd.No. | R1 | R2 | R3 |
|---|---|---|---|
| 2919 | H— | 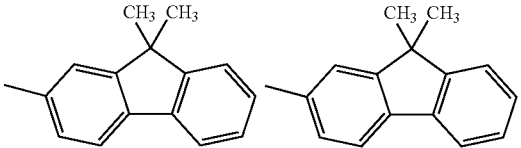 | 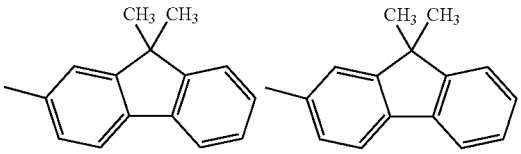 |
| 2920 | CH₃— | 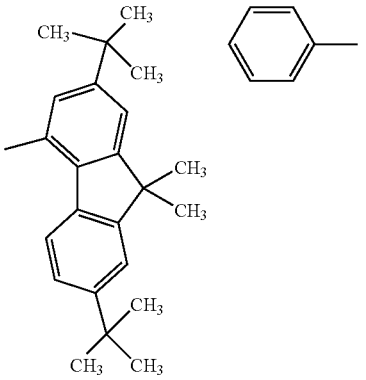 | 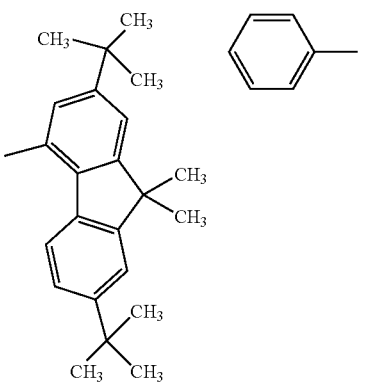 |
TABLE 65
| Compd.No. | R1 | R2 | R3 |
|---|---|---|---|
| 2921 | H— | 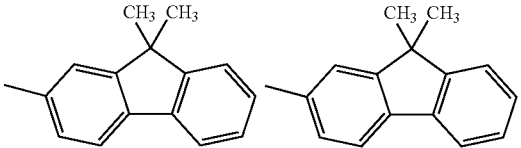 | 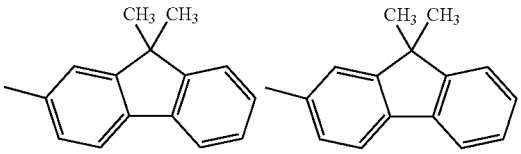 |
| 2922 | CH₃— | 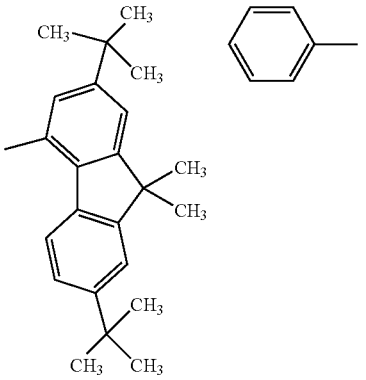 | 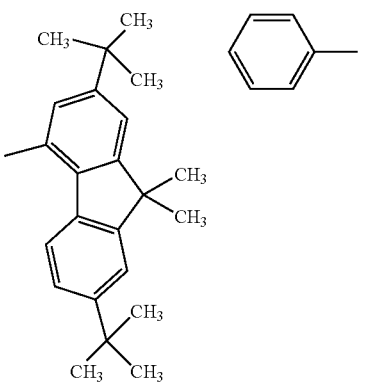 |

TABLE 65-continued

| Compd.No. | R1 | R2 | R3 |
|---|---|---|---|
| 2923 | H— | [fluorene with tBu, CH3, and C(CH3)2 substituents] | [fluorene with tBu, CH3, and C(CH3)2 substituents] |
| 2924 | CH3— | [fluorene with tBu, CH3, and C(CH3)2 substituents] | [fluorene with tBu, CH3, and C(CH3)2 substituents] |

Compound Example 21

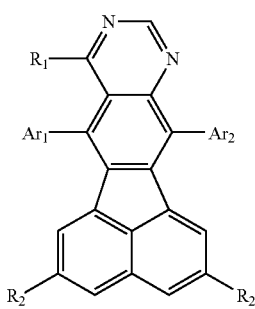

wherein:

Ar$_1$ and Ar$_2$ each represent an aryl group such as a phenyl group, or a fused polycyclic aromatic group with three or less rings such as a fluorenyl group; and R$_1$ and R$_2$ each represent a hydrogen atom, or an alkyl group such as a methyl group, an ethyl group, or a tertiary butyl group.

When Ar$_1$ and Ar$_2$ are different from each other, Ar$_1$ and Ar$_2$ shown in the following tables may be replaced with each other.

TABLE 66

| Compd.No. | Ar1 | Ar2 | R1 | R2 |
|---|---|---|---|---|
| 3001 | [phenyl] | [phenyl] | H— | H— |
| 3002 | [phenyl] | [phenyl] | CH3— | H— |

TABLE 66-continued
| Compd.No. | Ar1 | Ar2 | R1 | R2 |
|---|---|---|---|---|
| 3003 | 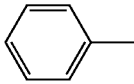 | 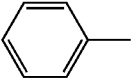 | H— | 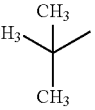 |
| 3004 | 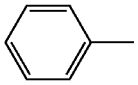 | 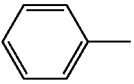 | CH₃— | 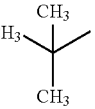 |
| 3005 | 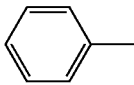 | 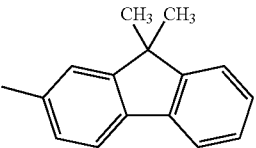 | H— | H— |
| 3006 | 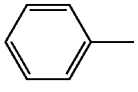 | 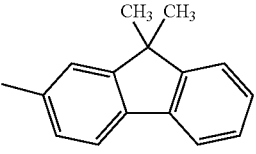 | CH₃— | H— |
| 3007 | 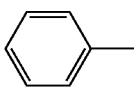 | 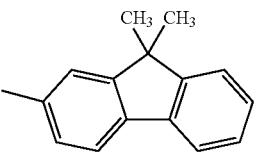 | H— | 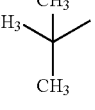 |
| 3008 | 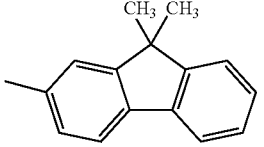 | 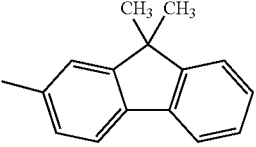 | H— | H— |
| 3009 | 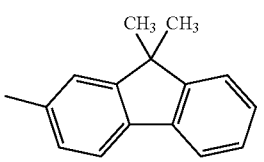 | 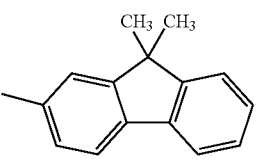 | CH₃— | H— |

TABLE 66-continued

| Compd.No. | Ar1 | Ar2 | R1 | R2 |
|---|---|---|---|---|
| 3010 | (2-methyl-9,9-dimethylfluoren-7-yl) | (2-methyl-9,9-dimethylfluoren-7-yl) | H— | tert-butyl |
| 3011 | (2-methyl-9,9-dimethylfluoren-7-yl) | (2-methyl-9,9-dimethylfluoren-7-yl) | CH₃— | tert-butyl |
| 3012 | (2,7-di-tert-butyl-4,9,9-trimethylfluoren-yl) | (2,7-di-tert-butyl-4,9,9-trimethylfluoren-yl) | H— | H— |

TABLE 67

| Compd.No. | Ar1 | Ar2 | R1 | R2 |
|---|---|---|---|---|
| 3013 | (2,7-di-tert-butyl-4,9,9-trimethylfluoren-yl) | (2,7-di-tert-butyl-4,9,9-trimethylfluoren-yl) | CH₃— | H— |

TABLE 67-continued

| Compd.No. | Ar1 | Ar2 | R1 | R2 |
|---|---|---|---|---|
| 3014 | (fluorene with multiple CH3 and C(CH3)3 substituents) | (fluorene with multiple CH3 and C(CH3)3 substituents) | H— | C(CH3)3 |

Compound Example 22

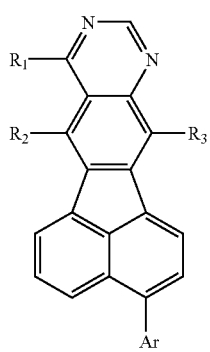

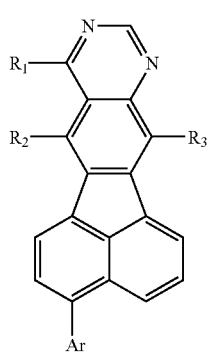

wherein:

[26]

$R_1$ represents a hydrogen atom, or an alkyl group such as a methyl group;

$R_2$ and $R_3$ each represent an aryl group such as a phenyl group, a fused polycyclic aromatic group with three or less rings such as a fluorenyl group, or an alkyl group such as a methyl group; and

[27]

Ar represents a fused polycyclic aromatic group such as a fluoranthenyl group or a benzofluoranthenyl group.

When $R_2$ and $R_3$ are different from each other, $R_2$ and $R_3$ shown in the following tables may be replaced with each other.

TABLE 68

| Compd.No. | R1 | R2 | R3 | Ar |
|---|---|---|---|---|
| 3101 | H— | phenyl | phenyl | fluoranthenyl |

TABLE 68-continued

| Compd.No. | R1 | R2 | R3 | Ar |
|---|---|---|---|---|
| 3102 | CH₃— | phenyl | phenyl | fluoranthenyl |
| 3103 | H— | phenyl | CH₃— | fluoranthenyl |
| 3104 | CH₃— | phenyl | CH₃— | fluoranthenyl |
| 3105 | H— | 9,9-dimethylfluoren-2-yl | 9,9-dimethylfluoren-2-yl | fluoranthenyl |
| 3106 | CH₃— | 9,9-dimethylfluoren-2-yl | 9,9-dimethylfluoren-2-yl | fluoranthenyl |
| 3107 | H— | 4-methyl-2,7-di-tert-butyl-9,9-dimethylfluorenyl | 4-methyl-2,7-di-tert-butyl-9,9-dimethylfluorenyl | fluoranthenyl |

TABLE 68-continued

| Compd.No. | R1 | R2 | R3 | Ar |
|---|---|---|---|---|
| 3108 | CH₃— | [2,4,7-tri-tert-butyl-9,9-dimethylfluorenyl] | [2,4,7-tri-tert-butyl-9,9-dimethylfluorenyl] | [fluoranthenyl] |
| 3109 | H— | [phenyl] | [phenyl] | [7,12-diphenylbenzo[k]fluoranthenyl] |
| 3110 | CH₃— | [phenyl] | [phenyl] | [7,12-diphenylbenzo[k]fluoranthenyl] |

TABLE 69

| Compd.No. | R1 | R2 | R3 | Ar |
|---|---|---|---|---|
| 3111 | H— | [phenyl] | CH₃— | [7,12-diphenylbenzo[k]fluoranthenyl] |

TABLE 69-continued

| Compd.No. | R1 | R2 | R3 | Ar |
|---|---|---|---|---|
| 3112 | CH₃— | (tolyl) | CH₃— | (structure) |
| 3113 | H— | (9,9-dimethylfluorenyl) | (9,9-dimethylfluorenyl) | (structure) |
| 3114 | CH₃— | (9,9-dimethylfluorenyl) | (9,9-dimethylfluorenyl) | (structure) |
| 3115 | H— | (di-tert-butyl-methyl-9,9-dimethylfluorenyl) | (di-tert-butyl-methyl-9,9-dimethylfluorenyl) | (structure) |

TABLE 69-continued

| Compd.No. | R1 | R2 | R3 | Ar |
|---|---|---|---|---|
| 3116 | $CH_3$— | (2,7-di-tert-butyl-4-methyl-9,9-dimethylfluorenyl) | (2,7-di-tert-butyl-4-methyl-9,9-dimethylfluorenyl) | (methyl-diphenyl-fluoranthenyl) |

TABLE 70

| Compd.No. | R1 | R2 | R3 | Ar |
|---|---|---|---|---|
| 3117 | H— | phenyl | phenyl | (methylpyrenyl) |
| 3118 | $CH_3$— | phenyl | phenyl | (methylpyrenyl) |

Compound Example 23

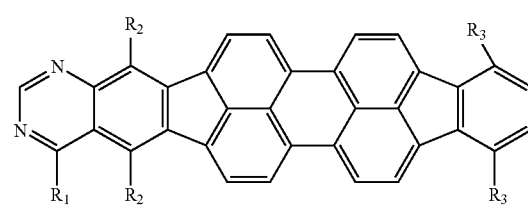

wherein:

$R_1$ represents a hydrogen atom, or an alkyl group such as a methyl group or an ethyl group;

$R_2$ represents an aryl group such as a phenyl group, or a fused polycyclic aromatic group with three or less rings such as a fluorenyl group; and $R_3$ and $R_4$ each represent a hydrogen atom, or an alkyl group such as a methyl group.

TABLE 71

| Compd.No. | R1 | R2 | R3 | R4 |
|---|---|---|---|---|
| 3201 | H— | phenyl | H— | H— |

TABLE 71-continued
| Compd.No. | R1 | R2 | R3 | R4 |
|---|---|---|---|---|
| 3202 | CH₃— | 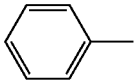 | H— | H— |
| 3203 | H— | 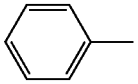 | CH₃— | CH₃— |
| 3204 | CH₃— | 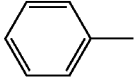 | CH₃— | CH₃— |
| 3205 | H— | 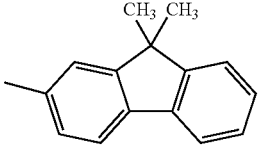 | H— | H— |
| 3206 | CH₃— | 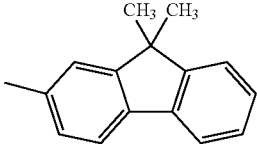 | H— | H— |
| 3207 | H— | 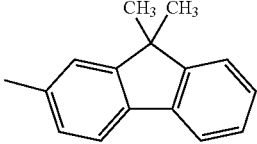 | CH₃— | H— |
| 3208 | CH₃— | 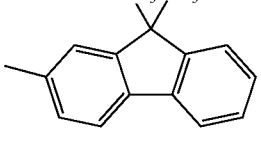 | CH₃— | H— |
| 3209 | H— | 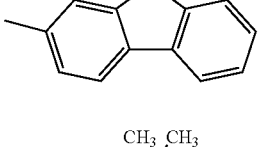 | CH₃— | CH₃— |
| 3210 | CH₃— | 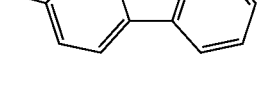 | CH₃— | CH₃— |

TABLE 71-continued

| Compd.No. | R1 | R2 | R3 | R4 |
|---|---|---|---|---|
| 3211 | H— | 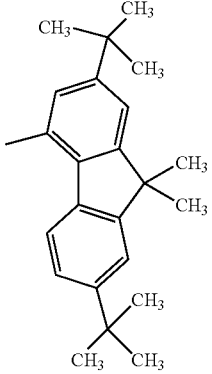 | H— | H— |
| 3212 | CH₃— | 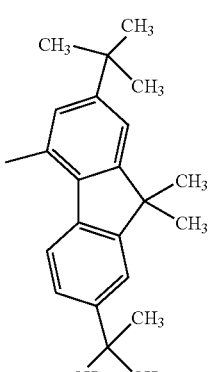 | H— | H— |

Compound Example 24

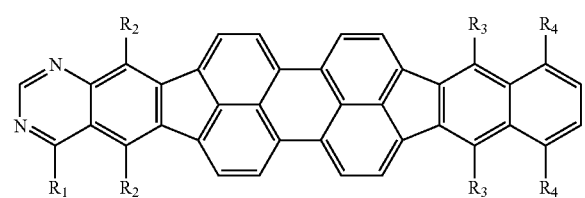

wherein:

$R_1$ represents a hydrogen atom, or an alkyl group such as a methyl group;

$R_2$ and $R_3$ each represent an aryl group such as a phenyl group, or a fused polycyclic aromatic group with three or less rings such as a fluorenyl group; and $R_4$ represents a hydrogen atom, or an alkyl group such as a methyl group.

TABLE 72

| Compd.No. | R1 | R2 | R3 | R4 |
|---|---|---|---|---|
| 3301 | H— | 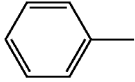 | 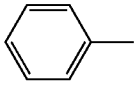 | H— |
| 3302 | CH₃— | 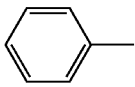 | 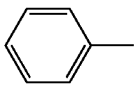 | H— |
| 3303 | H— | 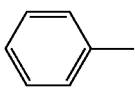 | 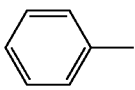 | CH₃— |

TABLE 72-continued

| Compd.No. | R1 | R2 | R3 | R4 |
|---|---|---|---|---|
| 3304 | CH₃— | phenyl | phenyl | CH₃— |
| 3305 | H— | 9,9-dimethyl-2-fluorenyl | phenyl | H— |
| 3306 | CH₃— | 9,9-dimethyl-2-fluorenyl | phenyl | H— |
| 3307 | H— | phenyl | 9,9-dimethyl-2-fluorenyl | H— |
| 3308 | CH₃— | phenyl | 9,9-dimethyl-2-fluorenyl | H— |
| 3309 | H— | 9,9-dimethyl-2-fluorenyl | 9,9-dimethyl-2-fluorenyl | H— |
| 3310 | CH₃— | 9,9-dimethyl-2-fluorenyl | 9,9-dimethyl-2-fluorenyl | H— |
| 3311 | H— | 2,7-di-tert-butyl-4,9,9-trimethyl-fluorenyl | phenyl | H— |

TABLE 72-continued
| Compd.No. | R1 | R2 | R3 | R4 |
|---|---|---|---|---|
| 3312 | CH₃— | 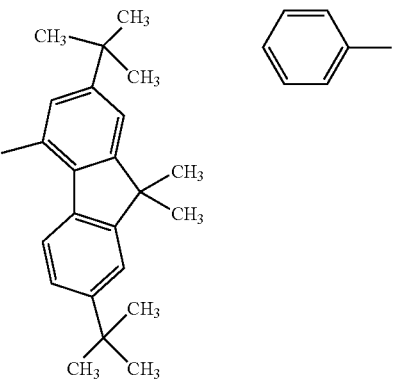 | 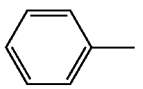 | H— |
| 3313 | H— | 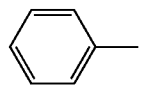 | 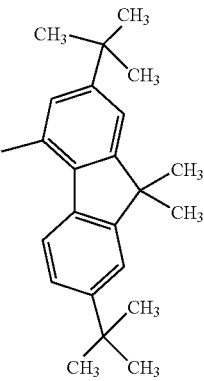 | H— |
TABLE 73
| Compd.No. | R1 | R2 | R3 | R4 |
|---|---|---|---|---|
| 3314 | CH₃— | 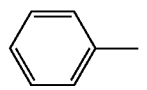 | 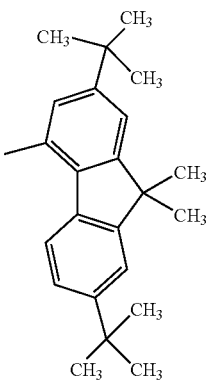 | H— |

TABLE 73-continued

| Compd.No. | R1 | R2 | R3 | R4 |
|---|---|---|---|---|
| 3315 | H— | [2,7-di-tert-butyl-4-methyl-9,9-dimethylfluorenyl] | [2,7-di-tert-butyl-4-methyl-9,9-dimethylfluorenyl] | H— |
| 3316 | CH₃— | [2,7-di-tert-butyl-4-methyl-9,9-dimethylfluorenyl] | [2,7-di-tert-butyl-4-methyl-9,9-dimethylfluorenyl] | H— |

Compound Example 25

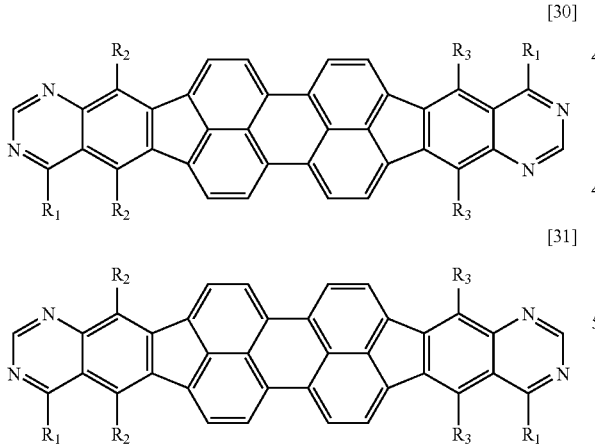

wherein:

R₁ represents a hydrogen atom, or an alkyl group such as a methyl group;

R₂ and R₃ each represent an aryl group such as a phenyl group or a tolyl group, a fused polycyclic aromatic group with three or less rings such as a fluorenyl group, or an alkyl group such as a methyl group.

TABLE 74

| Compd.No. | R1 | R2 | R3 |
|---|---|---|---|
| 3401 | H— | phenyl | phenyl |

TABLE 74-continued
| Compd.No. | R1 | R2 | R3 |
|---|---|---|---|
| 3402 | CH₃— | 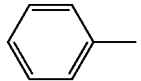 |  |
| 3403 | H— | 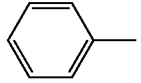 | CH₃— |
| 3404 | CH₃— | 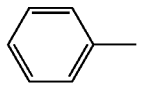 | CH₃— |
| 3405 | H— | 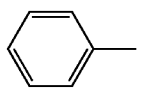 | 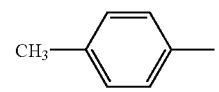 |
| 3406 | CH₃— | 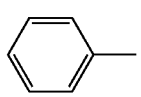 | 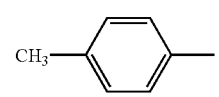 |
| 3407 | H— | 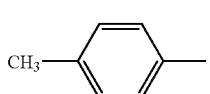 | 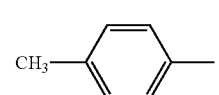 |
| 3408 | CH₃— | 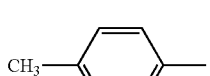 | 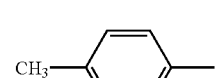 |
| 3409 | H— | 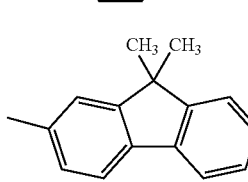 | 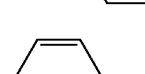 |
| 3410 | CH₃— | 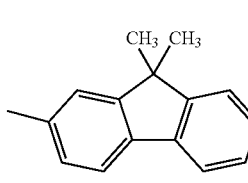 | 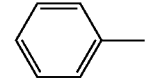 |
| 3411 | H— | 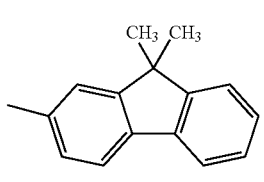 | CH₃— |
| 3412 | CH₃— | 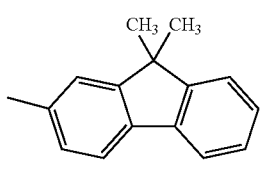 | CH₃— |
| 3413 | H— | 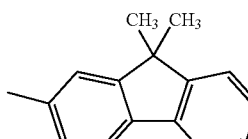 | 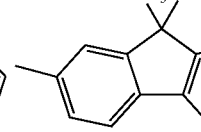 |

TABLE 74-continued

| Compd.No. | R1 | R2 | R3 |
|---|---|---|---|
| 3414 | CH₃— | 9,9-dimethyl-2-methylfluorenyl | 9,9-dimethyl-2-methylfluorenyl |
| 3415 | H— | 2,7-di-tert-butyl-4,9,9-trimethylfluorenyl | phenyl |

TABLE 75

| Compd.No. | R1 | R2 | R3 |
|---|---|---|---|
| 3416 | CH₃— | 2,7-di-tert-butyl-4,9,9-trimethylfluorenyl | phenyl |
| 3417 | H— | 2,7-di-tert-butyl-4,9,9-trimethylfluorenyl | 2,7-di-tert-butyl-4,9,9-trimethylfluorenyl |

TABLE 75-continued

| Compd.No. | R1 | R2 | R3 |
|---|---|---|---|
| 3418 | CH₃— | (2,7-di-tert-butyl-4-methyl-9,9-dimethylfluorenyl) | (2,7-di-tert-butyl-4-methyl-9,9-dimethylfluorenyl) |

Compound Example 26

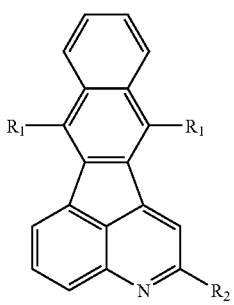

wherein:

[32]

R₁ represents a hydrogen atom, an aryl group such as a phenyl group, or a fused polycyclic aromatic group with three or less rings such as a fluorenyl group; and R₂ represents a hydrogen atom, an aryl group such as a phenyl group or a biphenyl group, or a fused polycyclic aromatic group such as a naphthyl group, a fluorenyl group, or a pyrenyl group.

TABLE 76

| Compd.No. | R1 | R2 |
|---|---|---|
| 3501 | phenyl | phenyl |
| 3502 | H— | phenyl |
| 3503 | phenyl | H— |
| 3504 | phenyl | 9,9-dimethylfluorenyl |
| 3505 | 9,9-dimethylfluorenyl | 9,9-dimethylfluorenyl |

TABLE 76-continued
| Compd.No. | R1 | R2 |
|---|---|---|
| 3506 | H— | 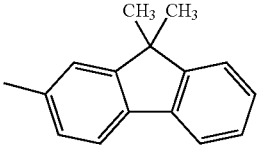 |
| 3507 | 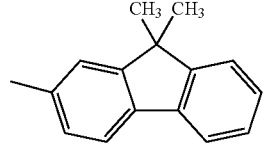 | H— |
| 3508 | 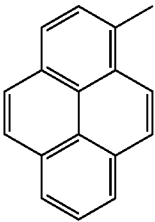 | 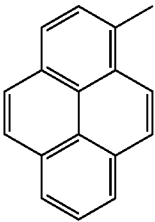 |
| 3509 | H— | 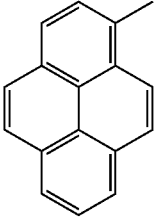 |
| 3510 | 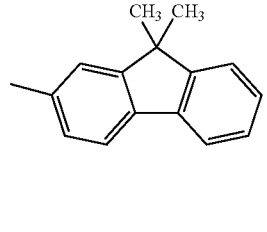 | 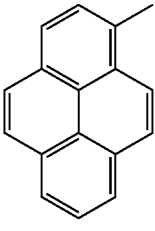 |
| 3511 | 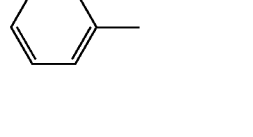 |  |
| 3512 | H— | 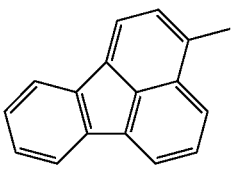 |
| 3513 | 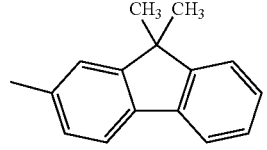 |  |

235
Compound Example 27

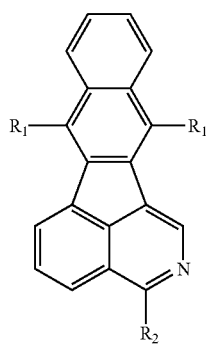

wherein:

[33] R₁ represents a hydrogen atom, an aryl group such as a phenyl group, or a fused polycyclic aromatic group with three or less rings such as a fluorenyl group; and R₂ represents a hydrogen atom, an aryl group such as a phenyl group or a biphenyl group, or a fused polycyclic aromatic group such as a naphthyl group, a fluorenyl group, or a pyrenyl group.

TABLE 77

| Compd.No. | R1 | R2 |
|---|---|---|
| 3601 | phenyl | phenyl |
| 3602 | H— | phenyl |
| 3603 | phenyl | H— |
| 3604 | phenyl | 9,9-dimethylfluorenyl |
| 3605 | 9,9-dimethylfluorenyl | 9,9-dimethylfluorenyl |
| 3606 | H— | 9,9-dimethylfluorenyl |
| 3607 | 9,9-dimethylfluorenyl | H— |

TABLE 77-continued

| Compd.No. | R1 | R2 |
|---|---|---|
| 3608 | phenyl | pyrenyl |
| 3609 | H— | pyrenyl |
| 3610 | 9,9-dimethylfluorenyl | pyrenyl |
| 3611 | phenyl | fluoranthenyl |
| 3612 | H— | fluoranthenyl |
| 3613 | 9,9-dimethylfluorenyl | fluoranthenyl |

The fused heterocyclic compound of the present invention has a nitrogen-containing aromatic heterocyclic ring structure obtained by introducing at least one nitrogen atom into a specific position of a benzofluoranthene skeleton. Accordingly, a stable amorphous film can be formed of the compound, and the compound shows excellent electron transporting property. Those properties allow the compound to be suitably used as a charge transportable material in, for example, an electrophotographic photosensitive member, an organic electroluminescence device, a photoelectric conversion element, or an organic solar cell. In addition, the compound is suitable as a material for an organic electroluminescence device because the application of the compound to an organic electroluminescence device can contribute to an achievement of high luminous efficiency and a reduction in voltage at which the device is driven.

Next, an organic light emitting device of the present invention will be described in more detail.

The organic light emitting device of the present invention comprised a pair of electrodes composed of an anode and a cathode at least one of which is made of an electrode material transparent or semi-transparent; and at least a layer containing one or a plurality of organic compounds held between the pair of electrodes. The organic light emitting device of the present invention is preferably an electroluminescence device that emits light by applying voltage between the pair of electrodes.

In addition, at least one layer containing an organic compound, preferably at least one layer having a light emitting region, or more preferably a light emitting layer contains at least one kind of the above fused heterocyclic compound of the present invention.

In addition, when the layer containing the fused heterocyclic compound is formed of two or more compounds including a host and a guest, the host or the guest is preferably the fused heterocyclic compound of the present invention. It should be noted that the term "guest" as used in the present invention refers to a compound that emits light in response to recombination between a hole and an electron in the light emitting region of an organic EL device. The guest is incorporated into another compound (host) of which the light emitting region is formed.

When the fused heterocyclic compound of the present invention is used as a guest, the content of the compound is preferably 0.01 wt % or more to 80 wt % or less, more preferably 0.1 wt % or more to 30 wt % or less, or particularly preferably 0.1 wt % or more to 15 wt % or less. A guest material may be incorporated into the entirety of a layer formed of a host material uniformly or with a concentration gradient. Alternatively, the guest material may be partially incorporated into a certain region of the host material layer so that a region of the layer free of the guest material is present.

In addition, when the fused heterocyclic compound of the present invention is used as a guest, the layer preferably contains a host having an energy gap (value calculated from an optical absorption end of UV measurement) larger than that of the guest. In this case, energy transfer from the guest to the host can be controlled, and luminous efficiency can be enhanced as a result of light emission only from the guest.

In addition, when the fused heterocyclic compound of the present invention is used as a guest, the reduction potential of the guest is preferably higher than the reduction potential of the host by 0.3 V or more. In this case, the voltage at which the device is driven can be reduced, high luminance can be maintained for a long time period, and the deterioration of the device due to energization can be reduced.

Only a light emitting layer may be the layer containing the fused heterocyclic compound of the present invention. However, the layer containing the fused heterocyclic compound of the present invention is applicable to a layer except the light emitting layer (such as a hole injecting layer, a hole transporting layer, an electron injecting layer, an electron transporting layer, or an electron blocking layer) as required.

In the organic light emitting device of the present invention, the fused heterocyclic compound of the present invention is formed into an organic layer between the anode and the cathode by a vacuum vapor deposition method or a solution application method. The thickness of the organic layer is smaller than 10 μm, preferably 0.5 μm or less, or more preferably 0.01 μm or more to 0.5 μm or less.

FIGS. 1 to 5 each show a preferable example of the organic light emitting device of the present invention.

FIG. 1 is a sectional view showing an example of an organic light emitting device according to the present invention. As shown in FIG. 1, the organic light emitting device has a structure in which an anode 2, a light emitting layer 3, and a cathode 4 are provided on a substrate 1 in this order. The electroluminescence device used herein is useful in the case where a compound having hole transporting property, electron transporting property, and light emitting property by itself is used or where compounds having the respective properties are used in a mixture.

Figure 2:
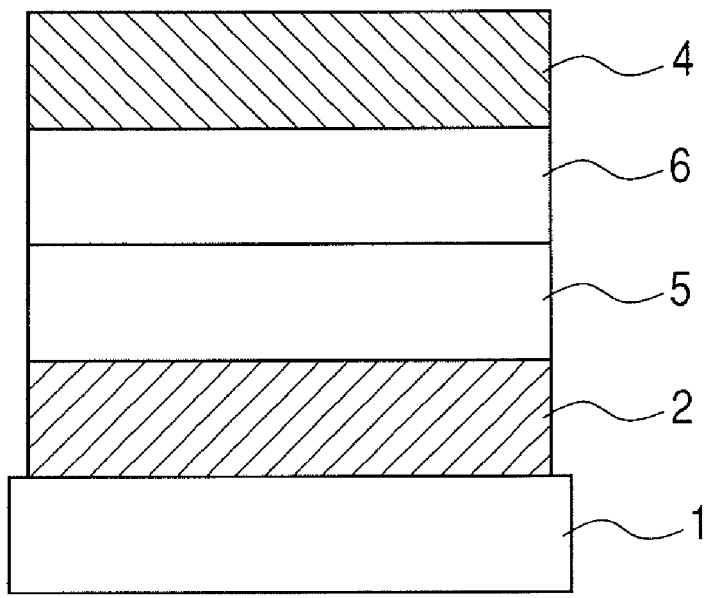
FIG. 2 is a sectional view showing another example of the organic light emitting device of the present invention.

FIG. 2 is a sectional view showing another example of the organic light emitting device according to the present invention. As shown in FIG. 2, the organic light emitting device has a structure in which the anode 2, a hole transport layer 5, an electron transport layer 6, and the cathode 4 are provided on the substrate 1 in this order. This structure is useful in the case where a material having one or both of hole transporting property and electron transporting property is used as a light emitting substance in each layer, and the light emitting substance is used in combination with a non-illuminant hole transporting substance or electron transporting substance. In this case, the light emitting layer is formed of either the hole transport layer 5 or the electron transport layer 6.

Figure 3:
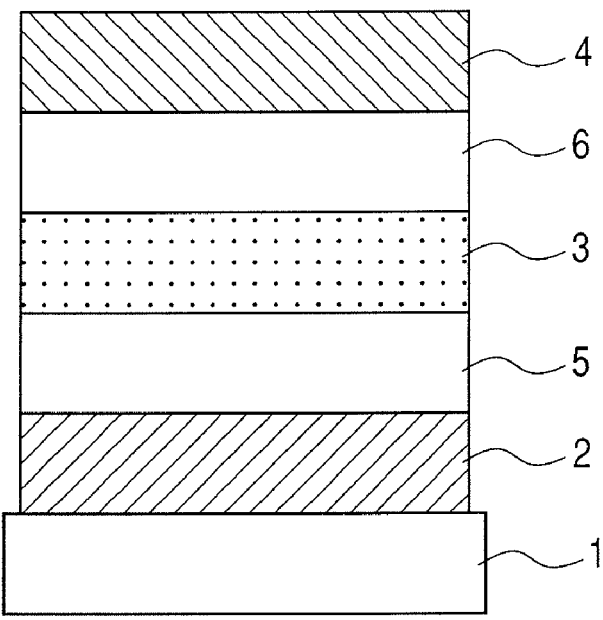
FIG. 3 is a sectional view showing another example of the organic light emitting device of the present invention.

FIG. 3 is a sectional view showing still another example of the organic light emitting device according to the present invention. As shown in FIG. 3, the organic light emitting device has a structure in which the anode 2, the hole transport layer 5, the light emitting layer 3, the electron transport layer 6, and the cathode 4 are provided on the substrate 1 in this order. This organic light emitting device has carrier transporting function and light emitting function separately. The device is used in combination with compounds each having hole transporting property, electron transporting property, or light emitting property as appropriate, thereby allowing a substantial increase in freedom of choice in material to be used. Further, various compounds having different emission wavelengths can be used, thereby allowing an increase in variety of luminescent colors. Further, luminous efficiency may be enhanced by efficiently trapping each carrier or exciton in the light emitting layer 3 provided in the middle of the device.

Figure 4:
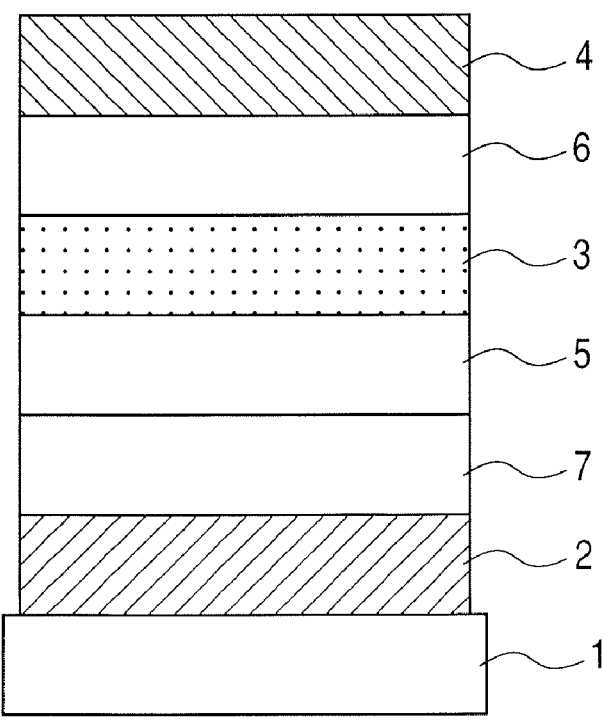
FIG. 4 is a sectional view showing another example of the organic light emitting device of the present invention.

FIG. 4 is a sectional view showing yet another example of the organic light emitting device according to the present invention. FIG. 4 has a structure similar to that shown in FIG. 3 except that a hole-injecting layer 7 is inserted into a side of the anode 2. The structure is effective for improving adhesiveness between the anode 2 and the hole transport layer 5 or for improving hole-injecting property, which is effective in lowering a voltage to be applied to the device.

Figure 5:
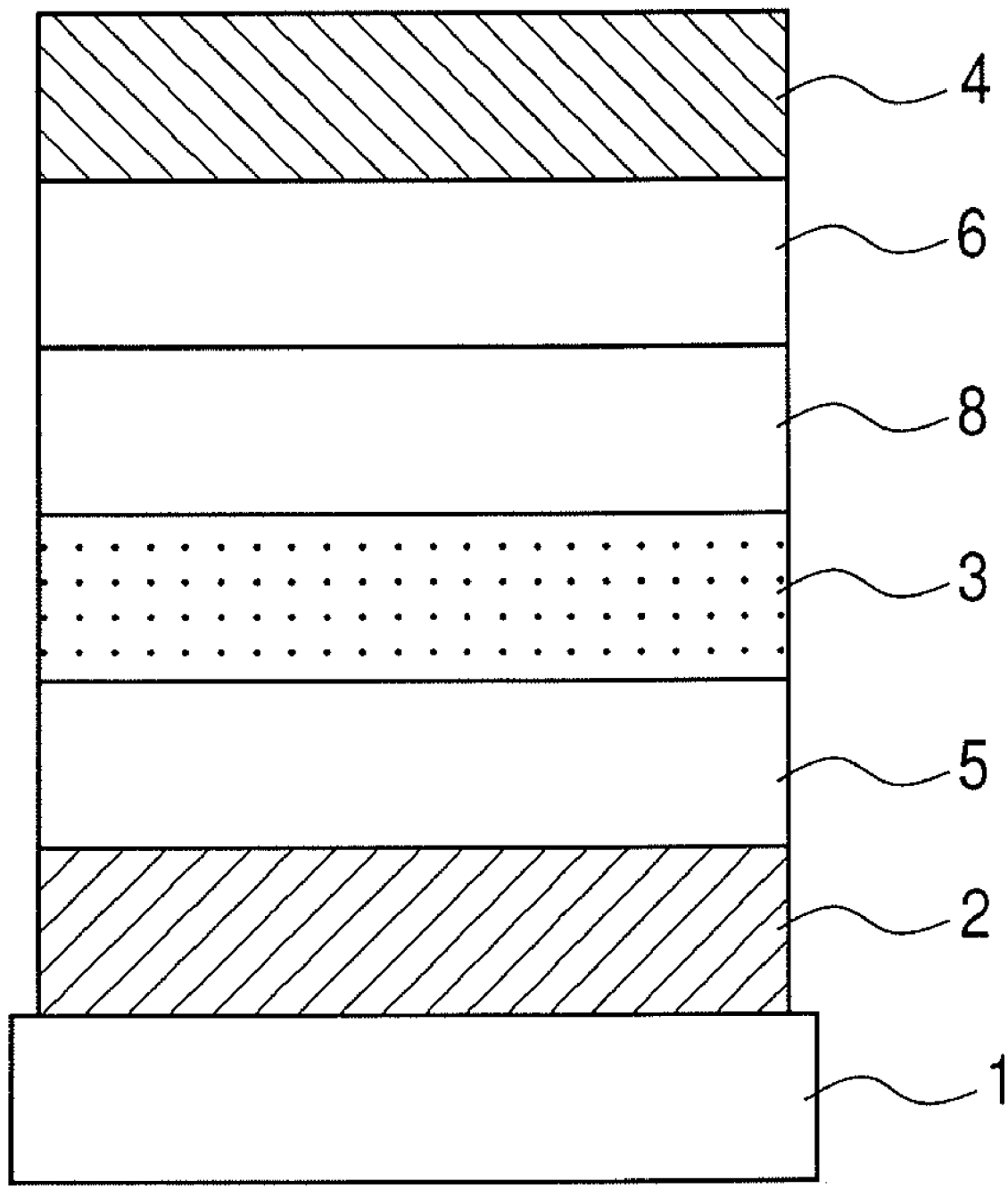
FIG. 5 is a sectional view showing another example of the organic light emitting device of the present invention.

FIG. 5 is a sectional view showing still yet another example of the organic light emitting device according to the present invention. FIG. 5 has a structure similar to that shown in FIG. 3 except that a layer (a hole/exciton-blocking layer 8) for blocking travel of a hole or exciton to a side of the cathode 4 is inserted between the light emitting layer 3 and the electron transport layer 6. The structure uses a compound having an extremely high ionization potential in the hole/exciton-blocking layer 8 and is effective for enhancing luminous efficiency.

However, FIGS. 1 to 5 each show a basic device structure, and the structure of the organic light emitting device of the present invention is not limited to the structures shown in FIGS. 1 to 5. For example, the organic light emitting device of the present invention may have any one of various layer structures including: a structure in which an insulating layer is provided at an interface between an electrode and an organic layer; a structure in which an adhesive layer or interference layer is provided; and a structure in which a hole transport layer is composed of two layers with different ionization potentials.

The organic light emitting device of the present invention may be used in any one of the modes shown in FIGS. 1 to 5.

In particular, an organic layer using the fused heterocyclic aromatic compound of the present invention is useful as a light emitting layer, an electron transport layer, or a hole transport layer. In addition, a layer formed by a vacuum deposition method, a solution coating method, or the like is hardly crystallized and has excellent stability over time.

In the present invention, the fused heterocyclic compound is used particularly as a component of the light emitting layer.

However, a conventionally known additive compound such as a hole transporting compound of a low molecular weight compound or polymer compound, luminescent compound, or electron transporting compound can be used together as required.

Examples of the compounds will be shown below.

A preferred hole-injection transporting material has excellent mobility for facilitating injection of a hole from an anode and for transporting the injected hole to a light emitting layer. Examples of a low molecular weight material or polymer material having hole-injection transporting property include, but of course are not limited to, the following.

A triarylamine derivative, a phenylenediamine derivative, a triazole derivative, an oxadiazole derivative, an imidazole derivative, a pyrazoline derivative, a pyrazolone derivative, an oxazole derivative, a fluorenone derivative, a hydrazone derivative, a stilbene derivative, a phthalocyanine derivative, a porphyrin derivative, poly(vinylcarbazole), poly(silylene), poly(thiophene), and other conductive polymers.

Examples of a material which is mainly involved in a light emitting function to be used in the organic light emitting device of the present invention include, but are not limited to, the following.

A fused aromatic ring compound such as a naphthalene derivative, a phenanthrene derivative, a fluorene derivative, a pyrene derivative, a tetracene derivative, a coronene derivative, a chrysene derivative, a perylene derivative, a 9,10-diphenylanthracene derivative, or rubrene; a quinacridone derivative; an acridone derivative; a coumarin derivative; a pyran derivative; Nile red; a pyrazine derivative; a benzoimidazole derivative; a benzothiazole derivative; a benzoxazole derivative; a stilbene derivative; an organometallic complex such as: an organic aluminum complex such as tris(8-quinolinolato)aluminum; or an organic beryllium complex; and a polymer derivative such as a poly(phenylenevinylene)derivative, a poly(fluorene) derivative, a poly(phenylene) derivative, a poly(thienylenevinylene)derivative, or a poly(acetylene) derivative.

The electron-injection transporting material may be arbitrarily selected from materials which facilitate injection of an electron from a cathode and which have a function of transporting the injected electron into a light emitting layer. The material is selected in consideration of, for example, the balance with the mobility of a carrier of the hole transport material. Examples of a material having electron-injection transporting property include, but of course are not limited to, the following.

An oxadiazole derivative, an oxazole derivative, a thiazole derivative, a thiadiazole derivative, a pyrazine derivative, a triazole derivative, a triazine derivative, a perylene derivative, a quinoline derivative, a quinoxaline derivative, a fluorenone derivative, an anthrone derivative, a phenanthroline derivative, and an organometallic complex.

In the organic light emitting device according to the present invention, a layer containing the compound of the present invention and a layer containing other organic compounds are each formed by the following method. A thin film is generally formed by a vacuum deposition method, an ionized evaporation method, sputtering, plasma, or a known coating method (such as a spin coating, dipping, casting, LB, or inkjet method) in which a compound is dissolved in an appropriate solvent. In film formation by a coating method, in particular, a film may be formed by using a compound in combination with an appropriate binder resin.

The binder resin may be selected from a wide variety of binder resins. Examples of the binder resin include, but of course not limited to, the following.

A polyvinyl carbazole resin, a polycarbonate resin, a polyester resin, a polyarylate resin, a polystyrene resin, an ABS resin, a polybutadiene resin, a polyurethane resin, an acrylic resin, a methacrylic resin, a butyral resin, a polyvinyl acetal resin, a polyamide resin, a polyimide resin, a polyethylene resin, a polyethersulfone resin, a diallyl phthalate resin, a phenol resin, an epoxy resin, a silicone resin, a polysulfone resin, and a urea resin.

These resins may be used alone or in a mixture of two or more kinds thereof as a homopolymer or copolymer. Further, an additive such as a known plasticizer, antioxidant, or ultraviolet absorber may be used in combination as required.

An anode material preferably has as large a work function as possible, and examples thereof include: a metal element such as gold, platinum, silver, copper, nickel, palladium, cobalt, selenium, vanadium, or tungsten; an alloy thereof; and a metal oxide such as tin oxide, zinc oxide, indium oxide, indium tin oxide (ITO), or indium zinc oxide. Further, a conductive polymer such as polyaniline, polypyrrole, polythiophene, or polyphenylene sulfide may also be used. Each of those electrode materials may be used alone, or two or more kinds thereof may be used in combination. Further, the anode may have a single layer structure or a multilayer structure.

Meanwhile, a cathode material preferably has a small work function, and examples thereof include: a metal element such as lithium, sodium, potassium, calcium, magnesium, aluminum, indium, ruthenium, titanium, manganese, yttrium, silver, lead, tin, or chromium; and an alloy thereof such as a lithium-indium alloy, a sodium-potassium alloy, a magnesium-silver alloy, an aluminum-lithium alloy, an aluminum-magnesium alloy, or a magnesium-indium alloy. A metal oxide such as indium tin oxide (ITO) may also be used. Each of those electrode materials may be used alone, or two or more kinds thereof may be used in combination. Further, the cathode may have a single layer structure or a multilayer structure.

The substrate to be used in the present invention is not particularly limited, but examples thereof include: an opaque substrate such as a metallic substrate or a ceramics substrate; and a transparent substrate such as a glass substrate, a quartz substrate, or a plastic sheet substrate. In addition, a color filter film, a fluorescent color converting filter film, a dielectric reflection film, or the like may be used in the substrate for controlling luminescent color.

Further, a protective layer or a sealing layer may be formed on the produced device to prevent contact between the device and oxygen, moisture, or the like. Examples of the protective layer include: a diamond thin film; a film formed of an inorganic material such as metal oxide or metal nitride; a polymer film formed of a fluorine resin, polyparaxylene, polyethylene, a silicone resin, or a polystyrene resin; and a photo-curable resin. Further, the device itself may be covered with glass, a gas impermeable film, a metal, or the like and packaged with an appropriate sealing resin.

A thin film transistor (TFT) may be produced on a substrate, and then the device of the present invention may be produced to be connected to TFT.

Regarding the emission direction of a device, the device may have a bottom emission structure (structure in which light is emitted from a substrate side) or a top emission structure (structure in which light is emitted from an opposite side of the substrate).

EXAMPLES

Hereinafter, the present invention will be described more specifically by way of examples, but the present invention is not limited to the examples.

Example 1

Method of Producing Exemplified Compound No. 1308

Exemplified Compound 1308 of the present invention can be produced by, for example, such method as described below.

(1) Synthesis of Intermediate Compound 1: 3-(9,9-dimethyl-9H-fluore-2-yl)-furo[3,4-c]-pyridine-1-(3H)-one

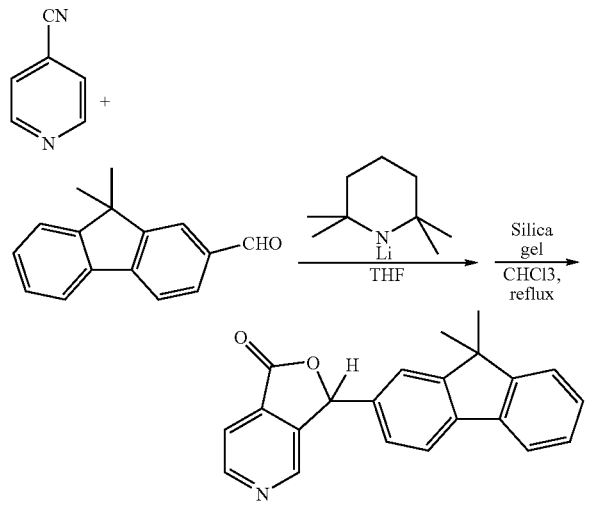

Intermediate Compound 1

Under a nitrogen atmosphere, 4.35 g (30.8 mmol) of 2,2,6,6-tetramethylpiperidine was dissolved in tetrahydrofuran (60 ml) as a solvent, and the solution was cooled to −30° C. After that, 17.5 mL (1.6-mol/L solution, 28.0 mmol) of normal butyllithium was slowly dropped to the solution. After the dropping, the mixture was heated to 0° C., and was stirred for 15 minutes. After that, the mixture was cooled to −70° C. A solution (30 ml) of 1.46 g (14.0 mmol) of isonicotinonitrile in tetrahydrofuran was dropped over 15 minutes to the mixture at −70° C. After the mixture had been stirred at −70° C. for an additional 30 minutes, a solution (15 ml) of 6.24 g (28.1 mmol) of 9,9-dimethyl-9H-fluorene-2-carbaldehyde in tetrahydrofuran was dropped over 10 minutes to the mixture. After having been stirred at −70° C. for an additional 30 minutes, the mixture was slowly heated to 0° C., and water was added to the mixture to stop the reaction. Chloroform was added to the mixture to separate an organic layer, and the layer was washed with water four times. After that, the solvent was removed by distillation, and chloroform (50 ml) and 10 g of silica gel were added to the resultant residue. The mixture was stirred under heat and reflux for 3 hours. After the mixture had been cooled to room temperature, the solvent was removed by distillation again. The resultant residue was purified by silica gel column chromatography (toluene:ethyl acetate=2:1), whereby 2.41 g of Intermediate Compound 1 was obtained.

(2) Synthesis of Exemplified Compound 1308

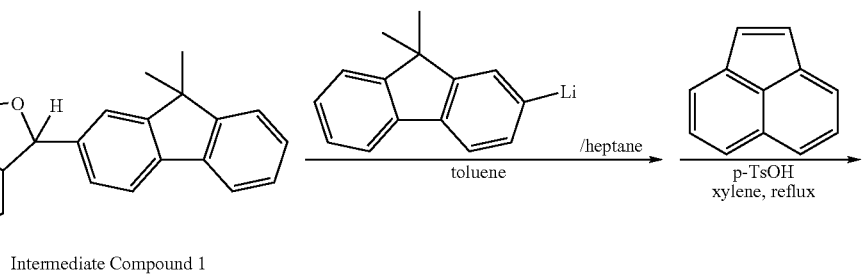

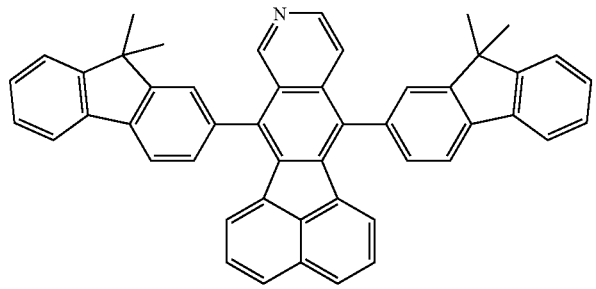

Exemplified Compound 1308

Under a nitrogen atmosphere, 2.94 g (9.19 mmol) of 2-iodo-9,9-dimethyl-9H-fluorene was dissolved in heptane (88 mL), and the solution was cooled to −30° C. After that, 5.7 mL (1.6-mol/L solution, 9.12 mmol) of normal butyllithium was slowly dropped to the solution. After having been stirred at −30° C. for 30 minutes, the mixture was heated to 0° C., and was stirred for 10 minutes. After that, the mixture was cooled to −50° C. A solution (90 mL) of Intermediate Compound 1 (1.48 g, 4.52 mmol) in toluene was dropped to the mixture at −50° C., and the whole was slowly heated to 0° C. After water had been added to the resultant at 0° C. to stop the reaction, 5 mL of acetic acid was added to the resultant. Toluene was added to the resultant to separate an organic layer, and the layer was washed with water twice. After that, the solvent was removed by distillation. Xylene (45 mL) was added to the resultant residue, and then 1.39 g (9.13 mmol) of acenaphthylene and 1.75 g (9.20 mmol) of p-toluenesulfonic monohydrate were added to the residue. Then, the mixture was stirred under heat and reflux for 8 hours. After the mixture had been cooled to room temperature, water was added to the mixture to stop the reaction. Sodium carbonate was added to the mixture, and the whole was repeatedly extracted with chloroform twice, whereby an organic layer was separated. After the organic layer had been washed with water twice, the solvent was removed by distillation. The resultant residue was purified by silica gel column chromatography (toluene: ethyl acetate=30:1), whereby 0.38 g of Exemplified Compound 1308 was obtained.

A mass spectrometer manufactured by Waters Corporation was used to identify 636.3 as the M+ of the compound.

Figure 6:
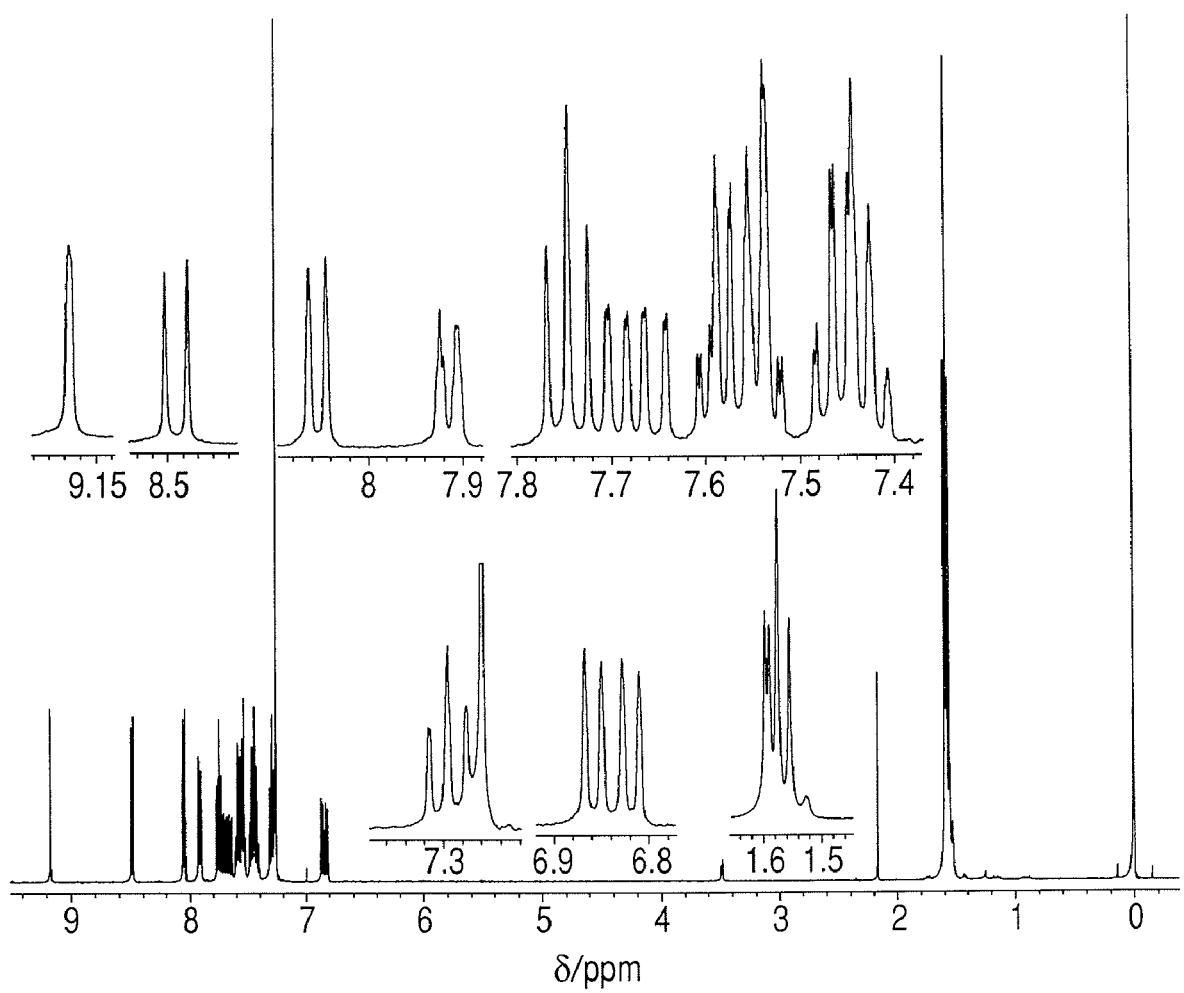
FIG. 6 is a diagram showing the $^1$H-NMR (CDCl$_3$) spectrum of Exemplified Compound 1308.

Further, NMR measurement identified the structure of the compound (FIG. 6).

Figure 13:
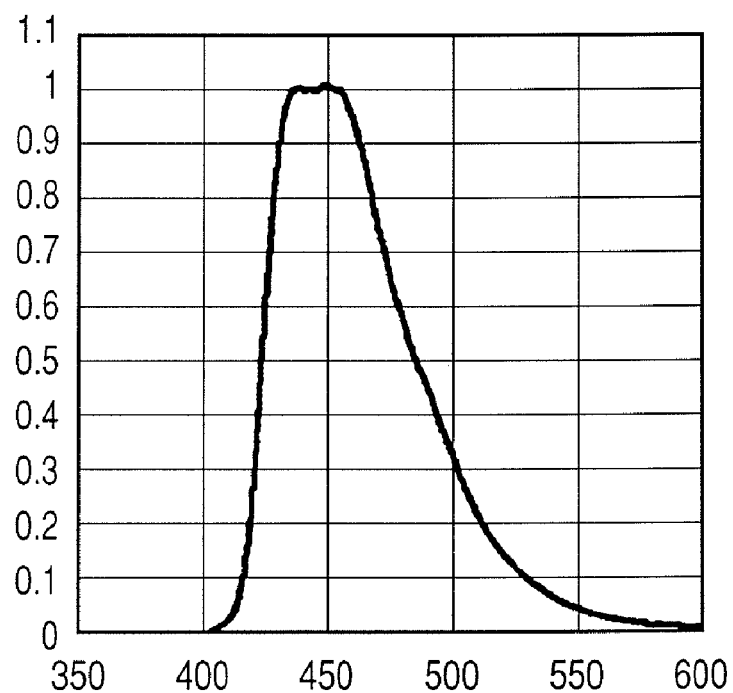
FIG. 13 is a diagram showing the PL spectrum of a solution (1.0×10$^{-5}$ mol/L) of Exemplified Compound 1308 in toluene.

The PL spectrum of a solution ($1.0 \times 10^{-5}$ mol/L) of Exemplified Compound 1308 in toluene was measured. As a result, a blue light emission spectrum having a light emission peak at 435 nm, a half width of 62 nm, and an excellent color purity was shown (FIG. 13).

The following exemplified compound can be synthesized in the same manner as in Example 1 except that the following compound is used instead of 2-iodo-9,9-dimethyl-9H-fluorene in Example 1.

(Exemplified Compound No. 1404): 1-bromo-pyrene

Further, the following exemplified compounds can be synthesized in the same manner as in Example 1 except that the following respective compounds are used instead of 2-iodo-9,9-dimethyl-9H-fluorene and 9,9-dimethyl-9H-fluorene-2-carbaldehyde in Example 1.

(Exemplified Compound No. 1410): 1-bromo-pyrene, pyrene-1-carbaldehyde (Exemplified Compound No. 1425): 3-bromo-fluoranthene, fluoranthene-3-carbaldehyde (Exemplified Compound No. 1322): 4-bromo-2-tert-butyl-9,9-dimethyl-9H-fluorene, 2-tert-butyl-9,9-dimethyl-9H-fluorene-4-carbaldehyde Further, Exemplified Compound No. 2511 can be synthesized in the same manner as in Example 1 except that picolinic acid is used instead of isonicotinonitrile in Example 1.

Example 2

Method of Producing Exemplified Compound No. 1309

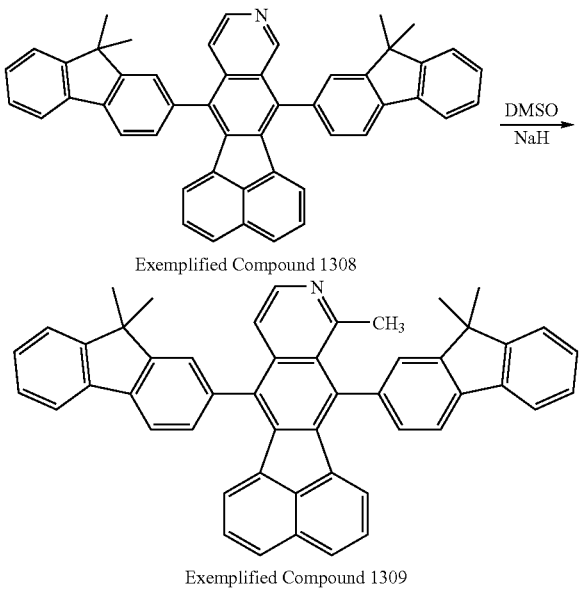

Exemplified Compound 1308

Exemplified Compound 1309

Exemplified Compound No. 1309 can be synthesized by using Exemplified Compound No. 1308 as a starting material in accordance with a method described in J. Org. Chem. 31, 248 (1966). A specific method for the synthesis will be described below.

Under a nitrogen atmosphere, a suspension of sodium hydride in dimethyl sulfoxide is heated to 70° C., and a solution of Exemplified Compound No. 1308 in dimethyl sulfoxide is dropped to the suspension of sodium hydride. After having been stirred at 70° C. for 4 hours, the mixture is cooled to room temperature, and water is added to the mixture to stop the reaction. The mixture is repeatedly extracted with chloroform twice, whereby an organic layer is separated. The solvent is removed by distillation. The resultant residue is purified by silica gel column chromatography (toluene/ethyl acetate-based), whereby Exemplified Compound 1309 can be obtained.

Example 3

Method of Producing Exemplified Compound No. 1303

(1) Synthesis of Intermediate Compound 3: 3-phenylfuro[3,4-c]-pyridine-1-(3H)-one

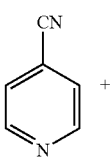

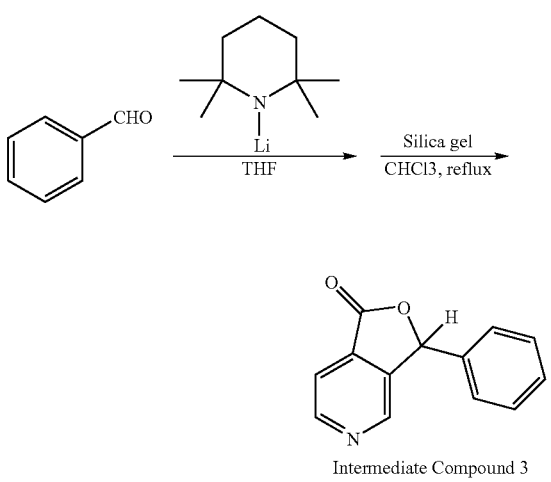

Intermediate Compound 3

Under a nitrogen atmosphere, 14.35 g (105.5 mmol) of 2,2,6,6-tetramethylpiperidine was dissolved in tetrahydrofuran (200 ml) as a solvent, and the solution was cooled to −30° C. After that, 60 mL (1.6-mol/L solution, 96.1 mmol) of normal butyllithium was slowly dropped to the solution. After the dropping, the mixture was heated to 0° C., and was stirred for 15 minutes. After that, the mixture was cooled to −70° C. A solution (100 ml) of 5.00 g (48.0 mmol) of isonicotinonitrile in tetrahydrofuran was dropped over 15 minutes to the mixture at −70° C. After the mixture had been stirred at −70° C. for an additional 30 minutes, a solution (50 ml) of 10.2 g (96.1 mmol) of benzaldehyde in tetrahydrofuran was dropped over 5 minutes to the mixture. After having been stirred at −70° C. for an additional 30 minutes, the mixture was slowly heated to 0° C., and water was added to the mixture to stop the reaction. Chloroform was added to the mixture to separate an organic layer, and the layer was washed with water four times. After that, the solvent was removed by distillation, and chloroform (50 ml) and 35 g of silica gel were added to the resultant residue. The mixture was stirred under heat and reflux for 6 hours, and then stirred under heat and reflux for 3 hours with addition of acetic acid. After the mixture had been cooled to room temperature, the solvent was removed by distillation again. The resultant residue was purified by silica gel column chromatography (toluene:ethyl acetate=8:1), whereby 2.06 g of Intermediate Compound 3 were obtained.

(2) Synthesis of Exemplified Compound 1303

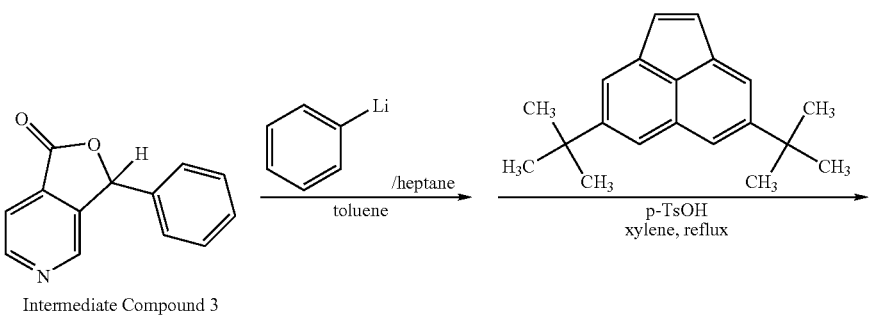

Intermediate Compound 3

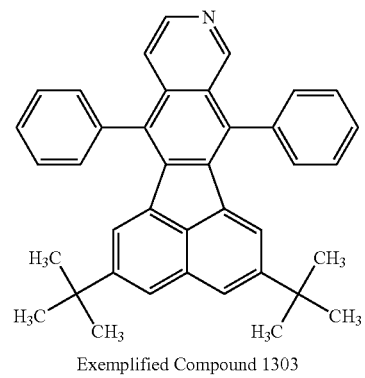

Exemplified Compound 1303

Under a nitrogen atmosphere, 6.3 mL (1.04-mol/L solution, 6.55 mmol) of phenyllithium was dropped to 30 mL of heptane, and the solution was cooled to −50° C. A solution (55 mL) of Intermediate Compound 3 (1.00 g, 4.73 mmol) in toluene was dropped to the mixture at −50° C., and the whole was slowly heated to 0° C. Water was added to the resultant at 0° C. to stop the reaction, and then 5 mL of acetic acid was added to the resultant. The resultant solid product was filtrated and washed with heptane.

Subsequently, the resultant solid product was dissolved in 30 mL of xylene. 2.70 g (14.19 mmol) of p-toluenesulfonic monohydrate and 3.11 g (11.76 mmol) of 4,7-di-t-butylacenaphthylene were added to the solution, and the whole was stirred under heat and reflux for 26 hours. After the resultant had been cooled to room temperature, water was added to the resultant to stop the reaction. Sodium carbonate was added to the resultant, and the whole was repeatedly extracted with chloroform twice, whereby an organic layer was separated. After the organic layer had been washed with water twice, the solvent was removed by distillation. The resultant residue was purified by silica gel column chromatography (toluene:ethyl acetate=20:1), whereby 0.37 g of Exemplified Compound 1303 was obtained.

Figure 7:
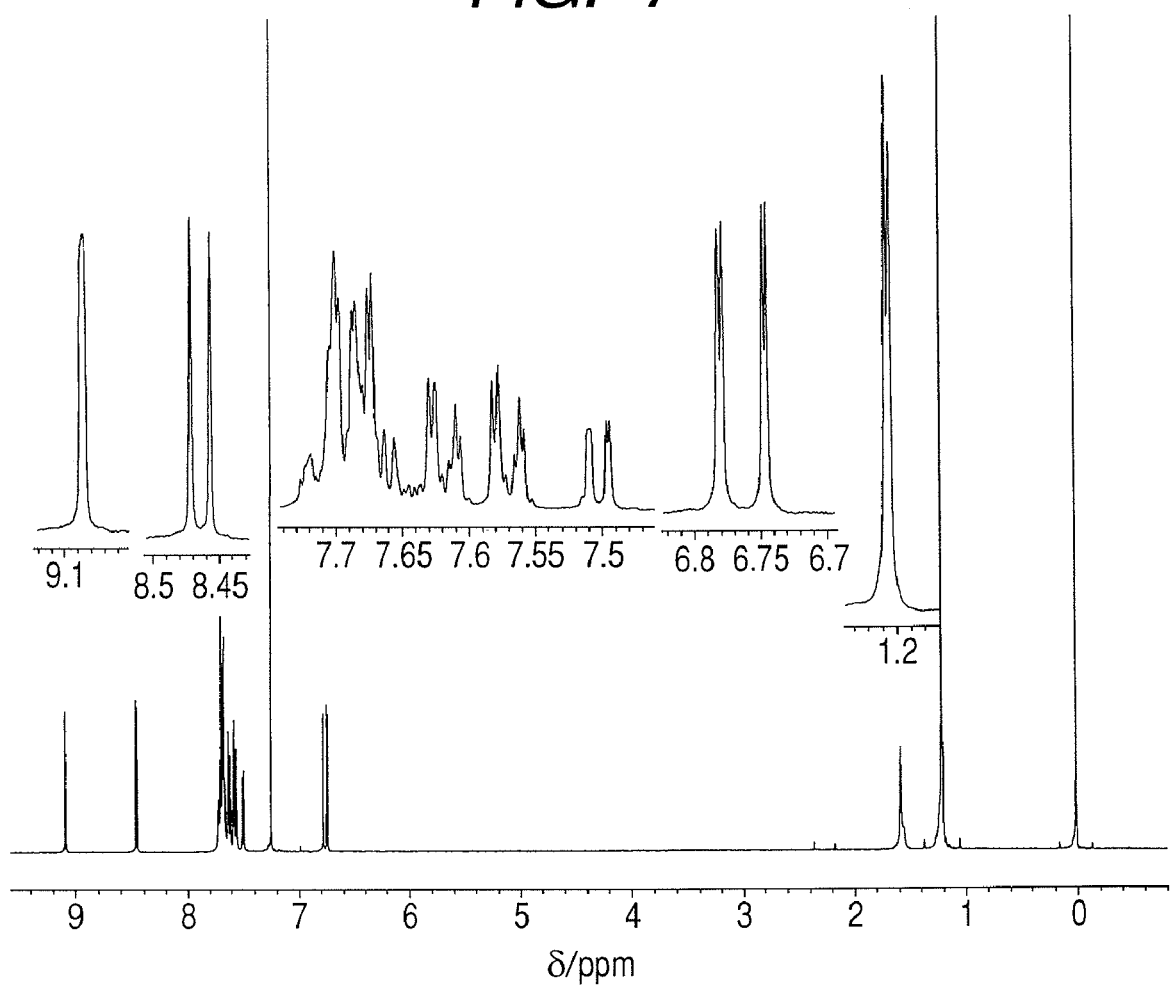
FIG. 7 is a diagram showing the $^1$H-NMR (CDCl$_3$) spectrum of Exemplified Compound 1303.

It should be noted that NMR measurement identified the structure of the compound (FIG. 7).

Figure 14:
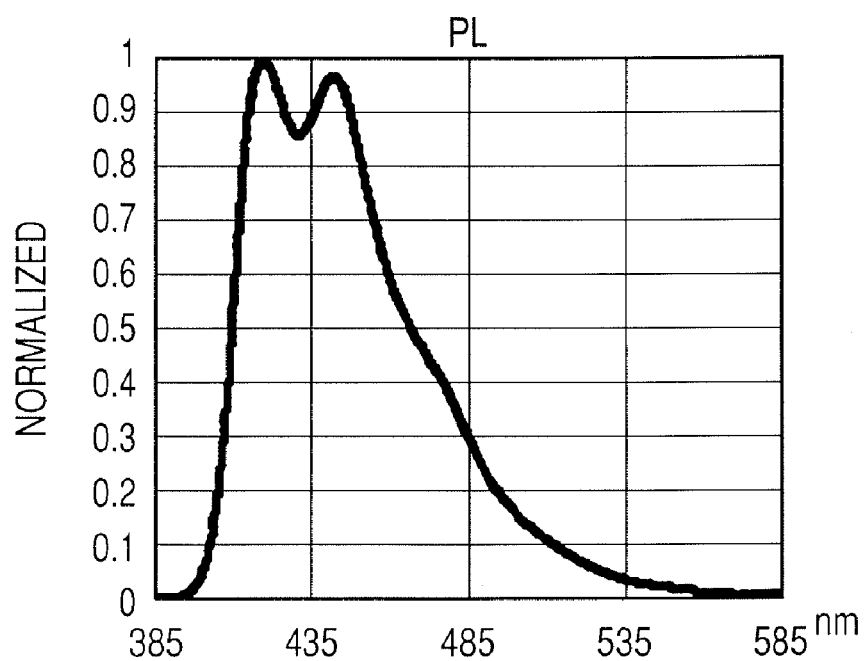
FIG. 14 is a diagram showing the PL spectrum of a solution (1.0×10$^{-5}$ mol/L) of Exemplified Compound 1303 in toluene.

The PL spectrum of a solution ($1.0 \times 10^{-5}$ mol/L) of Exemplified Compound 1303 in toluene was measured. As a result, a blue light emission spectrum having a light emission peak at 422 nm, a half width of 58 nm, and an excellent color purity was shown (FIG. 14).

Example 4

Method of Producing Exemplified Compound No. 1536

(1) Synthesis of Intermediate Compound 4:
4-bromo-7,12-diphenylacenaphtho[1,2-g]isoquinoline
and Intermediate Compound 5:
3-bromo-7,12-diphenylacenaphtho[1,2-g]isoquinoline

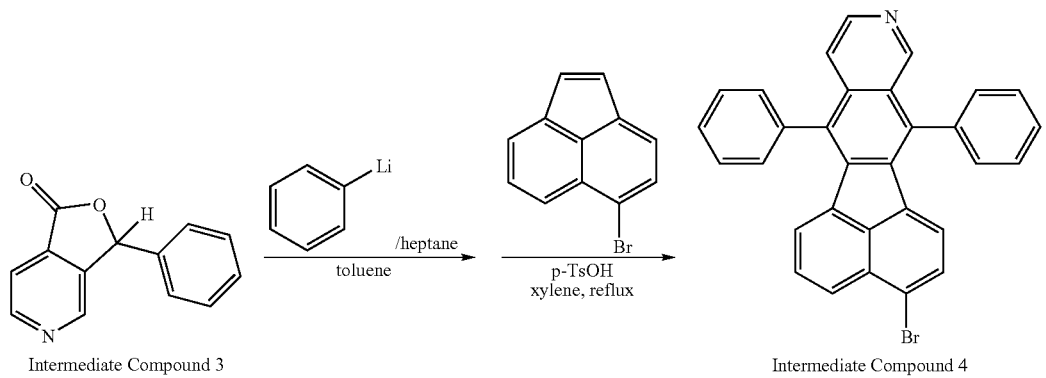

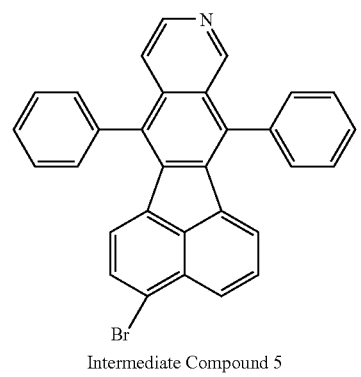

Under a nitrogen atmosphere, 6.3 mL (1.04-mol/L solution, 6.55 mmol) of phenyllithium was dropped to 30 mL of heptane, and the solution was cooled to −50° C. A solution (55 mL) of Intermediate Compound 3 (0.925 g, 4.52 mmol) in toluene was dropped to the mixture at −50° C., and the whole was slowly heated to 0° C. Water was added to the resultant at 0° C. to stop the reaction, and then 5 mL of acetic acid was added to the resultant. The resultant solid product was filtrated and washed with heptane.

Subsequently, the resultant solid product was dissolved in 90 mL of xylene. 4.83 g (25.39 mmol) of p-toluenesulfonic monohydrate and 2.55 g (11.04 mmol) of 5-bromoacenaphthylene were added to the solution, and the whole was stirred under heat and reflux for 30 hours. After the resultant had been cooled to room temperature, water was added to the resultant to stop the reaction. Sodium carbonate was added to the resultant, and the whole was repeatedly extracted with chloroform twice, whereby an organic layer was separated. After the organic layer had been washed with water twice, the solvent was removed by distillation. The resultant residue was purified by silica gel column chromatography (toluene: ethyl acetate=20:1), whereby 0.43 g of the mixture of Intermediate Compounds 4 and 5 (Intermediate Compound 4 Intermediate Compound 5=1:1) was obtained.

Figure 8:
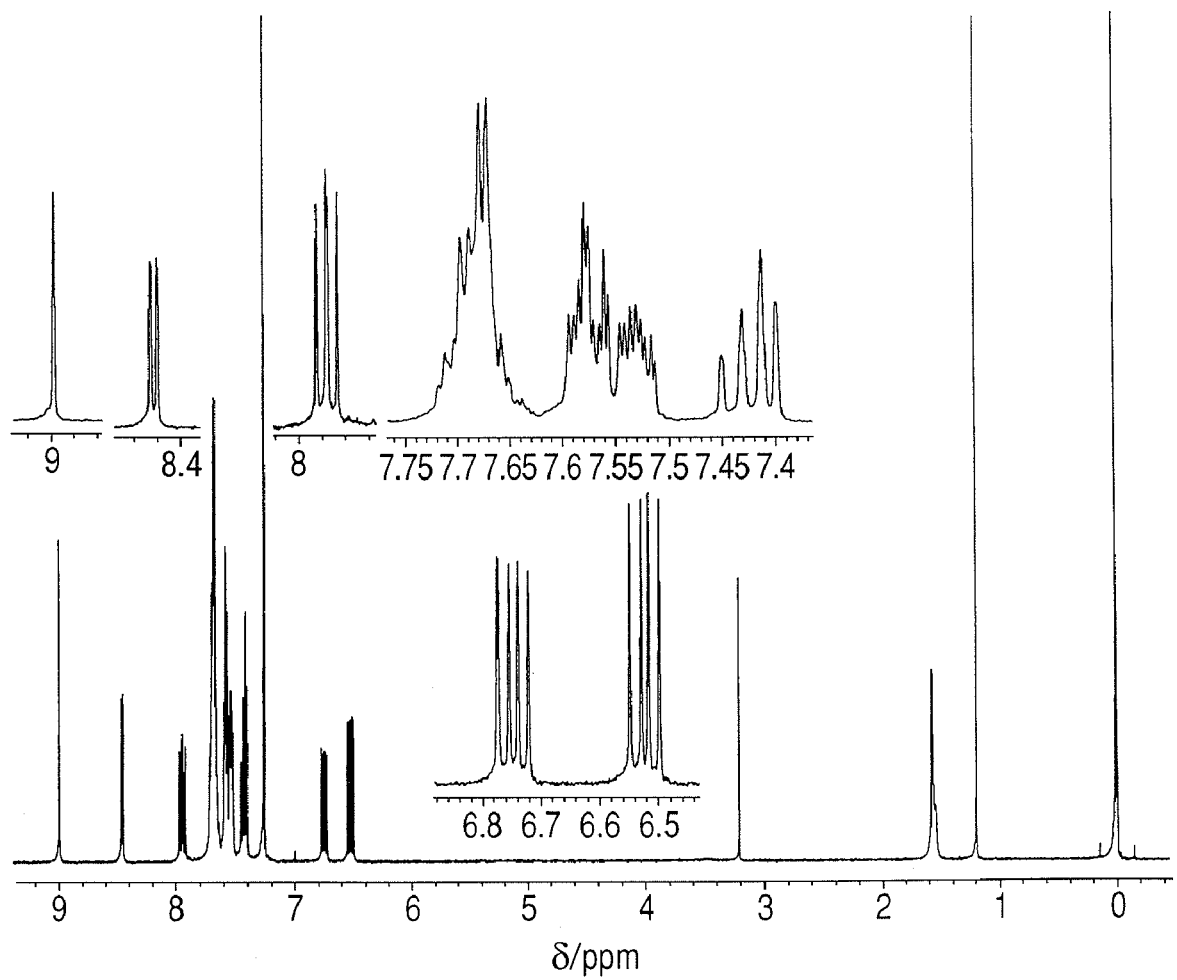
FIG. 8 is a diagram showing the $^1$H-NMR (CDCl$_3$) spectrum of a mixture of Intermediate Compounds 4 and 5.

It should be noted that NMR measurement identified the structure of the compound (FIG. 8).

(2) Synthesis of Exemplified Compound No. 1536

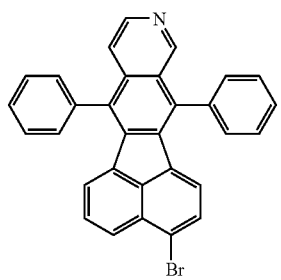

Intermediate Compound 4

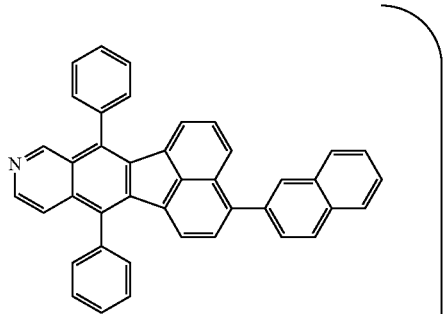

Exemplified Compound 1536-1

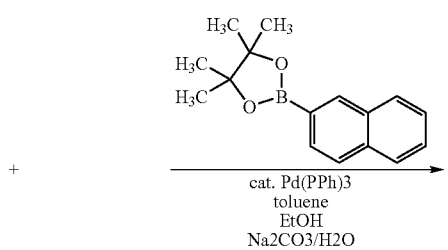

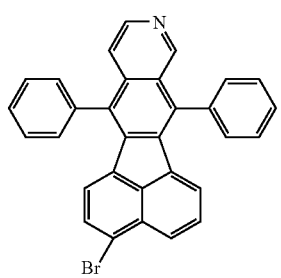

Intermediate Compound 5

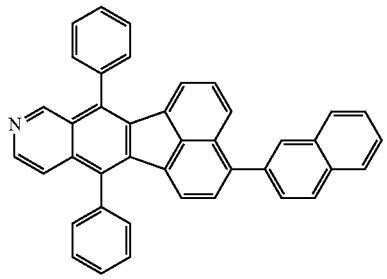

Exemplified Compound 1536-2

Exemplified Compound 1536

Under a nitrogen atmosphere, 0.30 g (0.62 mmol) of the mixture of Intermediate Compounds 4 and 5, 0.11 g (0.62 mmol) of 4,4,5,5-tetramethyl-2-(naphthalen-2-yl)-1,3,2-dioxaborolane, and 0.04 g (0.03 mmol) of tetrakistriphenylphosphinepalladium were suspended in the mixed solvent of 15 mL of toluene, 8 mL of ethanol, and 6 mL of a 10% aqueous solution of sodium carbonate. The resultant solution was stirred under heat and reflux for 1 hour, and the disappearance of Intermediate Compounds 4 and 5 was observed. After that, the resultant was cooled to room temperature, and water was added to the resultant to stop the reaction. An organic layer was separated, and was then washed with water twice. After that, the solvent was removed by distillation. The resultant residue was purified by silica gel column chromatography (toluene:ethyl acetate=10:1), whereby 0.192 g of the mixture of Exemplified Compounds 1536 containing Exemplified Compounds 1536-1 and 1536-2 at a composition ratio of 1:1 was obtained.

Matrix-assisted laser desorption/ionization time-of-flight mass spectrometry (MALDI-TOF MS) identified 531.9 as the $M^+$ of the compound.

Figure 9:
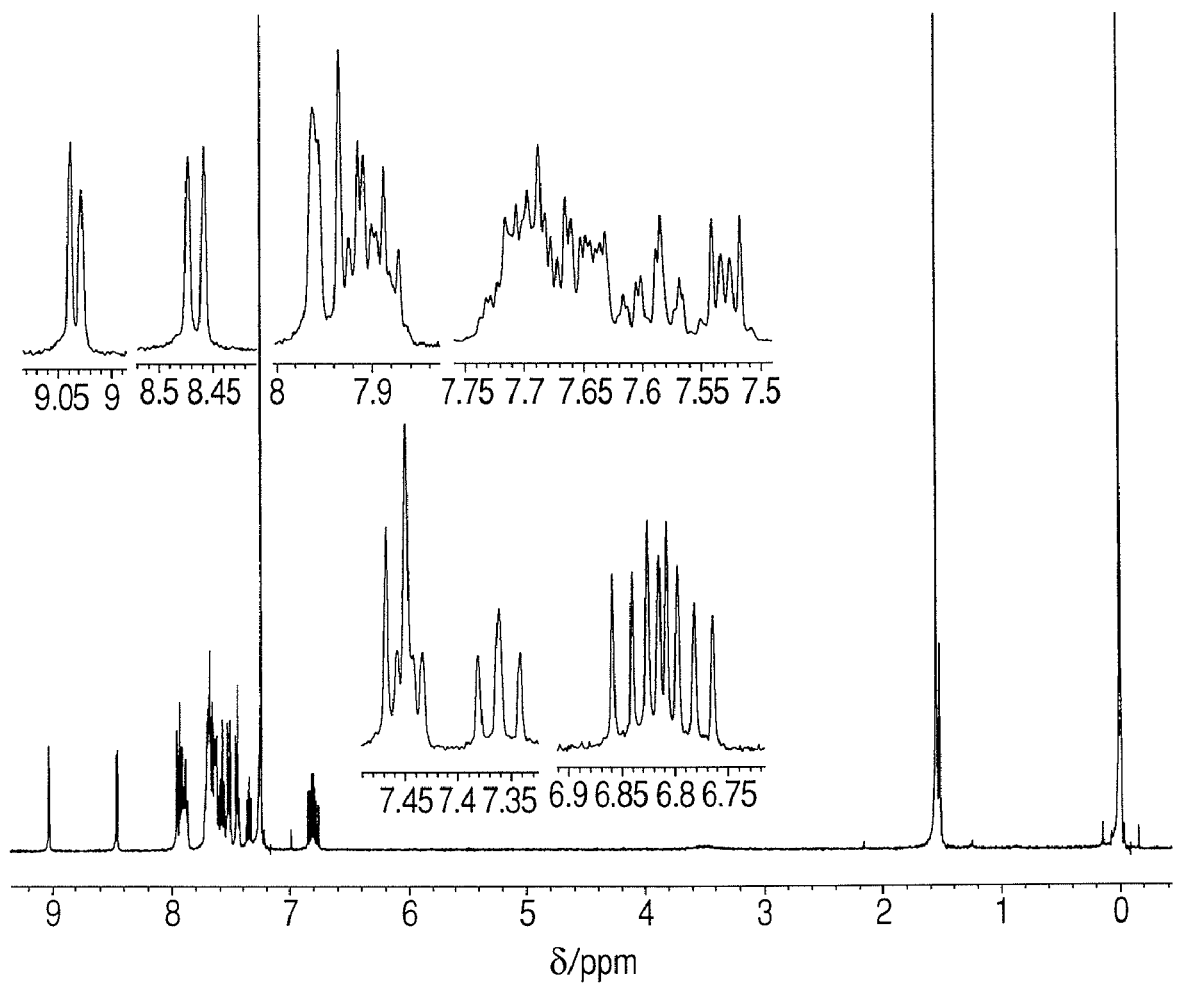
FIG. 9 is a diagram showing the $^1$H-NMR (CDCl$_3$) spectrum of Exemplified Compound 1536.

Further, NMR measurement identified the structure of the compound (FIG. 9).

Figure 15:
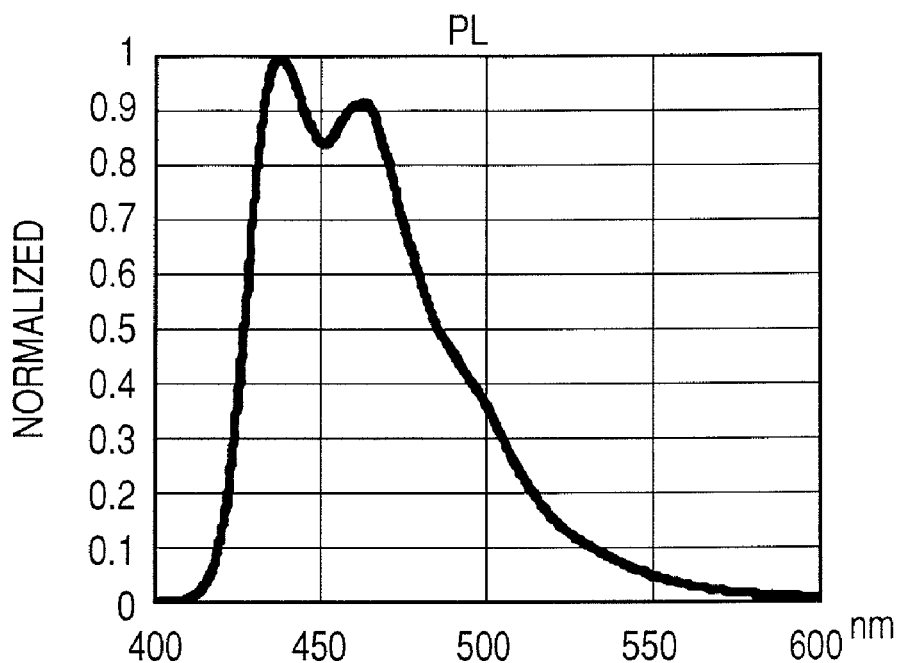
FIG. 15 is a diagram showing the PL spectrum of a solution (1.0×10$^{-5}$ mol/L) of Exemplified Compound 1536 in toluene.

The PL spectrum of a solution ($1.0 \times 10^{-5}$ mol/t) of Exemplified Compound 1536 in toluene was measured. As a result, a blue light emission spectrum having a light emission peak at 439 nm, a half width of 59 nm, and an excellent color purity was shown (FIG. 15).

In addition, Exemplified Compound 2611 can be synthesized in the same manner as in Example 4 except that: picolinic acid is used instead of isonicotinonitrile in Example 4; and 2-(7,12-diphenylbenzo[k]-fluoranthen-3-yl)-4,4,5,5-tetramethyl-1,3,2-dioxaborolane is used instead of 4,4,5,5-tetramethyl-2-(naphthalen-2-yl)-1,3,2-dioxaborolane in Example 4.

In addition, Exemplified Compound No. 3101 can be synthesized in the same manner as in Example 4 except that: pyrimidine-4-carboxylic acid is used instead of isonicotinonitrile in Example 4; and 2-(fluoranthen-3-yl)-4,4,5,5-tetramethyl-1,3,2-dioxaborolane is used instead of 4,4,5,5-tetramethyl-2-(naphthalen-2-yl)-1,3,2-dioxaborolane in Example 4.

In addition, Exemplified Compound 3109 can be synthesized in the same manner as in Example 4 except that: pyrimidine-4-carboxylic acid is used instead of isonicotinonitrile in Example 4; and 2-(7,12-diphenylbenzo[k]-fluoranthen-3-yl)-4,4,5,5-tetramethyl-1,3,2-dioxaborolane is used instead of 4,4,5,5-tetramethyl-2-(naphthalen-2-yl)-1,3,2-dioxaborolane in Example 4.

Example 5

Method of Producing Exemplified Compound No. 1540

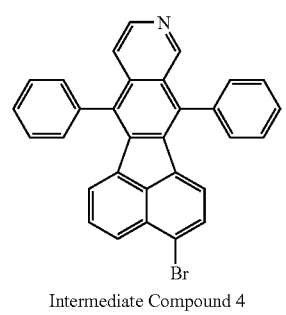

Intermediate Compound 4

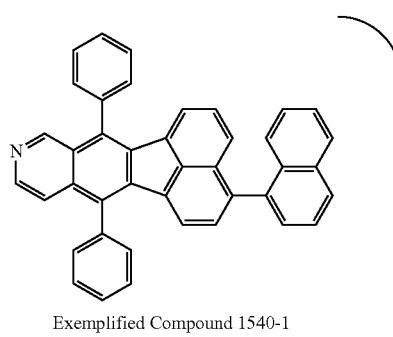

Exemplified Compound 1540-1

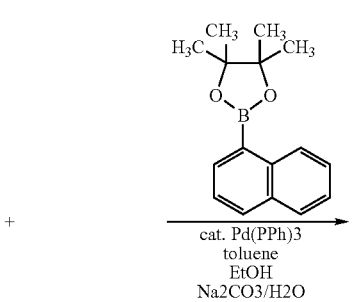

+ cat. Pd(PPh)3
toluene
EtOH
Na2CO3/H2O

Exemplified Compound 1540

-continued

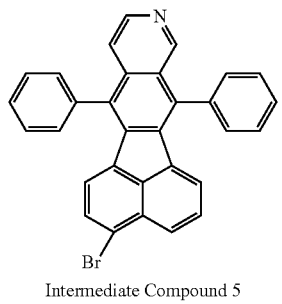
Intermediate Compound 5

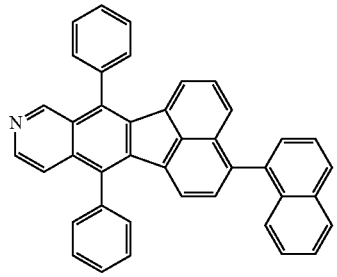
Exemplified Compound 1540-2

Under a nitrogen atmosphere, 0.50 g (1.03 mmol) of the mixture of Intermediate Compounds 4 and 5, 0.19 g (1.10 mmol) of 4,4,5,5-tetramethyl-2-(naphthalen-1-yl)-1,3,2-dioxaborolane, and 0.06 g (0.05 mmol) of tetrakistriphenylphosphinepalladium were suspended in a mixed solvent of 25 mL of toluene, 13 mL of ethanol, and 10 mL of a 10% aqueous solution of sodium carbonate. The resultant solution was stirred under heat and reflux for 2 hours, and the disappearance of Intermediate Compounds 4 and 5 was observed. After that, the resultant was cooled to room temperature, and water was added to the resultant to stop the reaction. An organic layer was separated, and was then washed with water twice. After that, the solvent was removed by distillation. The resultant residue was purified by silica gel column chromatography (toluene:ethyl acetate=10:1), whereby 0.476 g of the mixture of Exemplified Compounds 1540 containing Exemplified Compounds 1540-1 and 1540-2 at a composition ratio of 1:1 was obtained.

Figure 10:
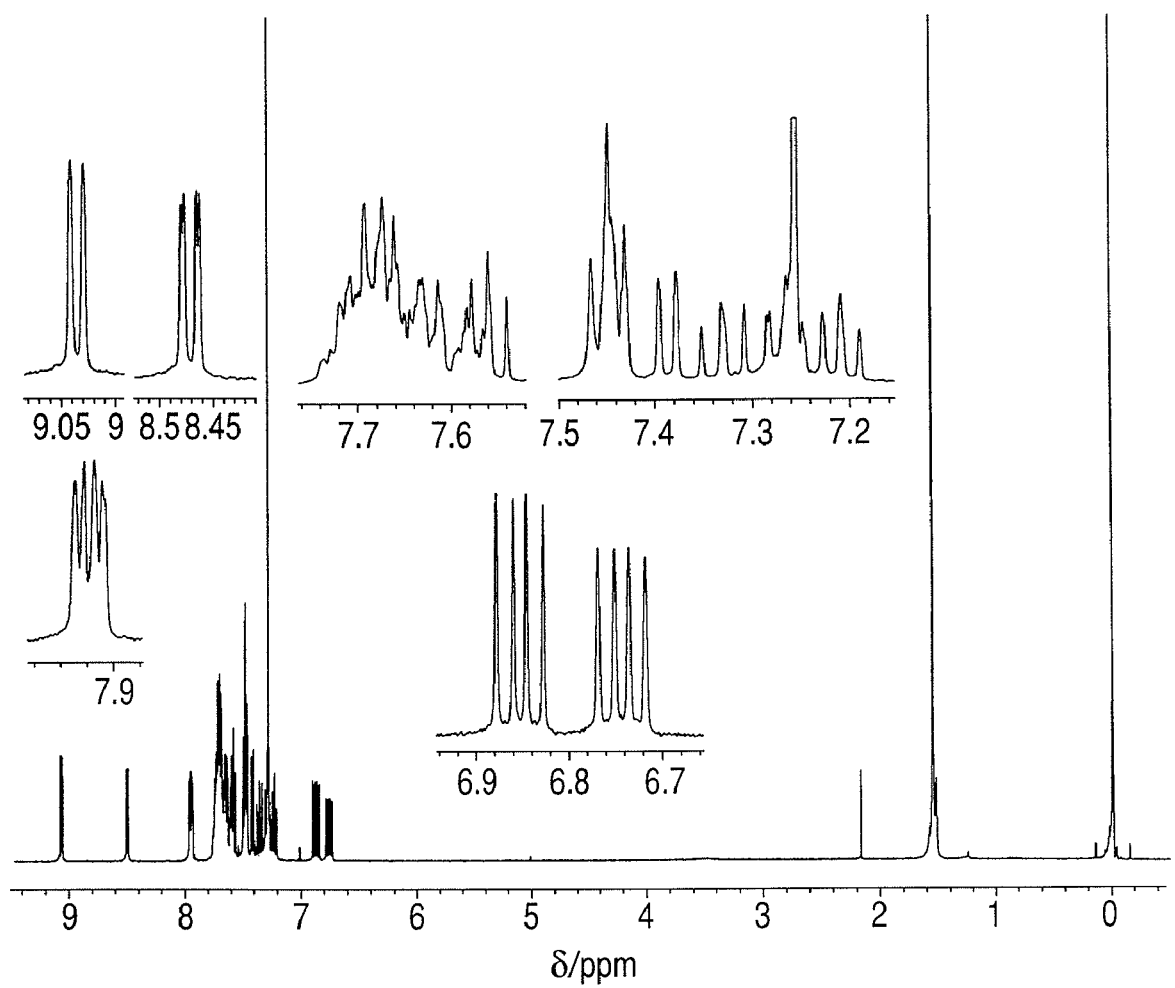
FIG. 10 is a diagram showing the $^1$H-NMR (CDCl$_3$) spectrum of Exemplified Compound 1540.

NMR measurement identified the structure of the compound (FIG. 10).

Figure 16:
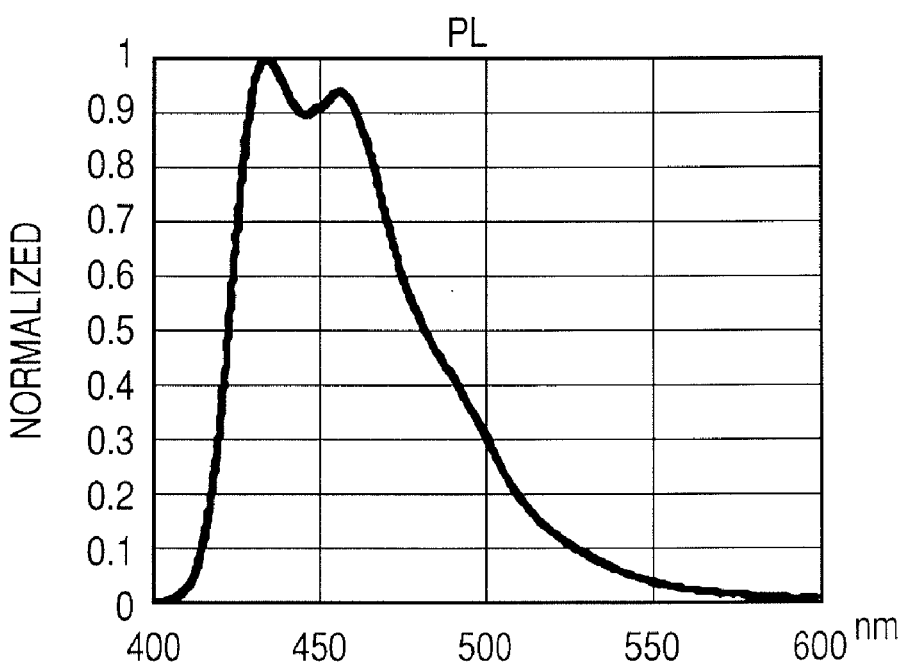
FIG. 16 is a diagram showing the PL spectrum of a solution (1.0×10$^{-5}$ mol/L) of Exemplified Compound 1540 in toluene.

The PL spectrum of a solution ($1.0 \times 10^{-5}$ mol/L) of Exemplified Compound 1540 in toluene was measured. As a result, a blue light emission spectrum having a light emission peak at 434 nm, a half width of 62 nm, and an excellent color purity was shown (FIG. 16).

Example 6

Method of Producing Exemplified Compound No. 1515

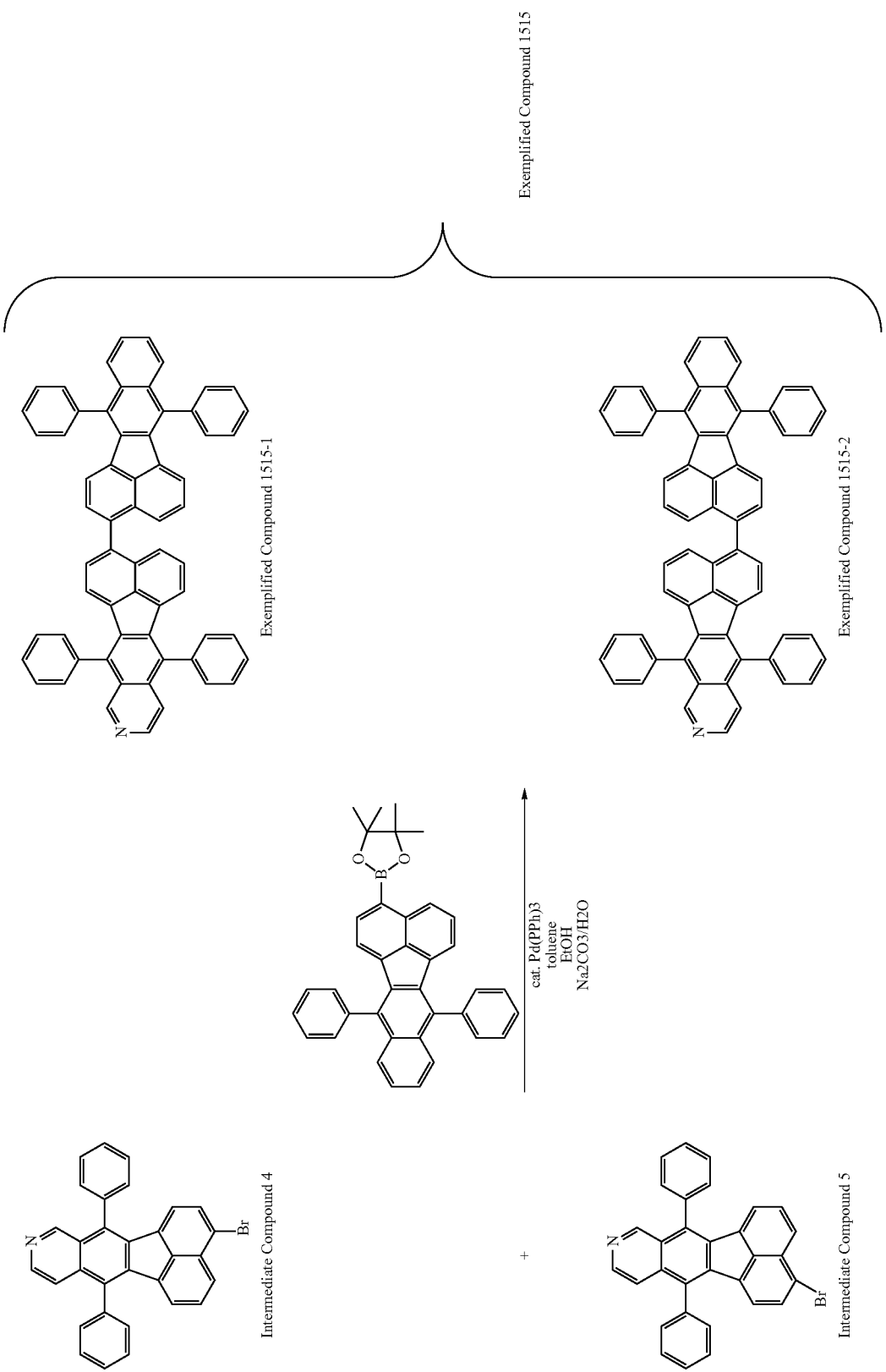

Under a nitrogen atmosphere, 0.30 g (0.62 mmol) of the mixture of Intermediate Compounds 4 and 5, 0.34 g (0.64 mmol) of 2-(7,12-diphenylbenzo[k]-fluoranthen-3-yl)-4,4,5,5-tetramethyl-1,3,2-dioxaborolane, and 0.04 g (0.03 mmol) of tetrakistriphenylphosphinepalladium were suspended in a mixed solvent of 15 mL of toluene, 8 mL of ethanol, and 6 mL of a 10% aqueous solution of sodium carbonate. The resultant solution was stirred under heat and reflux for 2 hours, and the disappearance of Intermediate Compounds 4 and 5 was observed. After that, the resultant was cooled to room temperature, and water was added to the resultant to stop the reaction. An organic layer was separated, and was then washed with water twice. After that, the solvent was removed by distillation. The resultant residue was purified by silica gel column chromatography (toluene:ethyl acetate=10:1), whereby 0.372 g of the mixture of Exemplified Compounds 1515 containing Exemplified Compounds 1515-1 and 1515-2 at a composition ratio of 1:1 was obtained.

Matrix-assisted laser desorption/ionization time-of-flight mass spectrometry (MALDI-TOF MS) identified 807.85 as the $M^+$ of the compound.

Figure 11:
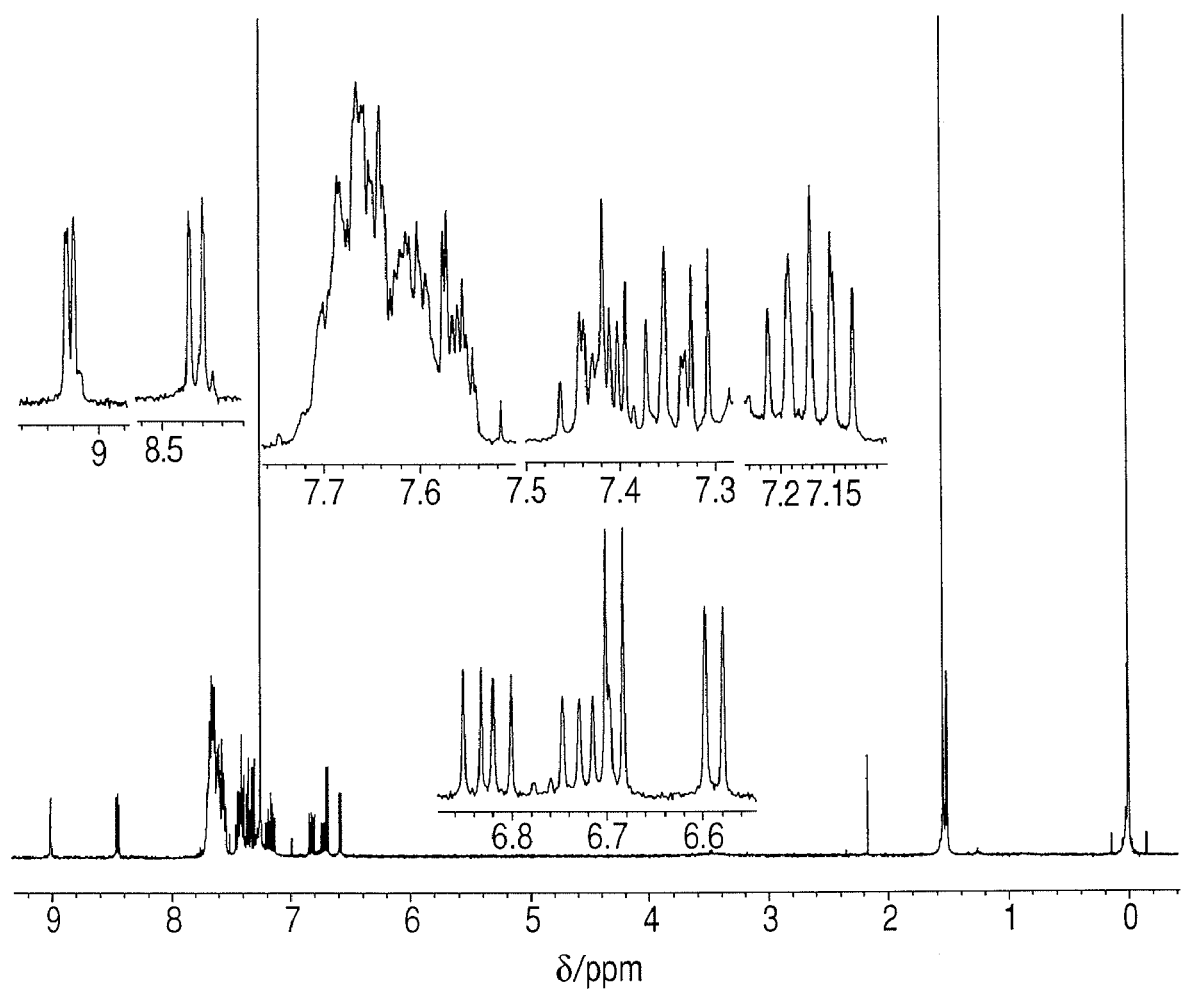
FIG. 11 is a diagram showing the $^1$H-NMR (CDCl$_3$) spectrum of Exemplified Compound 1515.

Further, NMR measurement identified the structure of the compound (FIG. 11).

Figure 17:
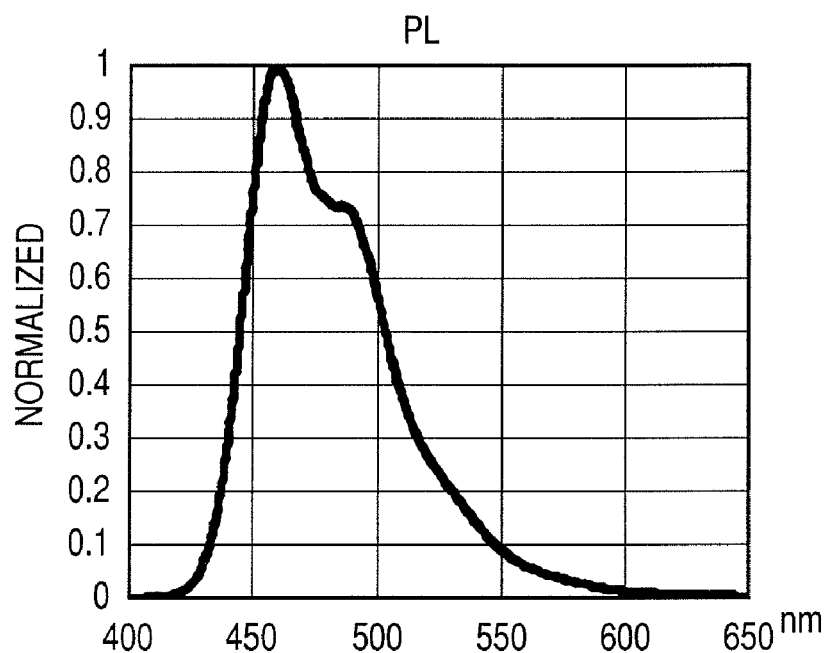
FIG. 17 is a diagram showing the PL spectrum of a solution (1.0×10$^{-5}$ mol/L) of Exemplified Compound 1515 in toluene.
Figure 18:
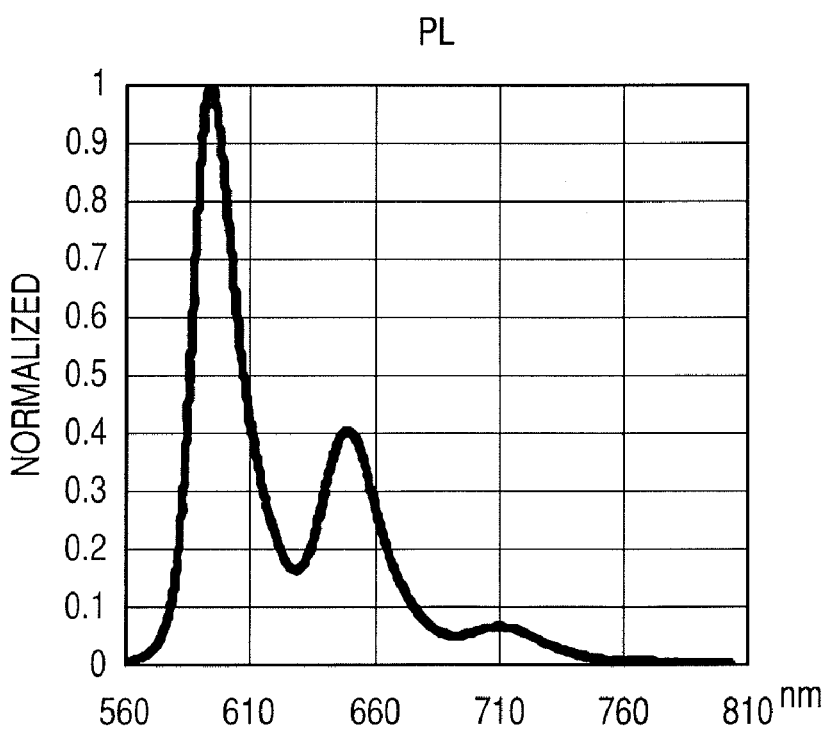
FIG. 18 is a diagram showing the PL spectrum of a solution (1.0×10$^{-5}$ mol/L) of Exemplified Compound 1901 in toluene.

The PL spectrum of a solution ($1.0 \times 10^{-5}$ mol/L) of Exemplified Compound 1515 in toluene was measured. As a result, a blue light emission spectrum having a light emission peak at 461 nm, a half width of 58 nm, and an excellent color purity was shown (FIG. 17).

In addition, each of the following exemplified compounds can be synthesized in the same manner as in Example 6 except that any one of the following compounds is used instead of 2-(7,12-diphenylbenzo[k]-fluoranthen-3-yl)-4,4,5,5-tetramethyl-1,3,2-dioxaborolane in Example 6.

(Exemplified Compound 1501): 2-(fluoranthen-3-yl)-4,4,5,5-tetramethyl-1,3,2-dioxaborolane (Exemplified Compound 1529): 7,12-diphenyl-3-(4,4,5,5-tetramethyl-1,3,2-dioxaborolane-2-yl)-acenaphtho[1,2-g]isoquinoline (Exemplified Compound 1534): 4,4,5,5-tetramethyl-2-(pyren-1-yl)-1,3,2-dioxaborolane)

(Exemplified Compound 1517): 2-(7,12-bis(2,7-di-tert-butyl-9,9-dimethyl-9H-fluoren-4-yl)benzo[k]fluoranthen-3-yl)-4,4,5,5,tetramethyl-1,3,2-dioxaborolane Example 7

Method of Producing Exemplified Compound No. 1901

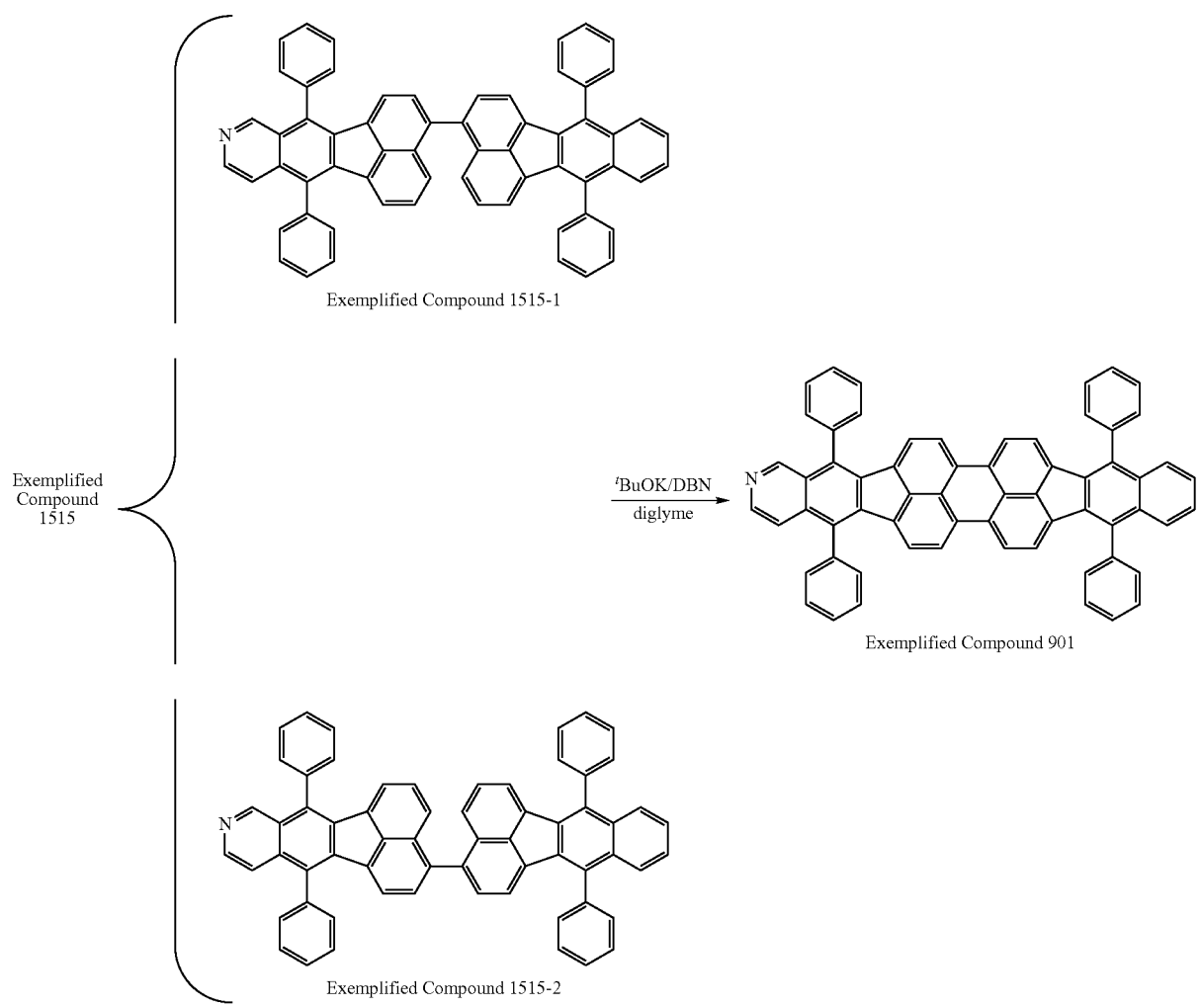

In accordance with a method described in J. Org. Chem. 66, 94 (2001), under a nitrogen atmosphere, 3.03 g (27 mmol) of t-butoxypotassium and 4.47 g (36 mmol) of DBN were added to 9 mL of diglyme, and the whole was stirred under heat and reflux for 1 hour. After that, 0.13 g (1.23 mmol) of Exemplified Compound 1515 was added in one stroke to the resultant, and the whole was stirred under heat and reflux for an additional 2 hours. After having been cooled to room temperature, the resultant was cooled in an ice bath to 5° C., and then water and chloroform were sequentially added to the resultant. An organic layer was separated, and was then washed with a saturated aqueous solution of ammonium chloride twice. After that, the organic layer was additionally washed with water twice, and the solvent was removed by distillation. The resultant residue was purified by alumina column chromatography (toluene ethyl acetate=5:1), whereby 0.80 g of Exemplified Compound 1901 was obtained.

Matrix-assisted laser desorption/ionization time-of-flight mass spectrometry (MALDI-TOF MS) identified 805.31 as the M$^+$ of the compound.

Figure 12:
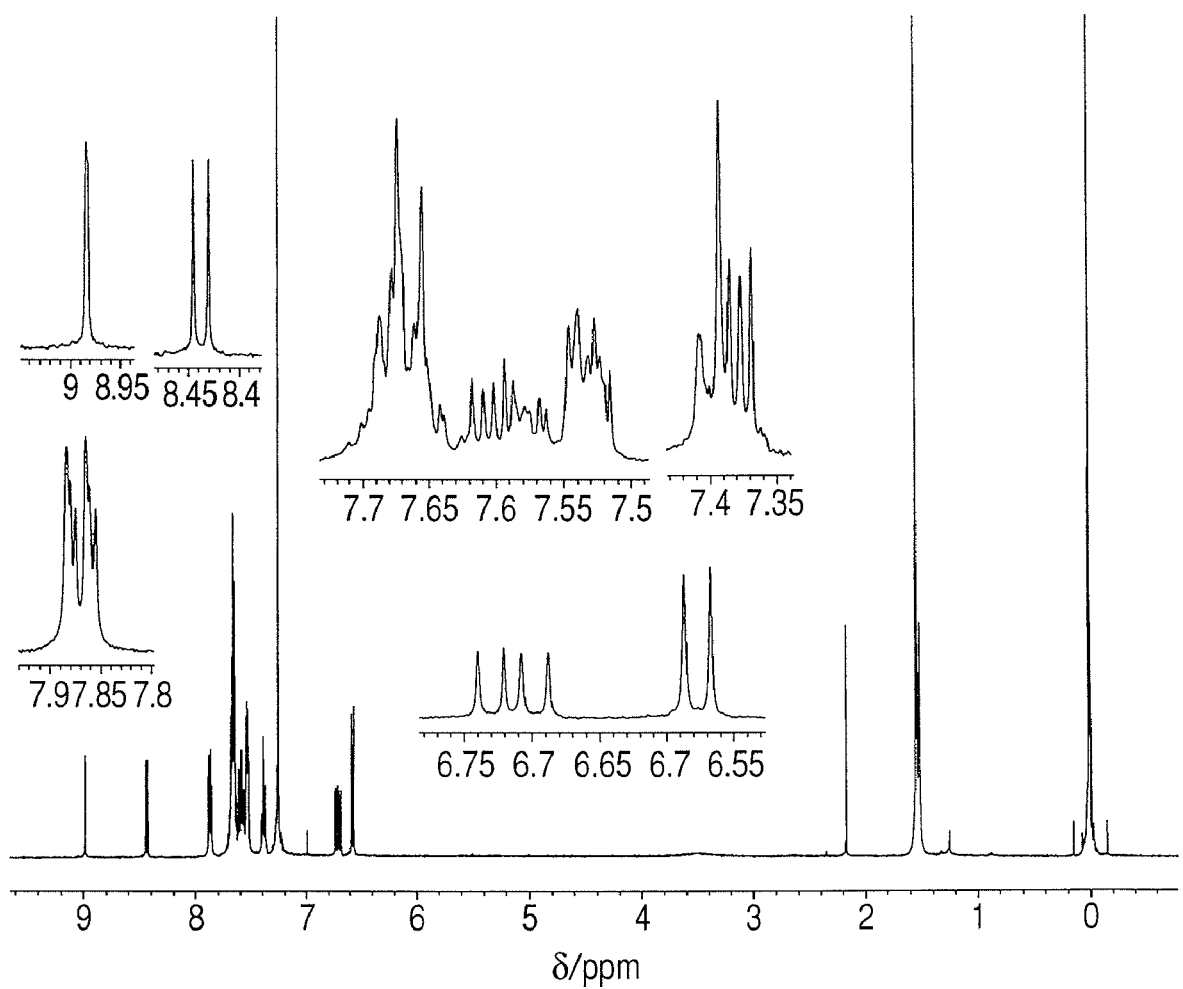
FIG. 12 is a diagram showing the $^1$H-NMR (CDCl$_3$) spectrum of Exemplified Compound 1901.

Further, NMR measurement identified the structure of the compound (FIG. 12).

The PL spectrum of a solution (1.0×10$^{-5}$ mol/L) of Exemplified Compound 1901 in toluene was measured. As a result, a red light emission spectrum having a light emission peak at 597 nm, a half width of 21 nm, and an excellent color purity was shown (FIG. 8).

In addition, the following exemplified compounds can be synthesized in the same manner as in Example 7 except that any one of the following compounds is used instead of Exemplified Compound 1515 in Example 7.

(Exemplified Compound 1701): Exemplified Compound 1501

(Exemplified Compound 1927): Exemplified Compound 1517

(Exemplified Compound 2301): Exemplified Compound 1529

(Exemplified Compound 2321): Exemplified Compound 1308

(Exemplified Compound 2701): Exemplified Compound 2601

(Exemplified Compound 2801): Exemplified Compound 2611

(Exemplified Compound 2919): Exemplified Compound 2511

(Exemplified Compound 3201): Exemplified Compound 3101

(Exemplified Compound 3301): Exemplified Compound 3109

(Exemplified Compound 3413): Exemplified Compound 3008

Example 8

Method of Producing Exemplified Compound No. 3512

Exemplified Compound 3512 of the present invention can be produced by, for example, such method as described below.

(1) Synthesis of Intermediate Compound 6: 3-methoxynaphthalen-2-ylboronic acid

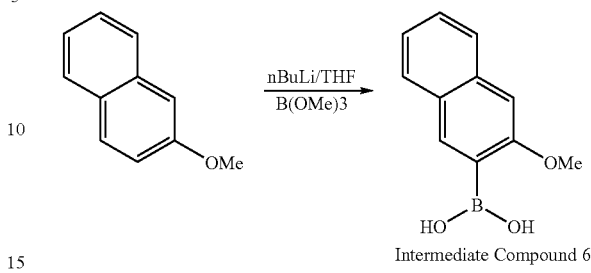
Intermediate Compound 6

Under a nitrogen atmosphere, 15.0 g (94.9 mmol) of 2-methoxynaphthalene was dissolved in tetrahydrofuran (300 ml), and the solution was cooled to 0° C. After that, 238 mL (1.6-mol/L solution, 190 mmol) of normal butyllithium were slowly dropped to the solution. After the dropping, the mixture was stirred at 0° C. for 2 hours. After that, the mixture was cooled to −10° C., and 33 mL (340 mmol) of trimethyl borate was dropped over 10 minutes to the mixture. The resultant was heated to room temperature, and was stirred overnight. After that, 0.2N hydrochloric acid was added to the resultant to stop the reaction. Chloroform was added to the resultant to separate an organic layer, and the layer was washed with a saturated aqueous solution of ammonium chloride once and with water four times. After that, the solvent was removed by distillation, and heptane and toluene were added to the resultant residue to purify the residue by recrystallization, whereby 4.81 g of Intermediate Compound 6 were obtained.

(2) Synthesis of Intermediate Compound 7: 3-hydroxynaphthalen-2-ylboronic acid

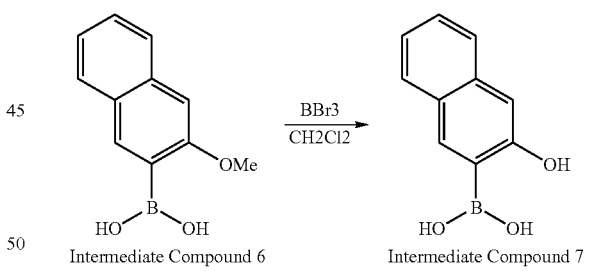
Intermediate Compound 6     Intermediate Compound 7

Under a nitrogen atmosphere, 4.81 g (23.8 mmol) of Intermediate Compound 6 were dissolved in methylene chloride (96 ml), and the solution was cooled to 0° C. After that, 71 mL of a solution of tribromoborate in methylene chloride (1.0-mol/L solution, 71 mmol) were dropped over 15 minutes to the solution. After the dropping, the mixture was heated to room temperature, and was stirred for 5 hours. After that, the reaction solution was transferred to water so that the reaction was stopped. Chloroform was added to the resultant to separate an organic layer, and the layer was washed with water three times. After that, the solvent was removed by distillation, and methanol and heptane were added to the resultant residue to precipitate a crystal. After that, the crystal was filtrated, whereby 3.96 g of Intermediate Compound 7 were obtained.

(3) Synthesis route from Intermediate Compound 7 to Exemplified Compound 3512

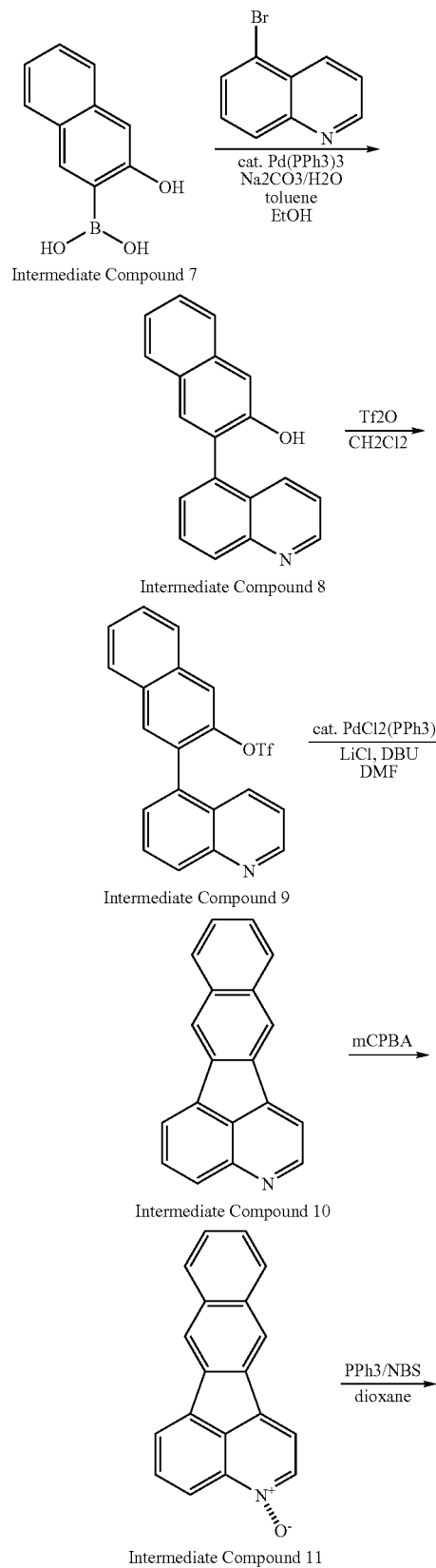

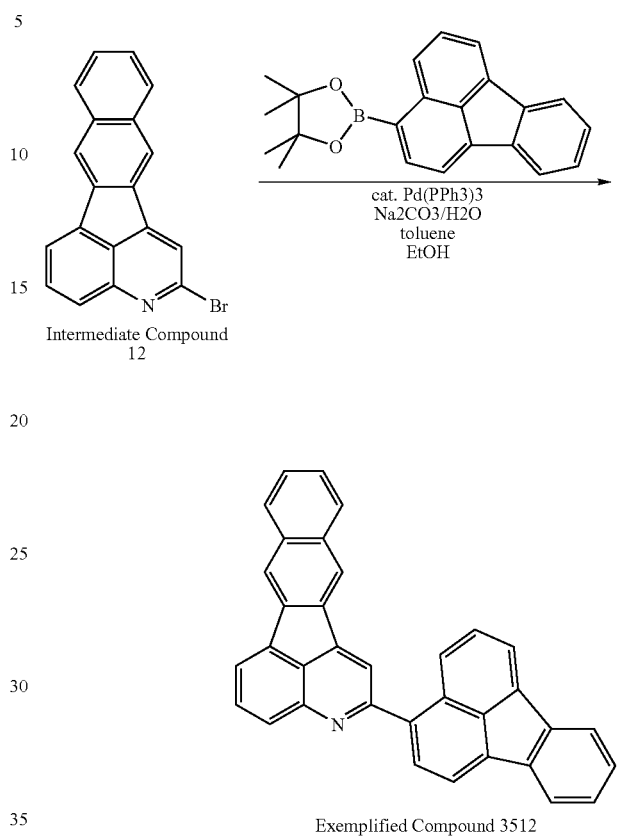

Exemplified Compound 3512 can be synthesized by using Intermediate Compound 7 as a starting material by the above synthesis route through six steps of reactions.

In addition, Exemplified Compound No. 3509 can be synthesized in the same manner as in Example 8 except that 4,4,5,5-tetramethyl-2-(pyren-1-yl)-1,3,2-dioxaborolane is used instead of 2-(fluoranthen-3-yl)-4,4,5,5-tetramethyl-1,3,2-dioxaborolane in Example 8.

Example 9

An organic light emitting device having a structure shown in FIG. 3 was produced by the following method.

Indium tin oxide (ITO) was formed into a film having a thickness of 120 nm by a sputtering method on a glass substrate as the substrate 1 so as to serve as the anode 2, and the resultant was used as a transparent, conductive supporting substrate. The substrate was subjected to ultrasonic cleaning with acetone and isopropyl alcohol (IPA) sequentially. Next, the substrate was washed with pure water and dried. Further, the substrate was subjected to UV/ozone cleaning, and the resultant was used as a transparent, conductive supporting substrate.

A chloroform solution having a concentration of 0.1 wt % was prepared by using Compound 13 represented by the following structural formula as a hole transporting material.

Compound 13

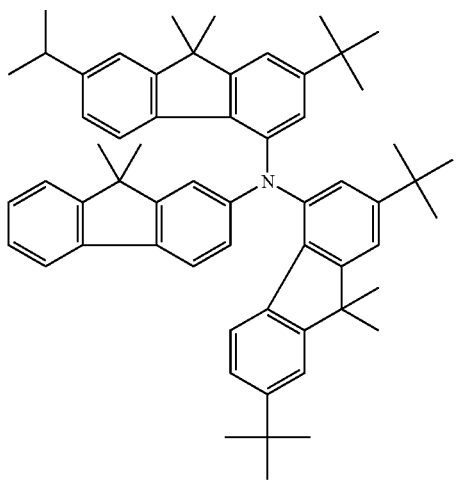

The solution was dropped onto the above ITO electrode, and the whole was subjected to spin coating initially at 500 RPM for 10 seconds and then at 1,000 RPM for 40 seconds, whereby a film was formed. After that, the resultant was dried in a vacuum oven at 80° C. for 10 minutes so that the solvent in the thin film was completely removed. As a result, the hole transporting layer 5 was formed.

Next, Exemplified Compound 1308 shown above and Compound 14 having a structure represented by the following structural formula were co-deposited from the vapor at a weight ratio of 5:95 onto the hole transporting layer 5, whereby the light emitting layer 3 having a thickness of 30 nm was provided. The layer was formed under conditions including a degree of vacuum at the time of the deposition of $1.0×10^{-4}$ Pa and a deposition rate of 0.1 nm/sec or more to 0.2 nm/sec or less.

Compound 14

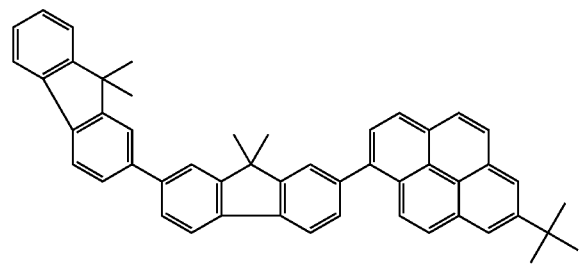

Further, 2,9-bis[2-(9,9-dimethylfluorenyl)]-1,10-phenanthroline was formed into a film having a thickness of 30 nm by a vacuum vapor deposition method to serve as the electron transporting layer 6. The layer was formed under conditions including a degree of vacuum at the time of the deposition of $1.0×10^{-4}$ Pa and a deposition rate of 0.1 nm/sec or more to 0.2 nm/sec or less.

Next, lithium fluoride (LiF) was formed into a film having a thickness of 0.5 nm by a vacuum vapor deposition method on the foregoing organic layer. Further, an aluminum film having a thickness of 100 nm was provided by a vacuum vapor deposition method to serve as an electron injecting electrode (cathode 4), whereby an organic light emitting device was produced. The lithium fluoride film was formed under conditions including a degree of vacuum at the time of the deposition of $1.0×10^{-4}$ Pa and a deposition rate of 0.01 nm/sec. The aluminum film was formed under conditions including a degree of vacuum at the time of the deposition of $1.0×10^{-4}$ Pa and a deposition rate of 0.5 nm/sec or more to 1.0 nm/sec or less.

The resultant organic EL device was covered with a protective glass plate in a dry air atmosphere and sealed with an acrylic resin-based adhesive in order that the device might not deteriorate owing to the adsorption of moisture.

A voltage of 4 V was applied to the device thus obtained with the ITO electrode (anode 2) defined as a positive electrode and the Al electrode (cathode 4) defined as a negative electrode. As a result, the device was observed to emit blue light with a luminous efficiency of 2.0 lm/W. In addition, the device was observed to emit blue light having CIE chromaticity coordinates (x, y) of (0.15, 0.10) and a good color purity.

Further, a voltage was applied to the device for 100 hours under a nitrogen atmosphere with a current density kept at 30 mA/cm². As a result, the initial luminance of the device, that is, 690 cd/m² reduced to 563 cd/m² in 100 hours. This means that luminance deterioration was small.

It should be noted that the energy gap of each of Exemplified Compound 1308 and Compound 14 was determined by optical absorption measurement with a UV measuring device U-3010 manufactured by Hitachi, Ltd. A dilute solution of Exemplified Compound 1308 showed an optical absorption end at 426 nm. The energy gap of the compound was calculated to be 2.91 eV from the foregoing. A spin-coated film of Compound 14 showed an optical absorption end at 417 nm. The energy gap of the compound was calculated to be 2.97 eV from the foregoing.

Example 10

A device was produced in the same manner as in Example 9 except that Compound 15 having a structure represented by the following formula was used instead of Compound 14 in Example 9.

Compound 15

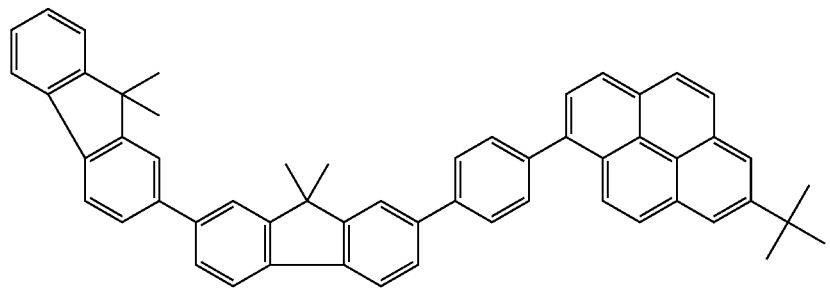

The device of this example was observed to emit blue light with a luminous efficiency of 2.2 lm/W at an applied voltage of 4 V. In addition, the device was observed to emit blue light having CIE chromaticity coordinates (x, y) of (0.15, 0.10) and a good color purity.

Further, a voltage was applied to the device for 100 hours under a nitrogen atmosphere with a current density kept at 30 mA/cm$^2$. As a result, the initial luminance of the device, that is, 931 cd/m$^2$ reduced to 690 cd/m$^2$ in 100 hours. This means that luminance deterioration was small.

It should be noted that the energy gap of Compound 15 was determined by optical absorption measurement with a UV measuring device U-3010 manufactured by Hitachi, Ltd. A spin-coated film of Compound 15 showed an optical absorption end at 405 nm. The energy gap of the compound was calculated to be 3.06 eV from the foregoing.

Example 11

An organic light emitting device having a structure shown in FIG. 4 was produced by the following method.

Indium tin oxide (ITO) was formed into a film having a thickness of 120 nm by a sputtering method on a glass substrate as the substrate 1 so as to serve as the anode 2, and the resultant was used as a transparent, conductive supporting substrate. The substrate was subjected to ultrasonic cleaning with acetone and isopropyl alcohol (IPA) sequentially. Next, the substrate was washed with pure-water and dried. Further, the substrate was subjected to UV/ozone cleaning, and the resultant was used as a transparent, conductive supporting substrate.

A chloroform solution having a concentration of 0.1 wt % was prepared by using Compound 16 represented by the following structural formula as a hole transporting material.

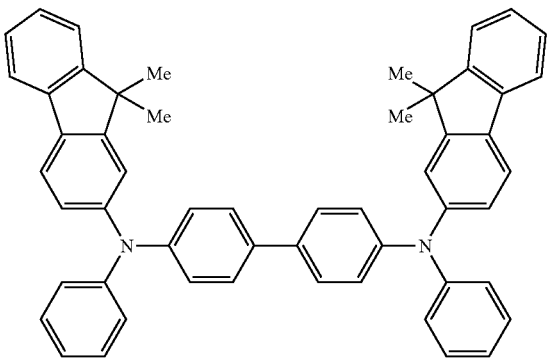

Compound 16

The solution was dropped onto the above ITO electrode, and the whole was subjected to spin coating initially at 500 RPM for 10 seconds and then at 1,000 RPM for 40 seconds, whereby a film was formed. After that, the resultant was dried in a vacuum oven at 80° C. for 10 minutes so that the solvent in the thin film was completely removed. As a result, the hole injecting layer 7 was formed. Next, Compound 13 shown above was formed into a film having a thickness of 15 nm by a vacuum vapor deposition method on the hole injecting layer 7 so as to serve as the hole transporting layer 5.

Exemplified Compound 1303 and Compound 17 having a structural represented by the following structure formula were co-deposited from the vapor at a weight ratio of 5:95 onto the hole transporting layer 5, whereby the light emitting layer 3 having a thickness of 30 nm was provided. The layer was formed under conditions including a degree of vacuum at the time of the deposition of 1.0×10$^{-4}$ Pa and a deposition rate of 0.1 nm/sec or more to 0.2 nm/sec or less.

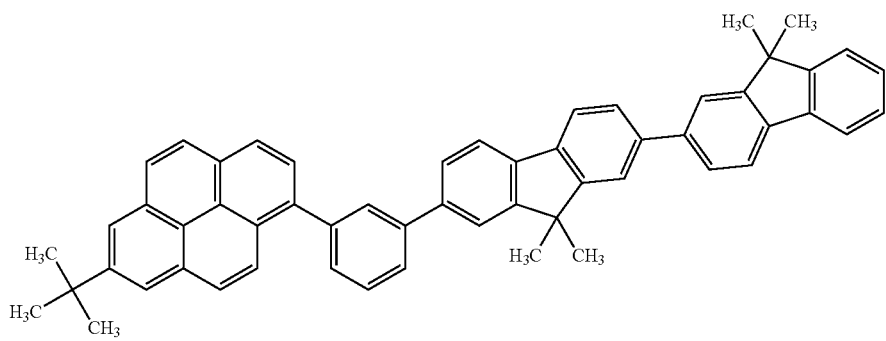

Compound 17

Further, 2,9-bis[2-(9,9'-dimethylfluorenyl)]-1,10-phenanthroline was formed into a film having a thickness of 30 nm by a vacuum vapor deposition method to serve as the electron transporting layer 6. The layer was formed under conditions including a degree of vacuum at the time of the deposition of $1.0 \times 10^{-4}$ Pa and a deposition rate of 0.1 nm/sec to 0.2 nm/sec.

Next, lithium fluoride (LiF) was formed into a film having a thickness of 0.5 nm by a vacuum vapor deposition method on the foregoing organic layer. Further, an aluminum film having a thickness of 100 nm was provided by a vacuum vapor deposition method to serve as an electron injecting electrode (cathode 4), whereby an organic light emitting device was produced. The lithium fluoride film was formed under conditions including a degree of vacuum at the time of the deposition of $1.0 \times 10^{-4}$ Pa and a deposition rate of 0.01 nm/sec. The aluminum film was formed under conditions including a degree of vacuum at the time of the deposition of $1.0 \times 10^{-4}$ Pa and a deposition rate of 0.5 nm/sec to 1.0 nm/sec.

The resultant organic EL device was covered with a protective glass plate in a dry air atmosphere and sealed with an acrylic resin-based adhesive in order that the device might not deteriorate owing to the adsorption of moisture.

A voltage of 4.9 V was applied to the device thus obtained with the ITO electrode (anode 2) defined as a positive electrode and the Al electrode (cathode 4) defined as a negative electrode. As a result, the device was observed to emit blue light with a luminous efficiency of 1.39 lm/W. In addition, the device was observed to emit blue light having CIE chromaticity coordinates (x, y) of (0.15, 0.08) and a good color purity.

It should be noted that the energy gap of each of Exemplified Compound 1303 and Compound 17 was determined by optical absorption measurement with a UV measuring device U-3010 manufactured by Hitachi, Ltd. A dilute solution of Exemplified Compound 1303 showed an optical absorption end of the dilute solution at 419 nm. The energy gap of the compound was calculated to be 2.96 eV from the foregoing. A spin-coated film of Compound 17 showed an optical absorption end at 390 nm. The energy gap of the compound was calculated to be 3.18 eV from the foregoing.

Example 12

A device was produced in the same manner as in Example 11 except that: Compound 14 shown above was used instead of Compound 17 in Example 11; and Exemplified Compound 1536 was used instead of Exemplified Compound 1303 in Example 11. The device of this example was observed to emit blue light with a luminous efficiency of 2.65 lm/W at an applied voltage of 4.7 V. In addition, the device was observed to emit blue light having CIE chromaticity coordinates (x, y) of (0.14, 0.13) and a good color purity.

Further, a voltage was applied to the device for 100 hours under a nitrogen atmosphere with a current density kept at 30 mA/cm$^2$. As a result, the initial luminance of the device, that is, 1178 cd/m$^2$ reduced to 1021 cd/m$^2$ in 100 hours. This means that luminance deterioration was small.

It should be noted that the energy gap of Exemplified Compound 1536 was determined by optical absorption measurement with a UV measuring device U-3010 manufactured by Hitachi, Ltd. A spin-coated film of Exemplified Compound 1536 showed an optical absorption end of the dilute solution at 438 nm. The energy gap of the compound was calculated to be 2.83 eV from the foregoing.

Example 13

A device was produced in the same manner as in Example 11 except that: Compound 14 shown above was used instead of Compound 17 in Example 11; Exemplified Compound 1515 was used instead of Exemplified Compound 1303 in Example 11; and Compound 14 and Exemplified Compound 1515 were co-deposited from the vapor at a weight ratio of 2:98.

The device of this example was observed to emit blue light with a luminous efficiency of 5.03 lm/W at an applied voltage of 4.4 V. In addition, the device was observed to emit blue light having CIE chromaticity coordinates (x, y) of (0.14, 0.21) and a good color purity.

Further, a voltage was applied to the device for 100 hours under a nitrogen atmosphere with a current density kept at 30 mA/cm$^2$. As a result, the initial luminance of the device, that is, 2118 cd/m$^2$ reduced to 2031 cd/m$^2$ in 100 hours. This means that luminance deterioration was small.

It should be noted that the energy gap of Exemplified Compound 1515 was determined by optical absorption measurement with a UV measuring device U-3010 manufactured by Hitachi, Ltd. A spin-coated film of Exemplified Compound 1515 showed an optical absorption end of the dilute solution at 454 nm. The energy gap of the compound was calculated to be 2.73 eV from the foregoing.

COMPARATIVE EXAMPLE 1

A device was produced in the same manner as in Example 10 except that Compound 18 having a structure represented by the following formula was used instead of Exemplified Compound 1308 in Example 10.

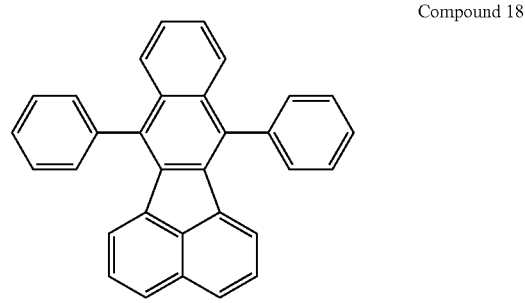

Compound 18

The device of this example was observed to emit light with a luminous efficiency of 1.9 lm/W at an applied voltage of 4 V.

Further, a voltage was applied to the device for 20 hours under a nitrogen atmosphere with a current density kept at 30 mA/cm$^2$. As a result, the initial luminance of the device, that is, 840 cd/m$^2$ reduced to 406 cd/m$^2$, which was half or less as high as the initial luminance, in 20 hours.

Example 14

The results of the measurement of the oxidation-reduction potential of each of the following compounds by a cyclic voltammetry method are shown in the following table.
Guest used in the light emitting layer of Example 10 (Exemplified Compound 1308)
Guest used in the light emitting layer of Comparative Example 1 (Compound 18)
Host commonly used in the light emitting layers of Example 10 and Comparative Example 1 (Compound 15)
It should be noted that the measurement was performed in a solution of each of the compounds in N,N-dimethylformamide having a concentration of $1\times10^{-4}$ mol/L or more to $1\times10^{-6}$ mol/L or less under the following conditions.

Supporting electrolyte: 0.1-mol/L tetrabutyl ammonium perchlorate
Temperature: 25° C.
Reference electrode: $Ag/AgNO_3$
Counter electrode: platinum electrode
Working electrode: glassic carbon

| Compound | $E_{red}$/VvsAg/Ag$^+$ | Relative durable time |
|---|---|---|
| Exemplified Compound 1308 | −2.03 | 1 |
| Compound 18 | −2.17 | 0.06 |
| Compound 15 | −2.37 | |

The results of Table 1, and the results of Example 10 and Comparative Example 1 show that a difference in reduction potential between a host material and a guest material to be used in the light emitting layer of an organic electroluminescence device is related to a reduction in deterioration of the device due to energization. That is, Exemplified Compound 1308 as a guest used in a light emitting layer has a reduction potential of −2.03 V, which is higher than the reduction potential of Compound 18, that is, −2.17 V. In addition, Exemplified Compound 1308 is a material having an electron affinity larger than that of Compound 18 and excellent in durability because a difference in reduction potential between the common host used in light emitting layers and Exemplified Compound 1308 is as large as 0.34 V. It has been found that when Compound 15 is used as a host material, high luminance can be maintained for a long time period, and the deterioration of a light emitting device using the compound due to energization at a constant current can be reduced by combining Exemplified Compound 1308 as a guest material having a reduction potential higher than that of the host material by 0.3 V or more with the host material in the light emitting layer of the device.

Example 15

Method of Producing Exemplified Compound No. 1635

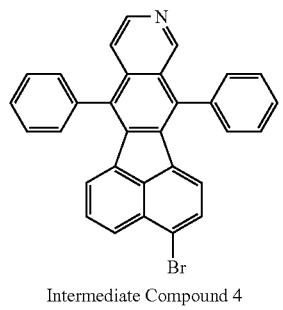

Intermediate Compound 4

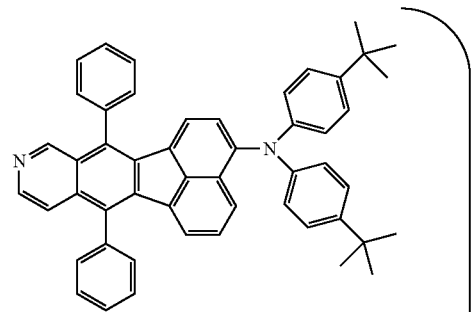

Exemplified Compound 1635-1

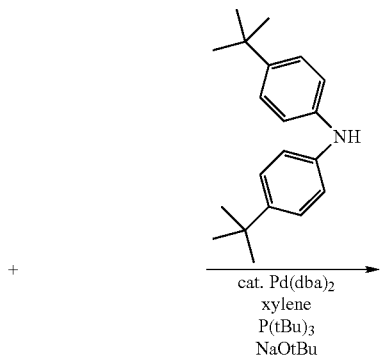

+ cat. Pd(dba)$_2$
xylene
P(tBu)$_3$
NaOtBu

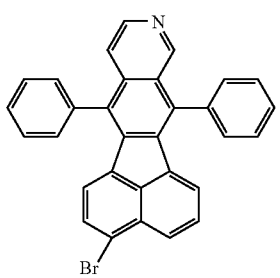

Intermediate Compound 5

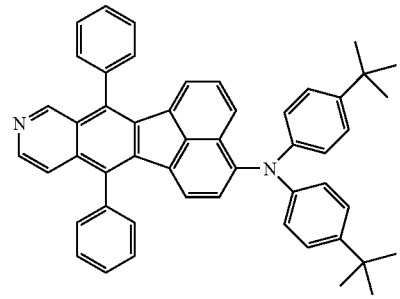

Exemplified Compound 1635-2

Exemplified Compound 1635

Under a nitrogen atmosphere, 0.192 g (2.0 mmol) of t-butoxysodium, 0.48 g (1.0 mmol) of the mixture of Intermediate Compounds 4 and 5, 0.44 g (1.50 mmol) of di-4-t-butylphenylamine, 0.10 g of bisdibenzylidene acetone palladium, and 0.050 g of tri-t-butylphosphine were suspended in 100 mL of xylene. The resultant solution was stirred under heat and reflux for 5 hours, and the disappearance of Intermediate Compounds 4 and 5 was observed. After that, the resultant was cooled to room temperature, and water was added to the resultant to stop the reaction. An organic layer was separated, and was then washed with water twice. After that, the solvent was removed by distillation. The resultant residue was purified by silica gel column chromatography (toluene:heptane=1:1), whereby 0.483 g of the mixture of Exemplified Compounds 1653 containing Exemplified Compounds 1653-1 and 1653-2 at a composition ratio of 1:1 was obtained.

Matrix-assisted laser desorption/ionization time-of-flight mass spectrometry (MALDI-TOF MS) identified 684 as the M+ of the compound.

Figure 19:
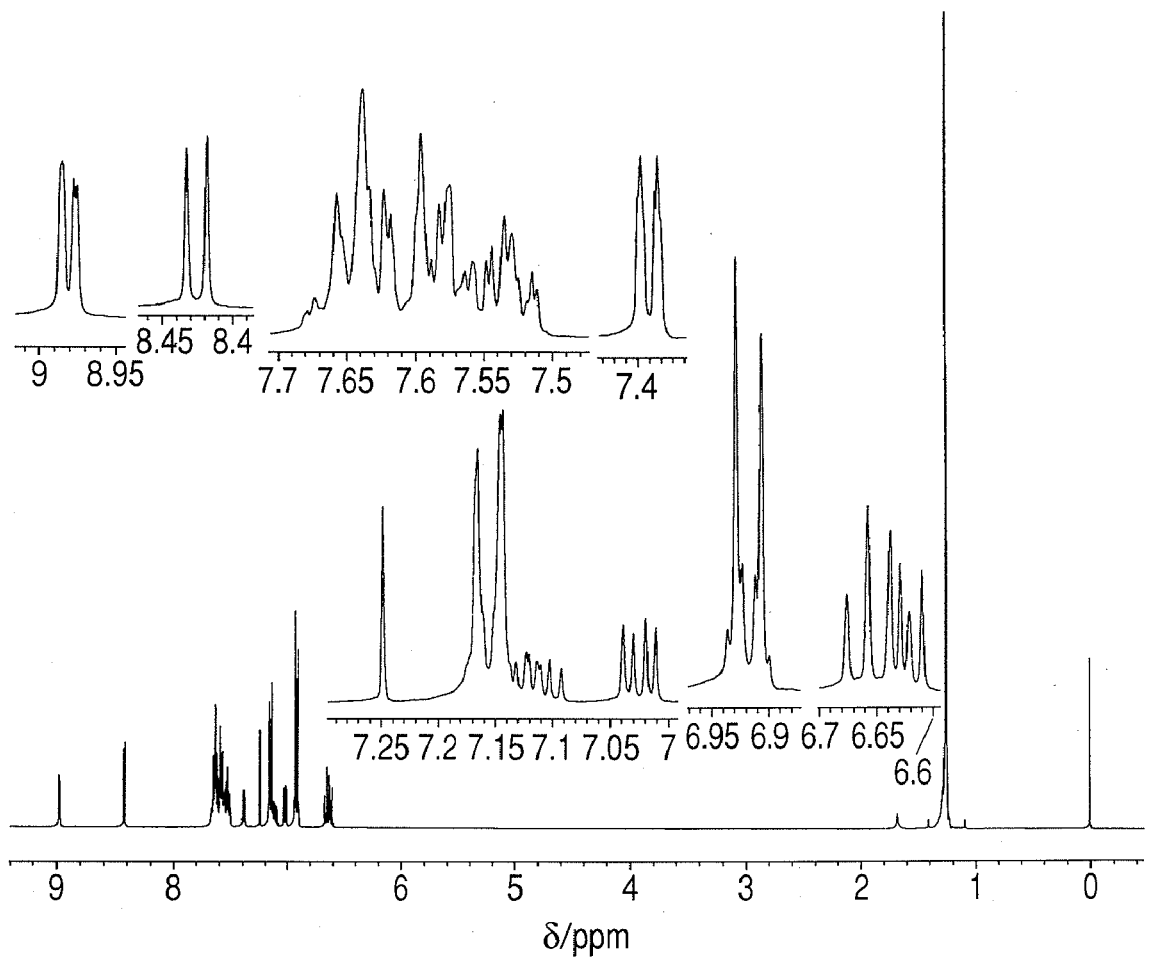
FIG. 19 is a diagram showing the $^1$H-NMR (CDCl$_3$) spectrum of Exemplified Compound 1653.

Further, NMR measurement identified the structure of the compound (FIG. 19).

The PL spectrum of a solution ($1.0\times10^{-5}$ mol/L) of Exemplified Compound 1653 in toluene was measured. As a result, a green light emission spectrum having a light emission peak at 529 nm, a half width of 66.3 nm, and an excellent color purity was shown.

In addition, the following exemplified compounds can be synthesized in the same manner as in Example 15 except that the following compounds is used instead of di-4-t-butylphenylamine in Example 15. (Di-4-methylphenylamine): Exemplified Compound 1636 (Carbazole): Exemplified Compound 1625

Example 16

A device was produced in the same manner as in Example 11 except that: Compound 19 shown below was used instead of Compound 17 in Example 11; Exemplified Compound 1635 was used instead of Exemplified Compound 1303 in Example 11; and Compound 19 and Exemplified Compound 1635 were co-deposited from the vapor at a weight ratio of 5:95.

The device of this example was observed to emit green light with a luminous efficiency of 8.74 μm/W at an applied voltage of 4.3 V. In addition, the device was observed to emit green light having CIE chromaticity coordinates (x, y) of (0.39, 0.59) and a good color purity.

Further, a voltage was applied to the device for 100 hours under an atmospheric condition with a current density kept at 165 mA/cm². As a result, the initial luminance of the device, that is, 15,700 cd/m² reduced to 12,420 cd/m² in 100 hours. This means that luminance deterioration was small.

Compound 19

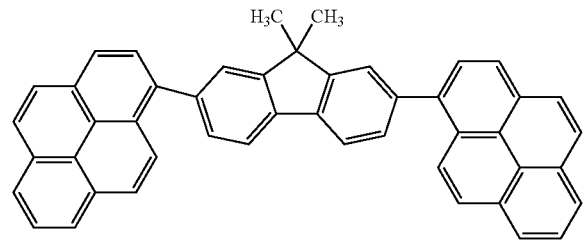

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions This application claims the benefit of Japanese Patent Application No. 2006-213063, filed Aug. 4, 2006 and 2007-118218, filed Apr. 27, 2007, which are incorporated by reference herein in their entirety.

The invention claimed is:

1. A fused heterocyclic compound represented by the following general formula [1]:

[1]

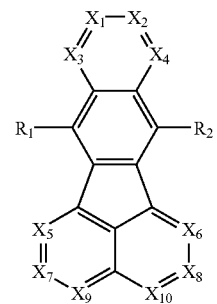

wherein:
X₁ represents a nitrogen atom, X₂ to X₈ each represent CH, one of X₉ and X₁₀ represents CH and the other represents a carbon atom having a substituent R, R represents a substituted or unsubstituted arylamino group or a substituted or unsubstituted fused polycyclic aromatic group having two rings or more to five rings or less; and R₁ and R₂ each represent a phenyl group.

2. A fused heterocyclic compound represented by the following general formula [5]:

[5]

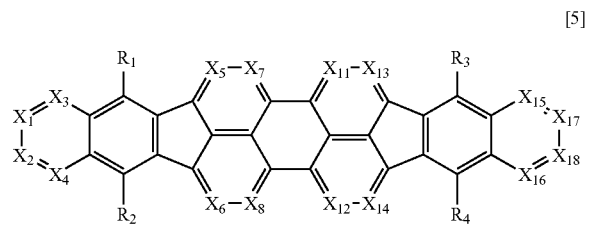

wherein:
X₁ represents a nitrogen atom, X₂ to X₈ and X₁₁ to X₁₆ each represent CH, X₁₇ and X₁₈ each represent CH, or one of X₁₇ and X₁₈ represents CH, the other represents a nitrogen atom; and
R₁ and R₂ represent a phenyl group, and R₃ and R₄ each represent a substituted or unsubstituted aryl group.

3. An organic light emitting device comprising:
a pair of electrodes constituted of an anode and a cathode at least one of which is formed of a transparent or semi-transparent electrode material; and
a layer containing an organic compound, the layer being interposed between the pair of electrodes,
wherein the layer containing an organic compound contains the fused heterocyclic compound according to claim 1.

4. An organic light emitting device according to claim 3, wherein the layer containing the fused heterocyclic compound comprises at least two kinds of compounds of a host and a guest.

5. An organic light emitting device according to claim 4, wherein the guest comprises the fused heterocyclic compound, and the host comprises a compound having an energy gap larger than an energy gap of the fused heterocyclic compound.

6. An organic light emitting device according to claim 5, wherein the guest has a reduction potential higher than that of the host by 0.3 V or more.

7. An organic light emitting device according to claim 3, wherein the layer containing the fused heterocyclic compound comprises at least one layer having a light emitting region.

8. An organic light emitting device according to claim 7, wherein the at least one layer having the light emitting region comprises a light emitting layer.

9. An organic light emitting device comprising:
a pair of electrodes constituted of an anode and a cathode at least one of which is formed of a transparent or semi-transparent electrode material; and
a layer containing an organic compound, the layer being interposed between the pair of electrodes,
wherein the layer containing an organic compound contains the fused heterocyclic compound according to claim 2.

10. An organic light emitting device according to claim 9, wherein the layer containing the fused heterocyclic compound comprises at least two kinds of compounds of a host and a guest.

11. An organic light emitting device according to claim 10, wherein the guest comprises the fused heterocyclic compound, and the host comprises a compound having an energy gap larger than an energy gap of the fused heterocyclic compound.

12. An organic light emitting device according to claim 11, wherein the guest has a reduction potential higher than that of the host by 0.3 V or more.

13. An organic light emitting device according to claim 9, wherein the layer containing the fused heterocyclic compound comprises at least one layer having a light emitting region.

14. An organic light emitting device according to claim 13, wherein the at least one layer having the light emitting region comprises a light emitting layer.

* * * * *